(12) United States Patent
Nti-Addae et al.

(10) Patent No.: US 11,466,015 B2
(45) Date of Patent: Oct. 11, 2022

(54) CRYSTALLINE FORMS OF 8-(2-FLUOROBENZYL)-6-(3-(TRIFLUOROMETHYL)-1H-1,2,4-TRIAZOL-5-YL)IMIDAZO[1,2-A]PYRAZINE AS SGC STIMULATORS

(71) Applicant: Cyclerion Therapeutics, Inc., Cambridge, MA (US)

(72) Inventors: Kwame W. Nti-Addae, Tewksbury, MA (US); Leena Kumari Prasad, San Francisco, CA (US); Thomas Storz, Lowell, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 10 days.

(21) Appl. No.: 16/976,430

(22) PCT Filed: Mar. 7, 2019

(86) PCT No.: PCT/US2019/021080
§ 371 (c)(1),
(2) Date: Aug. 27, 2020

(87) PCT Pub. No.: WO2019/173551
PCT Pub. Date: Sep. 12, 2019

(65) Prior Publication Data
US 2021/0115050 A1    Apr. 22, 2021

Related U.S. Application Data

(60) Provisional application No. 62/639,846, filed on Mar. 7, 2018.

(51) Int. Cl.
*A61K 31/4985* (2006.01)
*C07D 487/04* (2006.01)

(52) U.S. Cl.
CPC ........ *C07D 487/04* (2013.01); *C07B 2200/13* (2013.01)

(58) Field of Classification Search
CPC ................... A61K 31/4985; C07D 487/04

USPC .......................................... 514/249; 544/349
See application file for complete search history.

(56) References Cited

FOREIGN PATENT DOCUMENTS

WO    2016/087342 A1    6/2016
WO    2018/045276 A1    3/2018

OTHER PUBLICATIONS

Roberts et al., Acidic triazoles as soluble guanylate cyclase stimulators. Bioorg Med Chem Lett. Nov. 1, 2011;21(21):6515-8.
International Search Report and Written Opinion for Application No. PCT/US2019/021080, dated Apr. 23, 2019, 9 pages.

*Primary Examiner* — Douglas M Willis
(74) *Attorney, Agent, or Firm* — McCarter & English, LLP; Xin Zhang; James M. Alburger

(57) ABSTRACT

The present disclosure relates to crystalline forms of 8-(2-fluorobenzyl)-6-(3-(trifluoromethyl)-1H-1,2,4-triazol-5-yl) imidazo[1,2-a]pyrazine, depicted below as a compound of Formula (I):

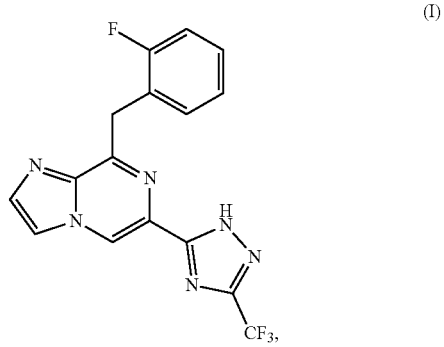

(I)

which are useful as a stimulator of soluble guanylate cyclase (sGC). The present disclosure also provides pharmaceutically acceptable compositions comprising the crystalline forms and methods of using said compositions in the treatment of various disorders.

13 Claims, 32 Drawing Sheets

CRYSTALLINE FORMS OF 8-(2-FLUOROBENZYL)-6-(3-(TRIFLUOROMETHYL)-1H-1,2,4-TRIAZOL-5-YL)IMIDAZO[1,2-A]PYRAZINE AS SGC STIMULATORS

RELATED APPLICATIONS

This application is a 35 U.S.C. § 371 national stage filing of International Application No. PCT/US2019/021080, filed on Mar. 7, 2019, which in turn claims the benefit of the filing date, under 35 U.S.C. § 119(e), of U.S. Provisional Application No. 62/639,846, filed on Mar. 7, 2018. The entire contents of each of the foregoing applications are incorporated herein by reference.

BACKGROUND sGC is the primary receptor for NO in vivo. Upon binding to sGC, NO activates its catalytic domain and results in the conversion of guanosine-5'-triphosphate (GTP) into the secondary messenger cGMP. The increased level of cGMP, in turn, modulates the activity of downstream effectors including protein kinases, phosphodiesterases (PDEs) and ion channels. In the body, NO is synthesized from arginine and oxygen by various nitric oxide synthase (NOS) enzymes and by sequential reduction of inorganic nitrate. Experimental and clinical evidence indicates that reduced NO concentrations, reduced NO bioavailability and/or reduced responsiveness to endogenously produced NO contributes to the development of numerous diseases. sGC stimulators are heme-dependent agonists of the sGC enzyme that work synergistically with varying amounts of NO to increase its enzymatic conversion of GTP to cGMP. sGC stimulators are clearly differentiated from and structurally unrelated to another class of NO-independent, heme-independent agonists of sGC known as sGC activators.

One such sGC stimulator is 8-(2-fluorobenzyl)-6-(3-(trifluoromethyl)-1H-1,2,4-triazol-5-yl)imidazo[1,2-a]pyrazine, depicted below as a compound of Formula (I):

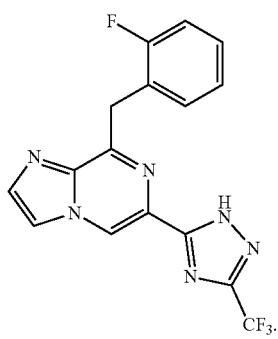

(I)

There is a need for forms of this compound that are crystalline and otherwise have physical properties that are amenable effective delivery of this compound to the patient.

SUMMARY OF THE INVENTION

Provided herein is a novel crystalline Form A of 8-(2-fluorobenzyl)-6-(3-(trifluoromethyl)-1H-1,2,4-triazol-5-yl)imidazo[1,2-a]pyrazine.

Also provided herein is a novel crystalline Form B of 8-(2-fluorobenzyl)-6-(3-(trifluoromethyl)-1H-1,2,4-triazol-5-yl)imidazo[1,2-a]pyrazine.

Also provided herein is a novel crystalline Hydrate 1 of 8-(2-fluorobenzyl)-6-(3-(trifluoromethyl)-1H-1,2,4-triazol-5-yl)imidazo[1,2-a]pyrazine.

Also provided herein is a novel crystalline Hydrate 2 of 8-(2-fluorobenzyl)-6-(3-(trifluoromethyl)-1H-1,2,4-triazol-5-yl)imidazo[1,2-a]pyrazine.

Also provided herein is a novel crystalline Hydrate 3 of 8-(2-fluorobenzyl)-6-(3-(trifluoromethyl)-1H-1,2,4-triazol-5-yl)imidazo[1,2-a]pyrazine.

Also provided herein is a novel crystalline ethanol solvate of 8-(2-fluorobenzyl)-6-(3-(trifluoromethyl)-1H-1,2,4-triazol-5-yl)imidazo[1,2-a]pyrazine.

Also provided herein is a novel crystalline methanol solvate of 8-(2-fluorobenzyl)-6-(3-(trifluoromethyl)-1H-1,2,4-triazol-5-yl)imidazo[1,2-a]pyrazine.

Also provided herein is a novel crystalline methyl ethyl ketone solvate of 8-(2-fluorobenzyl)-6-(3-(trifluoromethyl)-1H-1,2,4-triazol-5-yl)imidazo[1,2-a]pyrazine.

Also provided herein is a novel crystalline dichloromethane solvate of 8-(2-fluorobenzyl)-6-(3-(trifluoromethyl)-1H-1,2,4-triazol-5-yl)imidazo[1,2-a]pyrazine.

Also provided herein is a novel crystalline acetonitrile solvate of 8-(2-fluorobenzyl)-6-(3-(trifluoromethyl)-1H-1,2,4-triazol-5-yl)imidazo[1,2-a]pyrazine.

Further provided herein are pharmaceutical compositions comprising crystalline Form A of 8-(2-fluorobenzyl)-6-(3-(trifluoromethyl)-1H-1,2,4-triazol-5-yl)imidazo[1,2-a]pyrazine, methods for their manufacture, and uses thereof for treating various diseases, wherein an increase in the concentration of nitric oxide (NO) or an increase in the concentration of cyclic Guanosine 3',5'-Monophosphate (cGMP) or both, or an upregulation of the NO pathway is desirable, such as, e.g., CNS diseases.

Further provided herein are pharmaceutical compositions comprising crystalline Form B of 8-(2-fluorobenzyl)-6-(3-(trifluoromethyl)-1H-1,2,4-triazol-5-yl)imidazo[1,2-a]pyrazine, methods for their manufacture, and uses thereof for treating various diseases, wherein an increase in the concentration of nitric oxide (NO) or an increase in the concentration of cyclic Guanosine 3',5'-Monophosphate (cGMP) or both, or an upregulation of the NO pathway is desirable, such as, e.g., CNS diseases.

Further provided herein are pharmaceutical compositions comprising crystalline Hydrate 1 of 8-(2-fluorobenzyl)-6-(3-(trifluoromethyl)-1H-1,2,4-triazol-5-yl)imidazo[1,2-a]pyrazine, methods for their manufacture, and uses thereof for treating various diseases, wherein an increase in the concentration of nitric oxide (NO) or an increase in the concentration of cyclic Guanosine 3',5'-Monophosphate (cGMP) or both, or an upregulation of the NO pathway is desirable, such as, e.g., CNS diseases.

Further provided herein are pharmaceutical compositions comprising crystalline Hydrate 2 of 8-(2-fluorobenzyl)-6-(3-(trifluoromethyl)-1H-1,2,4-triazol-5-yl)imidazo[1,2-a]pyrazine, methods for their manufacture, and uses thereof for treating various diseases, wherein an increase in the concentration of nitric oxide (NO) or an increase in the concentration of cyclic Guanosine 3',5'-Monophosphate (cGMP) or both, or an upregulation of the NO pathway is desirable, such as, e.g., CNS diseases.

Further provided herein are pharmaceutical compositions comprising crystalline Hydrate 3 of 8-(2-fluorobenzyl)-6-(3-(trifluoromethyl)-1H-1,2,4-triazol-5-yl)imidazo[1,2-a]pyrazine, methods for their manufacture, and uses thereof for treating various diseases, wherein an increase in the concentration of nitric oxide (NO) or an increase in the concentration of cyclic Guanosine 3',5'-Monophosphate (cGMP) or both, or an upregulation of the NO pathway is desirable, such as, e.g., CNS diseases (e.g., Alzheimer's disease and mixed dementia).

Further provided herein are pharmaceutical compositions comprising crystalline ethanol solvate, crystalline methanol solvate, crystalline methyl ethyl ketone solvate, crystalline dichloromethane solvate, or crystalline acetonitrile solvate of 8-(2-fluorobenzyl)-6-(3-(trifluoromethyl)-1H-1,2,4-triazol-5-yl)imidazo[1,2-a]pyrazine, methods for their manufacture, and uses thereof for treating various diseases, wherein an increase in the concentration of nitric oxide (NO) or an increase in the concentration of cyclic Guanosine 3',5'-Monophosphate (cGMP) or both, or an upregulation of the NO pathway is desirable, such as, e.g., CNS diseases.

DETAILED DESCRIPTION

Definitions

Figure 1A:
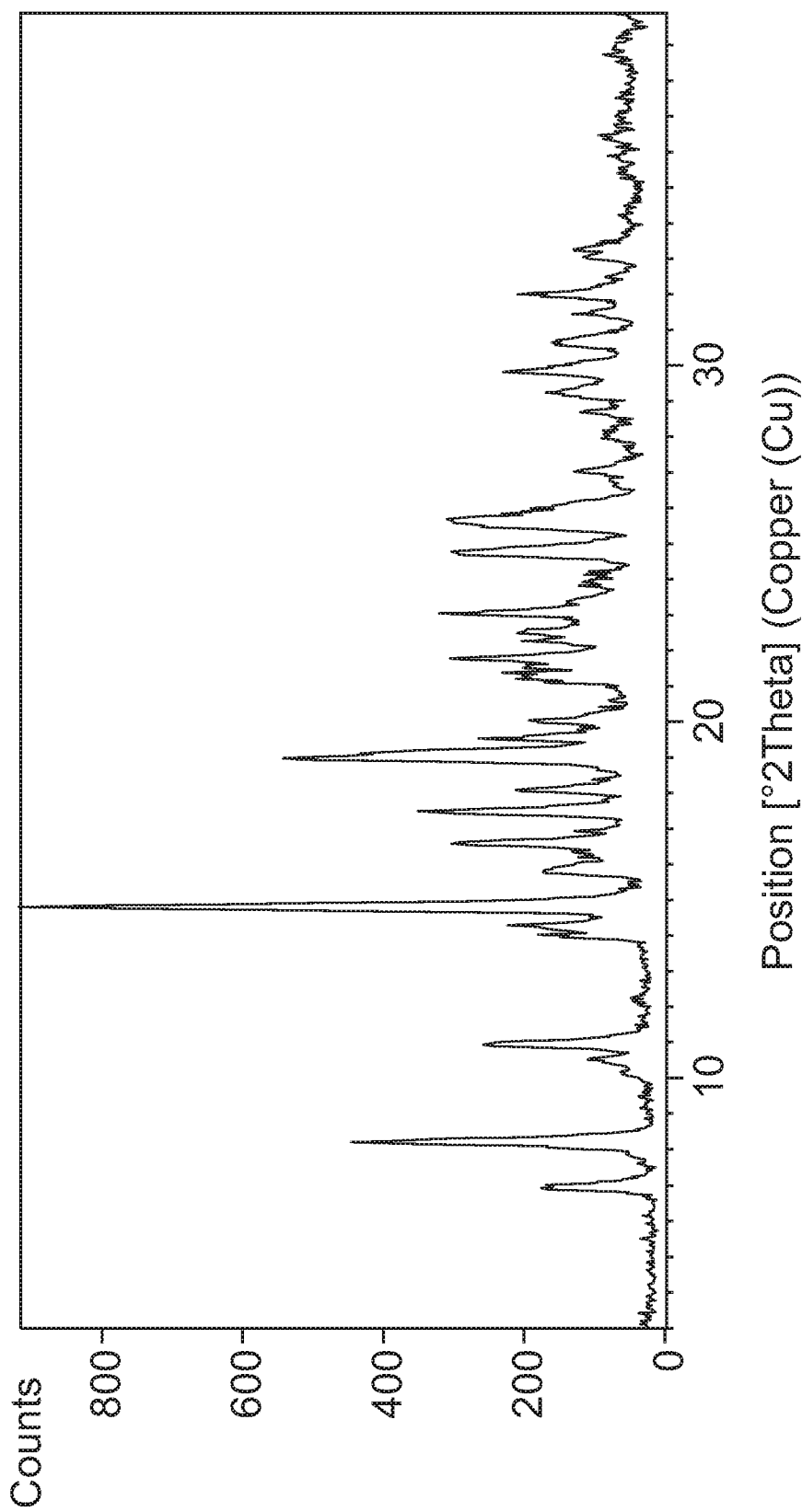
FIG. 1A depicts an X-ray powder diffraction pattern (XRPD) pattern of 8-(2-fluorobenzyl)-6-(3-(trifluoromethyl)-1H-1,2,4-triazol-5-yl)imidazo[1,2-a]pyrazine Form A, acquired at room temperature in reflection mode using a Bruker D8 Discover system.

When used alone, the term "Form A" refers to the crystalline polymorph Form A of 8-(2-fluorobenzyl)-6-(3-(trifluoromethyl)-1H-1,2,4-triazol-5-yl)imidazo[1,2-a]pyrazine. The terms "Form A", "Form A of 8-(2-fluorobenzyl)-6-(3-(trifluoromethyl)-1H-1,2,4-triazol-5-yl)imidazo[1,2-a]pyrazine", and "crystalline Form A of 8-(2-fluorobenzyl)-6-(3-(trifluoromethyl)-1H-1,2,4-triazol-5-yl)imidazo[1,2-a]pyrazine" are used interchangeably. The terms "Form A", "Form A of 8-(2-fluorobenzyl)-6-(3-(trifluoromethyl)-1H-1,2,4-triazol-5-yl)imidazo[1,2-a]pyrazine", and "crystalline Form A of 8-(2-fluorobenzyl)-6-(3-(trifluoromethyl)-1H-1,2,4-triazol-5-yl)imidazo[1,2-a]pyrazine" are intended to include only an anhydrous form of 8-(2-fluorobenzyl)-6-(3-(trifluoromethyl)-1H-1,2,4-triazol-5-yl)imidazo[1,2-a]pyrazine as the free form. Form A can be characterized by, for example, XRPD alone or XRPD in combination with any one or more of DSC, DVS, and TGA.

When used alone, the term "Form B" refers to the crystalline polymorph Form B of 8-(2-fluorobenzyl)-6-(3-(trifluoromethyl)-1H-1,2,4-triazol-5-yl)imidazo[1,2-a]pyrazine. The terms "Form B", "Form B of 8-(2-fluorobenzyl)-6-(3-(trifluoromethyl)-1H-1,2,4-triazol-5-yl)imidazo[1,2-a]pyrazine", and "crystalline Form B of 8-(2-fluorobenzyl)-6-(3-(trifluoromethyl)-1H-1,2,4-triazol-5-yl)imidazo[1,2-a]pyrazine" are used interchangeably. The terms "Form B", "Form B of 8-(2-fluorobenzyl)-6-(3-(trifluoromethyl)-1H-1,2,4-triazol-5-yl)imidazo[1,2-a]pyrazine", and "crystalline Form B of 8-(2-fluorobenzyl)-6-(3-(trifluoromethyl)-1H-1,2,4-triazol-5-yl)imidazo[1,2-a]pyrazine" are intended to include only an anhydrous form of 8-(2-fluorobenzyl)-6-(3-(trifluoromethyl)-1H-1,2,4-triazol-5-yl)imidazo[1,2-a]pyrazine as a free form. Form B can be characterized by, for example, XRPD alone or XRPD in combination with any one or more of DSC, and TGA.

When used alone, the term "Hydrate 1" refers to the crystalline polymorph Hydrate 1 of 8-(2-fluorobenzyl)-6-(3-(trifluoromethyl)-1H-1,2,4-triazol-5-yl)imidazo[1,2-a]pyrazine. The terms "Hydrate 1", "crystalline Hydrate 1", and "crystalline Hydrate 1 of 8-(2-fluorobenzyl)-6-(3-(trifluoromethyl)-1H-1,2,4-triazol-5-yl)imidazo[1,2-a]pyrazine are used interchangeably. The terms "Hydrate 1", "Hydrate 1 of 8-(2-fluorobenzyl)-6-(3-(trifluoromethyl)-1H-1,2,4-triazol-5-yl)imidazo[1,2-a]pyrazine", and "crystalline Hydrate 1 of 8-(2-fluorobenzyl)-6-(3-(trifluoromethyl)-1H-1,2,4-triazol-5-yl)imidazo[1,2-a]pyrazine" are intended to include only a hydrated form of 8-(2-fluorobenzyl)-6-(3-(trifluoromethyl)-1H-1,2,4-triazol-5-yl)imidazo[1,2-a]pyrazine as a free form. Hydrate 1 can be characterized by, for example, XRPD alone or XRPD in combination with any one or more of DSC, and TGA.

When used alone, the term "Hydrate 2" refers to the crystalline polymorph Hydrate 2 of 8-(2-fluorobenzyl)-6-(3-(trifluoromethyl)-1H-1,2,4-triazol-5-yl)imidazo[1,2-a]pyrazine. The terms "Hydrate 2", "crystalline Hydrate 2", and "crystalline Hydrate 2 of 8-(2-fluorobenzyl)-6-(3-(trifluoromethyl)-1H-1,2,4-triazol-5-yl)imidazo[1,2-a]pyrazine are used interchangeably. The terms "Hydrate 2", "Hydrate 2 of 8-(2-fluorobenzyl)-6-(3-(trifluoromethyl)-1H-1,2,4-triazol-5-yl)imidazo[1,2-a]pyrazine", and "crystalline Hydrate 2 of 8-(2-fluorobenzyl)-6-(3-(trifluoromethyl)-1H-1,2,4-triazol-5-yl)imidazo[1,2-a]pyrazine" are intended to include only an hydrated form of 8-(2-fluorobenzyl)-6-(3-(trifluoromethyl)-1H-1,2,4-triazol-5-yl)imidazo[1,2-a]pyrazine as a free form. Hydrate 2 can be characterized by, for example, XRPD alone or XRPD in combination with any one or more of DSC, and TGA.

When used alone, the term "Hydrate 3" refers to the crystalline polymorph Hydrate 3 of 8-(2-fluorobenzyl)-6-(3-(trifluoromethyl)-1H-1,2,4-triazol-5-yl)imidazo[1,2-a]pyrazine. The terms "Hydrate 3", "crystalline Hydrate 3", and "crystalline Hydrate 3 of 8-(2-fluorobenzyl)-6-(3-(trifluoromethyl)-1H-1,2,4-triazol-5-yl)imidazo[1,2-a]pyrazine are used interchangeably. The terms "Hydrate 3", "Hydrate 3 of 8-(2-fluorobenzyl)-6-(3-(trifluoromethyl)-1H-1,2,4-triazol-5-yl)imidazo[1,2-a]pyrazine", and "crystalline Hydrate 3 of 8-(2-fluorobenzyl)-6-(3-(trifluoromethyl)-1H-1,2,4-triazol-5-yl)imidazo[1,2-a]pyrazine" are intended to include only an hydrated form of 8-(2-fluorobenzyl)-6-(3-(trifluoromethyl)-1H-1,2,4-triazol-5-yl)imidazo[1,2-a]pyrazine as a free form. Hydrate 3 can be characterized by, for example, XRPD alone or XRPD in combination with any one or more of DSC, and TGA.

As used herein, the term "Form" as in Form A and Form B refers to a crystalline solid adduct containing only 8-(2-fluorobenzyl)-6-(3-(trifluoromethyl)-1H-1,2,4-triazol-5-yl) imidazo[1,2-a]pyrazine (i.e., the compound of Formula (I)).

As used herein, "crystalline" refers to a solid having a crystal structure wherein the individual molecules have a highly homogeneous regular locked-in chemical configuration.

"Anhydrous" as used herein, means that the crystalline form comprises substantially no water in the crystal lattice e.g., less than 1% by weight as determined by Karl Fisher (KF), or less than 1% by weight as determined by another quantitative analysis.

As used herein, the term "solvate" as in crystalline ethanol solvate, crystalline methanol solvate, crystalline methyl ethyl ketone solvate, crystalline dichloromethane solvate, and crystalline acetonitrile solvate refers to a crystalline solid adduct containing a compound of Formula (I) and either stoichiometric or nonstoichiometric amounts of a solvent incorporated within the crystal structure. Techniques known to one of skill in the art to determine the to determine the amount of solvent present include, for example, HPLC, LCMS, GC, TGA, $^1$H NMR etc.

As used herein, the term "Hydrate" as in Hydrate 1, Hydrate 2 and Hydrate 3 refers to a crystalline solid adduct containing a compound of Formula (I) and either stoichiometric or nonstoichiometric amounts of a water incorporated within the crystal structure. Techniques known to one of skill in the art to determine the to determine the amount of water present include, for example, TGA and KF.

Solid state ordering of solids may be determined by standard techniques known in the art, e.g., by X-ray powder diffraction (XRPD), differential scanning calorimetry (DSC), or thermal gravimetric analysis (TGA). Amorphous solids can also be differentiated from crystalline solids e.g., by birefringence using polarized light microscopy. Amorphous solids consist of disordered arrangements of molecules and do not possess a distinguishable crystal lattice.

Relative intensity is calculated as a ratio of the peak intensity of the peak of interest versus the peak intensity of the largest peak. In certain embodiments, the relative intensity of the peaks may vary due to the preferred orientation of the sample. Preferred orientation in the specimen influences the intensities of various reflections so that some are more intense and others less intense, compared to what would be expected from a completely random specimen. In general, the morphology of many crystalline particles tends to give a specimen that exhibits some degree of preferred orientation in the specimen holder. This is particularly evident for needlelike or plate-like crystals when size reduction yields finer needles or platelets.

In certain embodiments, the XRPD patterns are acquired at room temperature in reflection mode using a Bruker D8 Discover system equipped with a sealed tube source and a Hi-Star area detector (Bruker AXS, Madison, Wis.). The X-Ray generator was operated at a voltage of 40 kV and a current of 40 mA with a Cu-anode as X-ray source (CuKα1 radiation, λ=1.54056 Å, 40 kV, 40 mA). The powder sample was placed in a low-background holder. The data was subsequently integrated over the range of 5.000°-45.000° 2θ with a step size of 0.020° and merged into one continuous pattern. Alternatively, XRPD patterns are acquired at room temperature in reflection mode using a Panalytical Empyrean system equipped with a sealed tube source and a PIXcel$^{ID}$ detector. The X-Ray generator is operated at a voltage of 45 kV and a current of 40 mA with a Cu-anode as X-ray source (CuKα1 radiation, λ=1.54056 Å, 40 kV, 40 mA). The powder sample is placed in a zero-background holder. The data is subsequently integrated over the range of 4.0°-40.0° 2θ with a step size of 0.026° and merged into one continuous pattern.

In some embodiments, Form A is at least 70%, 80%, 90%, 95%, 98%, 99%, 99.5%, or 99.9% pure. The purity of Form A is determined by dividing the weight of Form A of the compound of Formula (I) in a composition comprising the compound of Formula (I) over the total weight of the compound of Formula (I) in the composition.

In some embodiments, Form B is at least 70%, 80%, 90%, 95%, 98%, 99%, 99.5%, or 99.9% pure. The purity of Form B is determined by dividing the weight of Form B of the compound of Formula (I) in a composition comprising the compound of Formula (I) over the total weight of the compound of Formula (I) in the composition.

In some embodiments, Hydrate 1 is at least 70%, 80%, 90%, 95%, 98%, 99%, 99.5%, or 99.9% pure. The purity of Hydrate 1 is determined by dividing the weight of Hydrate 1 of the compound of Formula (I) in a composition comprising the compound of Formula (I) over the total weight of the compound of Formula I in the composition.

In some embodiments, Hydrate 2 is at least 70%, 80%, 90%, 95%, 98%, 99%, 99.5%, or 99.9% pure. The purity of Hydrate 2 is determined by dividing the weight of Hydrate 2 of the compound of Formula (I) in a composition comprising the compound of Formula (I) over the total weight of the compound of Formula (I) in the composition.

In some embodiments, Hydrate 3 is at least 70%, 80%, 90%, 95%, 98%, 99%, 99.5%, or 99.9% pure. The purity of Hydrate 3 is determined by dividing the weight of Hydrate 3 of the compound of Formula (I) in a composition comprising the compound of Formula (I) over the total weight of the compound of Formula (I) in the composition.

In some embodiments, crystalline ethanol solvate, crystalline methanol solvate, crystalline methyl ethyl ketone solvate, crystalline dichloromethane solvate, or crystalline acetonitrile solvate is at least 70%, 80%, 90%, 95%, 98%, 99%, 99.5%, or 99.9% pure. The purity of crystalline ethanol solvate, crystalline methanol solvate, crystalline methyl ethyl ketone solvate, crystalline dichloromethane solvate, or crystalline acetonitrile solvate is determined by dividing the weight of crystalline ethanol solvate, crystalline methanol solvate, crystalline methyl ethyl ketone solvate, crystalline dichloromethane solvate, or crystalline acetonitrile solvate of the compound of Formula (I) in a composition comprising the compound of Formula (I) over the total weight of the compound of Formula (I) in the composition.

Description of Exemplary Compounds

The crystalline forms disclosed in the present application, for example, Form A, Form B, Hydrate 1, Hydrate 2, and Hydrate 3, have numerous advantages and solve problems associated with the ethyl acetate solvate of Formula (I) as described in International Application No. PCT/JS2017/049834, such as high stability and suitability for pharmaceutical uses. In particular, Form A and Form B are more stable than the ethyl acetate solvate. In addition, Form A, Form B, Hydrate 1, Hydrate 2, and Hydrate 3 are all suitable for pharmaceutical use, whereas the ethyl acetate solvate is incompatible with a formulation for human use. Other advantages may include favorable pharmacokinetic properties, ease of isolation, process reproducibility, suitability for large scale manufacturing process, etc.

It is to be understood that for comparison purposes some variability in peak position from those listed below for Form A, Form B, Hydrate 1, Hydrate 2, and Hydrate 3 and in Tables 1A, 1B, 2A, 2B, 3A, 3B, 4A, 4B, 5A, 5B, 6, 7, 8, 9, 10, and 11 are allowed, such as ±0.2 degrees two theta. In a particular embodiment, the variation for a given peak is 0.2 degrees two theta.

In one aspect, the present disclosure provides crystalline Form A of 8-(2-fluorobenzyl)-6-(3-(trifluoromethyl)-1H-1,2,4-triazol-5-yl)imidazo[1,2-a]pyrazine.

In one aspect, crystalline Form A of 8-(2-fluorobenzyl)-6-(3-(trifluoromethyl)-1H-1,2,4-triazol-5-yl)imidazo[1,2-a]pyrazine is characterized by x-ray powder diffraction pattern. The x-ray powder diffraction pattern can be acquired at room temperature in reflection mode using a Bruker D8 Discover system described herein. In one embodiment, crystalline Form A is characterized by at least three, at least four, or at least five x-ray powder diffraction peaks at 2Θ angles selected from 7.0°, 8.3°, 11.1°, 14.3°, and 15.0°. Alternatively, crystalline Form A is characterized by at least three, at least four, at least five, at least six, at least seven, at least eight, at least nine, or at least ten x-ray powder diffraction peaks at 2Θ angles 7.0°, 8.3°, 11.1°, 14.3°, 15.0°, 15.9°, 16.7°, 17.6°, 19.1°, 20.2°, 21.6°, 24.9°, and 25.8°. Alternatively, crystalline Form A is characterized by x-ray powder diffraction peaks at 2Θ angles 7.0°, 8.3°, 11.1°, 14.3°, 15.0°, 15.9°, 16.7°, 17.6°, 19.1°, 20.2°, 21.6°, 24.9°, and 25.8°. Alternatively, crystalline Form A is characterized by at least three, at least four, at least five, at least six, at least seven, at least eight, or at least nine x-ray powder diffraction peaks at 2Θ angles 7.0°, 8.3°, 11.1°, 14.3°, 15.0°, 17.6°, 19.1°, 20.2°, and 21.6°. Alternatively, crystalline Form A is characterized by x-ray powder diffraction peaks at 2Θ angles 7.0°, 8.3°, 11.1°, 14.3°, 15.0°, 17.6°, 19.1°, 20.2°, and 21.6°. Alternatively, crystalline Form A is characterized by at least three, at least four, at least five, at least six, at least seven, at least eight, at least nine, or at least ten x-ray powder diffraction peaks at 2Θ angles selected from 4.9°, 7.0°, 8.3°, 10.6°, 11.1°, 14.3°, 15.0°, 15.9°, 16.7°, 17.6°, 18.2°, 19.1°, 19.7°, 20.2°, 21.6°, 23.2°, 24.9°, 25.8°, 27.1°, 28.2°, 28.8°, 29.9°, 30.8°, 32.1°, and 33.1°. In another alternative crystalline Form A is characterized by x-ray powder diffraction peaks at 2Θ angles 4.9°, 7.0°, 8.3°, 10.6°, 11.1°, 14.3°, 15.0°, 15.9°, 16.7°, 17.6°, 18.2°, 19.1°, 19.7°, 20.2°, 21.6°, 23.2°, 24.9°, 25.8°, 27.1°, 28.2°, 28.8°, 29.9°, 30.8°, 32.1°, and 33.1°. In some embodiments, the peaks described above for crystalline Form A have a relative intensity of at least 10%, of at least 15%, of at least 20%, or of at least 25%.

In another aspect, crystalline Form A of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 1A.

In another aspect, crystalline Form A of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 1A.

In one aspect, crystalline Form A of 8-(2-fluorobenzyl)-6-(3-(trifluoromethyl)-1H-1,2,4-triazol-5-yl)imidazo[1,2-a]pyrazine is characterized by x-ray powder diffraction pattern, acquired at room temperature in reflection mode using a Panalytical Empyrean system described herein. In one embodiment, crystalline Form A is characterized by at least three, at least four, or at least five x-ray powder diffraction peaks at 2Θ angles selected from 8.3°, 8.5°, 11.3°, 15.0°, 15.2°, and 19.3°. Alternatively, crystalline Form A is characterized by at least three, at least four, at least five, at least six, at least seven, at least eight, at least nine, or at least ten x-ray powder diffraction peaks at 2Θ angles 7.0°, 8.3°, 8.5°, 11.3°, 15.0°, 15.2°, 16.2°, 17.0°, 17.8°, 19.3°, 19.9°, 21.6°, 22.0°, and 22.2°. Alternatively, crystalline Form A is characterized by x-ray powder diffraction peaks at 2Θ angles 7.0°, 8.3°, 8.5°, 11.3°, 15.0°, 15.2°, 16.2°, 17.0°, 17.8°, 19.3°, 19.9°, 21.6°, 22.0°, and 22.2°. Alternatively, crystalline Form A is characterized by at least three, at least four, at least five, at least six, at least seven, at least eight, at least nine, or at least ten x-ray powder diffraction peaks at 2Θ angles selected from 5.0°, 7.0°, 7.2°, 8.3°, 8.5°, 10.4°, 10.8°, 11.3°, 12.4°, 14.2°, 14.4°, 14.6°, 15.0°, 15.2°, 16.2°, 17.0°, 17.8°, 18.5°, 19.3°, 19.9°, 20.3°, 21.6°, 22.0°, 22.2°, 22.6°, 22.9°, 23.4°, 24.2°, 25.1°, 25.7°, 25.9°, 26.4°, 27.4°, 28.4°, 29.0°, 29.6°, 30.1°, 30.2°, 31.0°, 31.8°, 32.2°, 33.3°, 33.7°, 36.2°, and 36.7°. In another alternative crystalline Form A is characterized by x-ray powder diffraction peaks at 2Θ angles 5.0°, 7.0°, 7.2°, 8.3°, 8.5°, 10.4°, 10.8°, 11.3°, 12.4°, 14.2°, 14.4°, 14.6°, 15.0°, 15.2°, 16.2°, 17.0°, 17.8°, 18.5°, 19.3°, 19.9°, 20.3°, 21.6°, 22.0°, 22.2°, 22.6°, 22.9°, 23.4°, 24.2°, 25.1°, 25.7°, 25.9°, 26.4°, 27.4°, 28.4°, 29.0°, 29.6°, 30.1°, 30.2°, 31.0°, 31.8°, 32.2°, 33.3°, 33.7°, 36.2°, and 36.7°. In some embodiments, the peaks described above for crystalline Form A have a relative intensity of at least 10%, of at least 15%, of at least 20%, or of at least 25%.

Figure 1B:
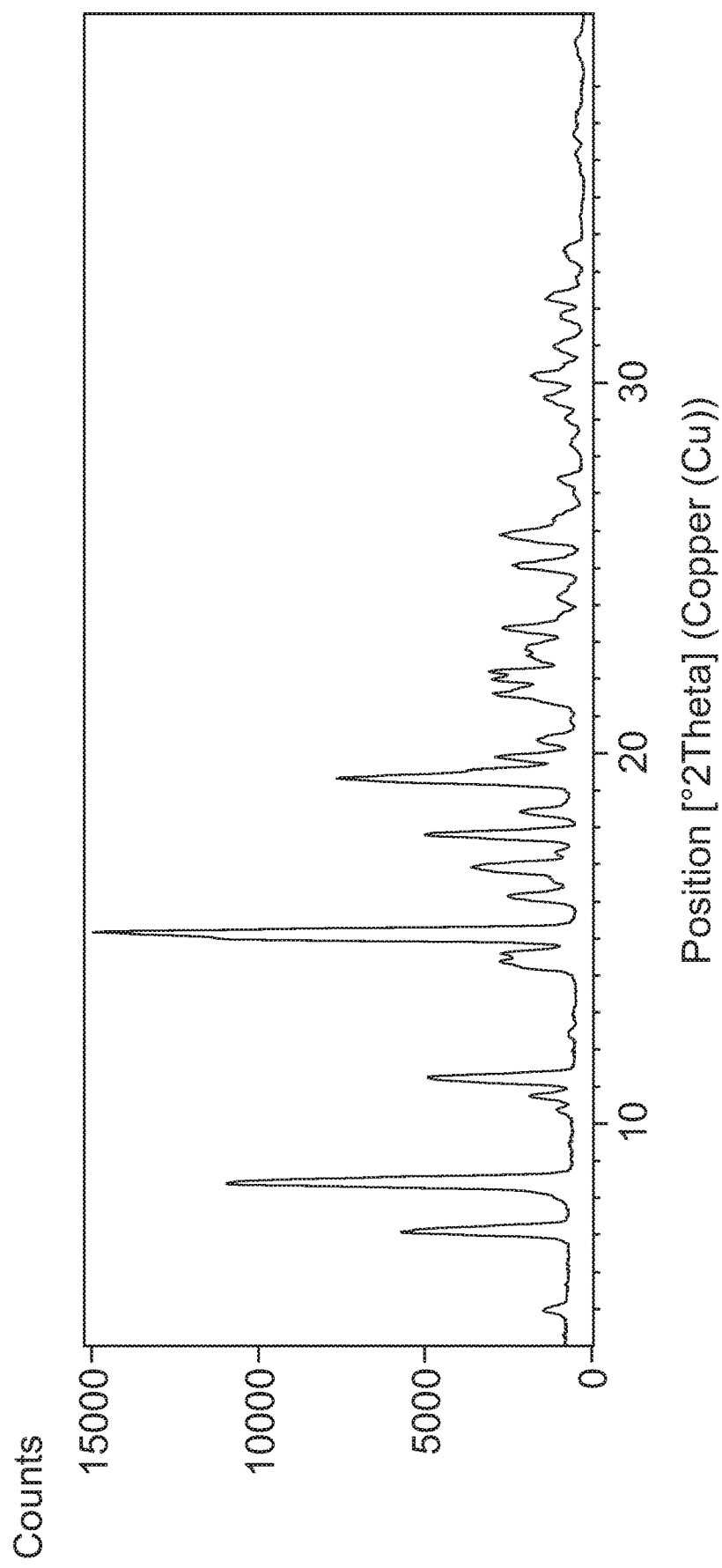
FIG. 1B depicts an X-ray powder diffraction pattern (XRPD) pattern of 8-(2-fluorobenzyl)-6-(3-(trifluoromethyl)-1H-1,2,4-triazol-5-yl)imidazo[1,2-a]pyrazine Form A, acquired at room temperature in reflection mode using a Panalytical Empyrean system.

In another aspect, crystalline Form A of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 1B.

In another aspect, crystalline Form A of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 1B.

Figure 2:
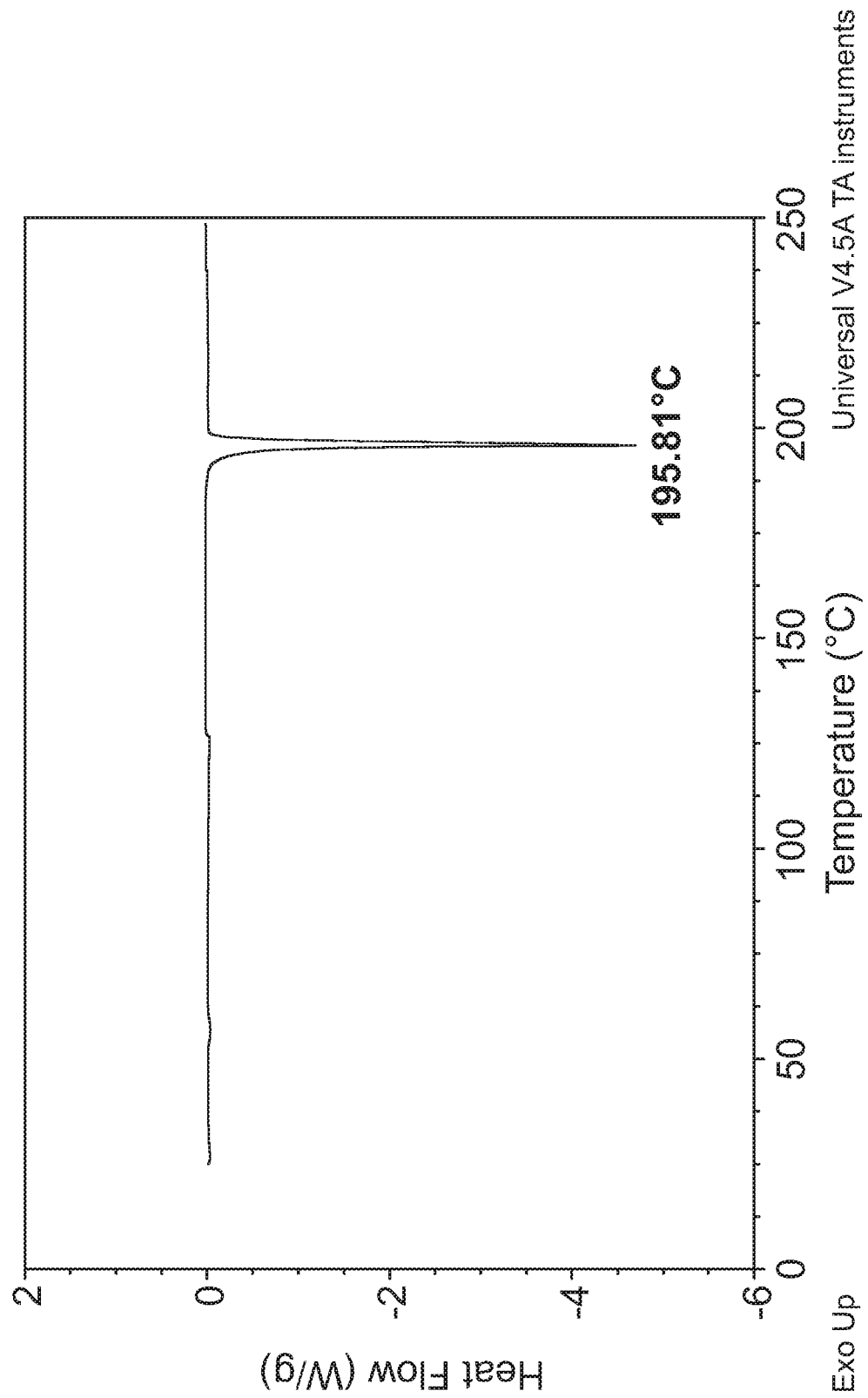
FIG. 2 depicts a differential scanning calorimetry (DSC) analysis of 8-(2-fluorobenzyl)-6-(3-(trifluoromethyl)-1H-1,2,4-triazol-5-yl)imidazo[1,2-a]pyrazine Form A.

In one aspect, crystalline Form A of 8-(2-fluorobenzyl)-6-(3-(trifluoromethyl)-1H-1,2,4-triazol-5-yl)imidazo[1,2-a]pyrazine has a DSC pattern that is substantially the same DSC pattern shown in FIG. 2. In particular, crystalline Form A is characterized by DSC melting temperature of 195° C.±2° C.

Figure 3:
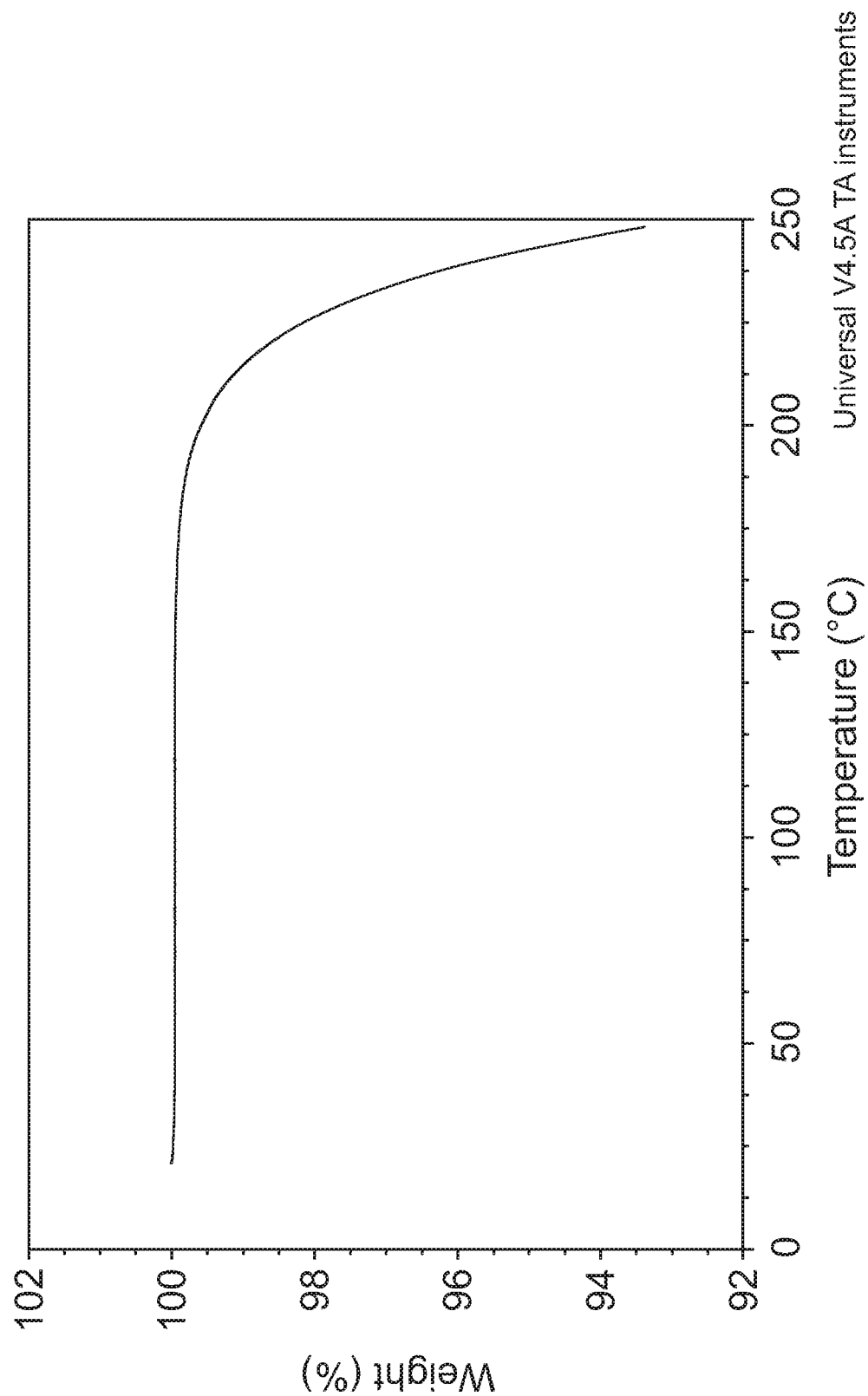
FIG. 3 depicts a thermal gravimetric analysis (TGA) of 8-(2-fluorobenzyl)-6-(3-(trifluoromethyl)-1H-1,2,4-triazol-5-yl)imidazo[1,2-a]pyrazine Form A.

In one aspect, crystalline Form A of 8-(2-fluorobenzyl)-6-(3-(trifluoromethyl)-1H-1,2,4-triazol-5-yl)imidazo[1,2-a]pyrazine has a TGA pattern that is substantially the same TGA pattern shown in FIG. 3.

Figure 4:
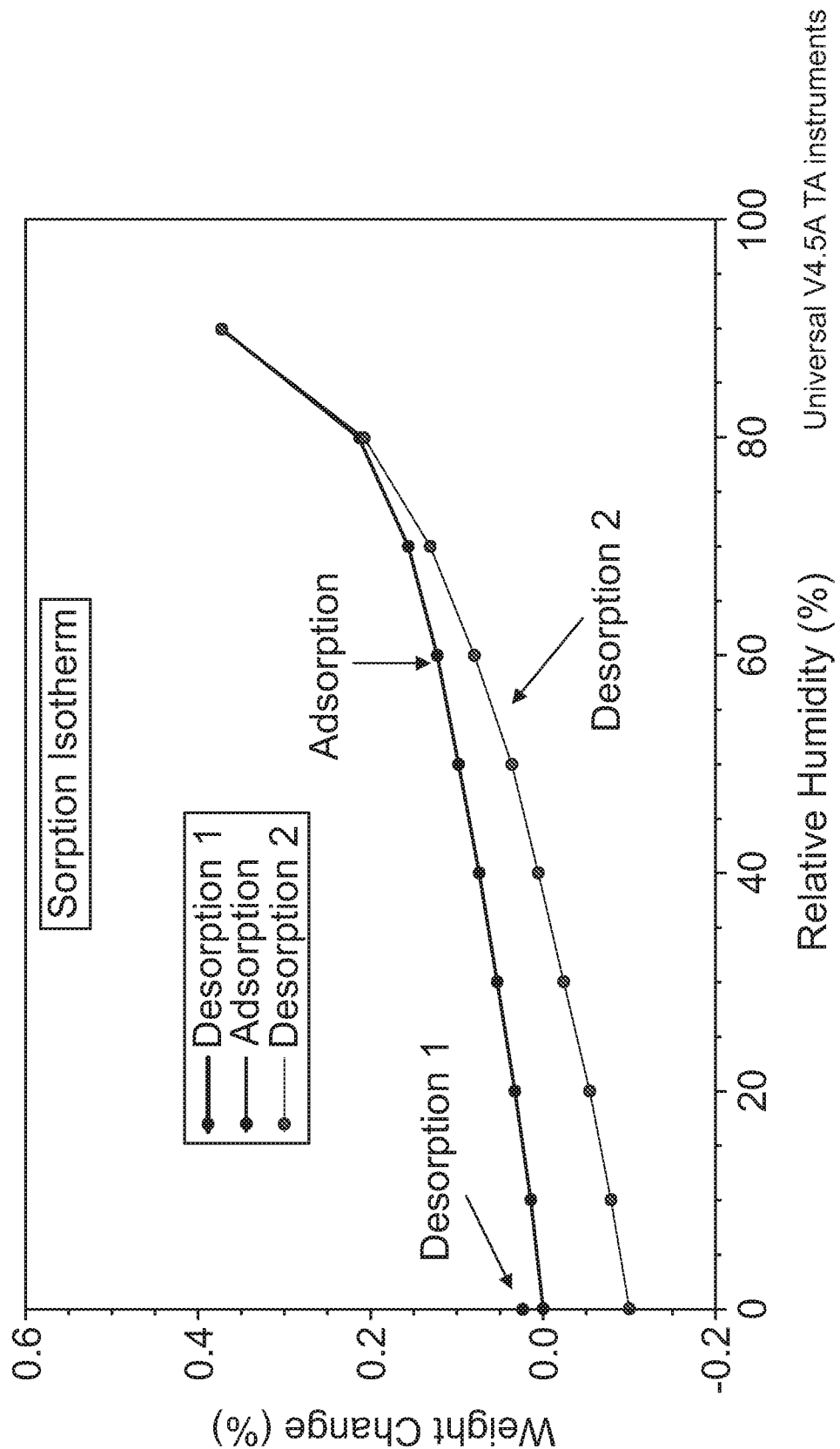
FIG. 4 depicts a dynamic vapor sorption (DVS) analysis of 8-(2-fluorobenzyl)-6-(3-(trifluoromethyl)-1H-1,2,4-triazol-5-yl)imidazo[1,2-a]pyrazine Form A.

In one aspect, crystalline Form A of 8-(2-fluorobenzyl)-6-(3-(trifluoromethyl)-1H-1,2,4-triazol-5-yl)imidazo[1,2-a]pyrazine has a DVS pattern that is substantially the same DVS pattern shown in FIG. 4.

In one aspect, the crystalline Form A of 8-(2-fluorobenzyl)-6-(3-(trifluoromethyl)-1H-1,2,4-triazol-5-yl)imidazo[1,2-a]pyrazine is characterized by at least three, at least four, or by at least five, x-ray powder diffraction peaks at 2Θ angles selected from 7.0°, 8.3°, 11.1°, 14.3°, and 15.0°; optionally together with one, two, or three of the TGA, DSC, DVS parameters recited above for Form A. Alternatively, crystalline Form A is characterized by at least three, at least four, at least five, at least six, at least seven, at least eight, at least nine, or at least ten x-ray powder diffraction peaks at 2Θ angles selected from 7.0°, 8.3°, 11.1°, 14.3°, 15.0°, 15.9°, 16.7°, 17.6°, 19.1°, 20.2°, 21.6°, 24.9°, and 25.8° optionally together with one, two, or three of the TGA, DSC, DVS parameters recited above for Form A.

In one aspect, the crystalline Form A of 8-(2-fluorobenzyl)-6-(3-(trifluoromethyl)-1H-1,2,4-triazol-5-yl)imidazo[1,2-a]pyrazine is characterized by at least three, at least four, or by at least five, x-ray powder diffraction peaks at 2Θ angles selected from 8.3, 8.5°, 11.3°, 15.0°, 15.2°, and 19.3°; optionally together with one, two, or three of the TGA, DSC, DVS parameters recited above for Form A. Alternatively, crystalline Form A is characterized by at least three, at least four, at least five, at least six, at least seven, at least eight, at least nine, or at least ten x-ray powder diffraction peaks at 2Θ angles selected from 7.0°, 8.3°, 8.5°, 11.3°, 15.0°, 15.2°, 16.2°, 17.0°, 17.8°, 19.3°, 19.9°, 21.6°, 22.0°, and 22.2° optionally together with one, two, or three of the TGA, DSC, DVS parameters recited above for Form A.

In one aspect, the crystalline Form A of 8-(2-fluorobenzyl)-6-(3-(trifluoromethyl)-1H-1,2,4-triazol-5-yl)imidazo[1,2-a]pyrazine is characterized by at least three, at least four, at least five, at least six, at least seven, at least eight, or at least nine x-ray powder diffraction peaks at 2Θ angles 7.0°, 8.3°, 11.1°, 14.3°, 15.0°, 17.6°, 19.1°, 20.2°, and 21.6° optionally together with one, two, or three of the TGA, DSC, DVS parameters recited above for Form A.

In one aspect, crystalline Form B of 8-(2-fluorobenzyl)-6-(3-(trifluoromethyl)-1H-1,2,4-triazol-5-yl)imidazo[1,2-a]pyrazine is characterized by x-ray powder diffraction pattern. The x-ray powder diffraction pattern can be acquired at room temperature in reflection mode using a Bruker D8 Discover system described herein. In one embodiment, crystalline Form B is characterized by at least three, at least four, or at least five x-ray powder diffraction peaks at 2Θ angles selected from 8.9°, 12.2°, 13.6°, 17.2°, and 21.0°. Alternatively, crystalline Form B is characterized by at least three, at least four, at least five, at least six, at least seven, at least eight, at least nine, or at least ten x-ray powder diffraction peaks at 2Θ angles selected from 8.9°, 12.2°, 13.6°, 14.5°, 15.7°, 17.2°, 17.7°, 21.0°, 22.7°, 23.9°, 25.0°, 26.7°, and 27.6°. Alternatively, crystalline Form B is characterized by x-ray powder diffraction peaks at 2Θ angles 8.9°, 12.2°, 13.6°, 14.5°, 15.7°, 17.2°, 17.7°, 21.0°, 22.7°, 23.9°, 25.0°, 26.7°, and 27.6°. Alternatively, crystalline Form B is characterized by at least three, at least four, at least five, at least six, at least seven, at least eight, or at least nine, x-ray powder diffraction peaks at 2Θ angles selected from 8.9°, 12.2°, 13.6°, 14.5°, 15.7°, 17.2°, 21.0°, 22.7°, and 23.9°. Alternatively, crystalline Form B is characterized by x-ray powder diffraction peaks at 2Θ angles 8.9°, 12.2°, 13.6°, 14.5°, 15.7°, 17.2°, 21.0°, 22.7°, and 23.9°. In another alternative crystalline Form B is characterized by x-ray powder diffraction peaks at 2Θ angles 8.9°, 12.2°, 13.6°, 14.5°, 15.7°, 17.2°, 17.7°, 18.3°, 21.0°, 22.7°, 23.9°, 24.2°, 25.0°, 25.6°, 26.7°, 27.6°, and 29.6°. In some embodiments, the peaks described above for crystalline Form B have a relative intensity of at least 10%, of at least 15%, of at least 20%, or of at least 25%.

Figure 5A:
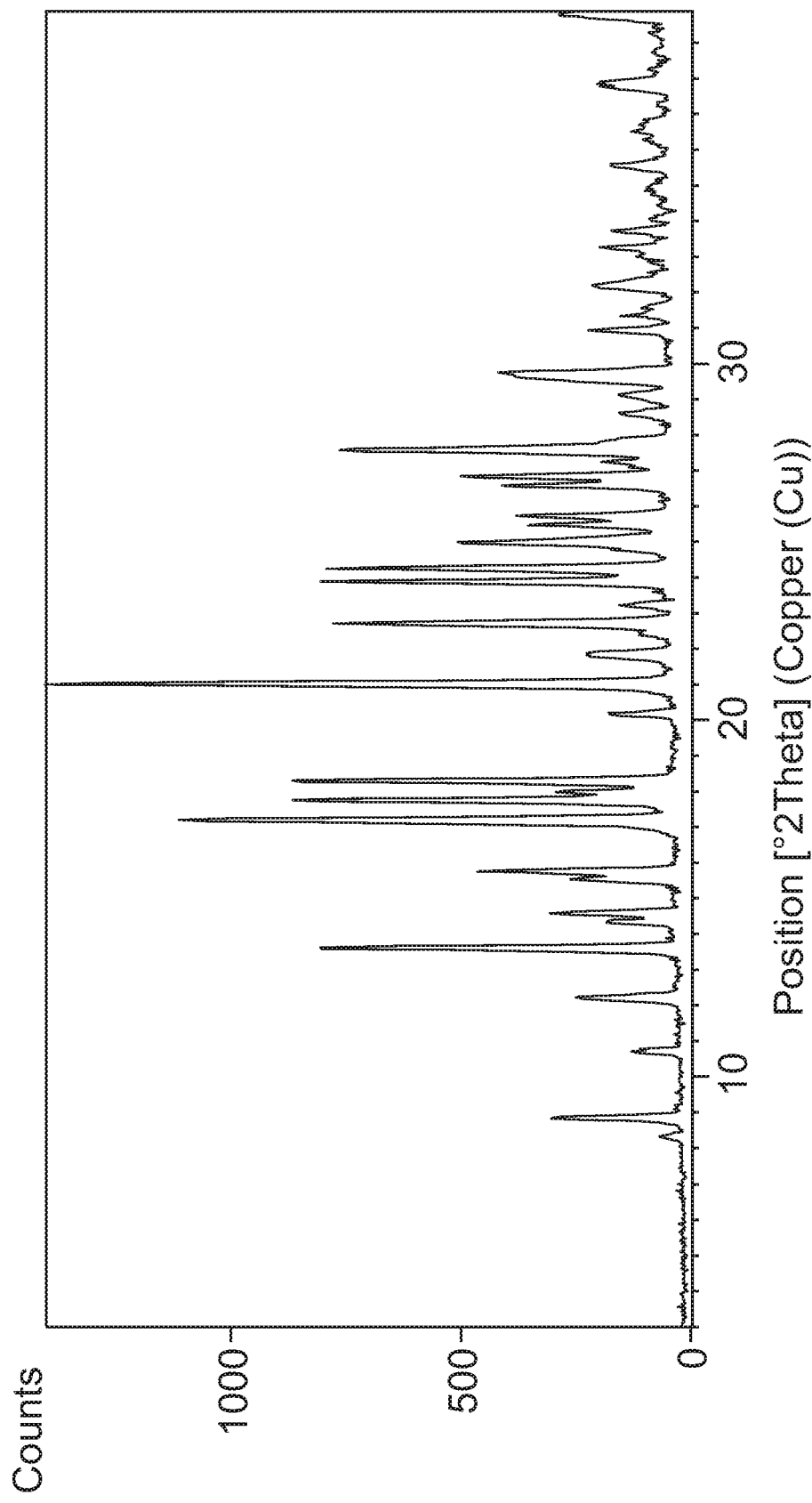
FIG. 5A depicts an XRPD pattern of 8-(2-fluorobenzyl)-6-(3-(trifluoromethyl)-1H-1,2,4-triazol-5-yl)imidazo[1,2-a]pyrazine Form B, acquired at room temperature in reflection mode using a Bruker D8 Discover system.

In another aspect, crystalline Form B of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 5A.

In another aspect, crystalline Form B of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 2A.

In one aspect, crystalline Form B of 8-(2-fluorobenzyl)-6-(3-(trifluoromethyl)-1H-1,2,4-triazol-5-yl)imidazo[1,2-a]pyrazine is characterized by x-ray powder diffraction pattern, acquired at room temperature in reflection mode using a Panalytical Empyrean system described herein. In one embodiment, crystalline Form B is characterized by at least three, at least four, or at least five x-ray powder diffraction peaks at 2Θ angles selected from 13.8°, 16.0°, 17.4°, 18.0°, 18.5°, and 21.2°. Alternatively, crystalline Form B is characterized by at least three, at least four, at least five, at least six, at least seven, at least eight, at least nine, or at least ten x-ray powder diffraction peaks at 2Θ angles selected from 9.1°, 10.9°, 12.4°, 13.8°, 14.8°, 16.0°, 17.4°, 18.0°, 18.5°, 21.2°, 22.9°, 24.1°, 24.5°, 27.8°, 30.0°. Alternatively, crystalline Form B is characterized by x-ray powder diffraction peaks at 2Θ angles 9.1°, 10.9°, 12.4°, 13.8°, 14.8°, 16.0°, 17.4°, 18.0°, 18.5°, 21.2°, 22.9°, 24.1°, 24.5°, 27.8°, 30.0°. In another alternative crystalline Form B is characterized by x-ray powder diffraction peaks at 2Θ angles 8.5°, 9.1°, 10.9°, 12.4°, 13.8°, 14.6°, 14.8°, 15.7°, 16.0°, 17.4°, 18.0°, 18.2°, 18.5°, 20.4°, 21.2°, 22.1°, 22.6°, 22.9°, 23.5°, 24.1°, 24.5°, 25.2°, 25.7°, 25.9°, 26.8°, 27.1°, 27.8°, 28.8°, 29.4°, 29.7°, 30.0°, 31.1°, 31.6°, 32.3°, 33.5°, 34.0°, 35.2°, 35.7°, 36.8°, and 38.0°. In some embodiments, the peaks described above for crystalline Form B have a relative intensity of at least 10%, of at least 15%, of at least 20%, or of at least 25%.

Figure 5B:
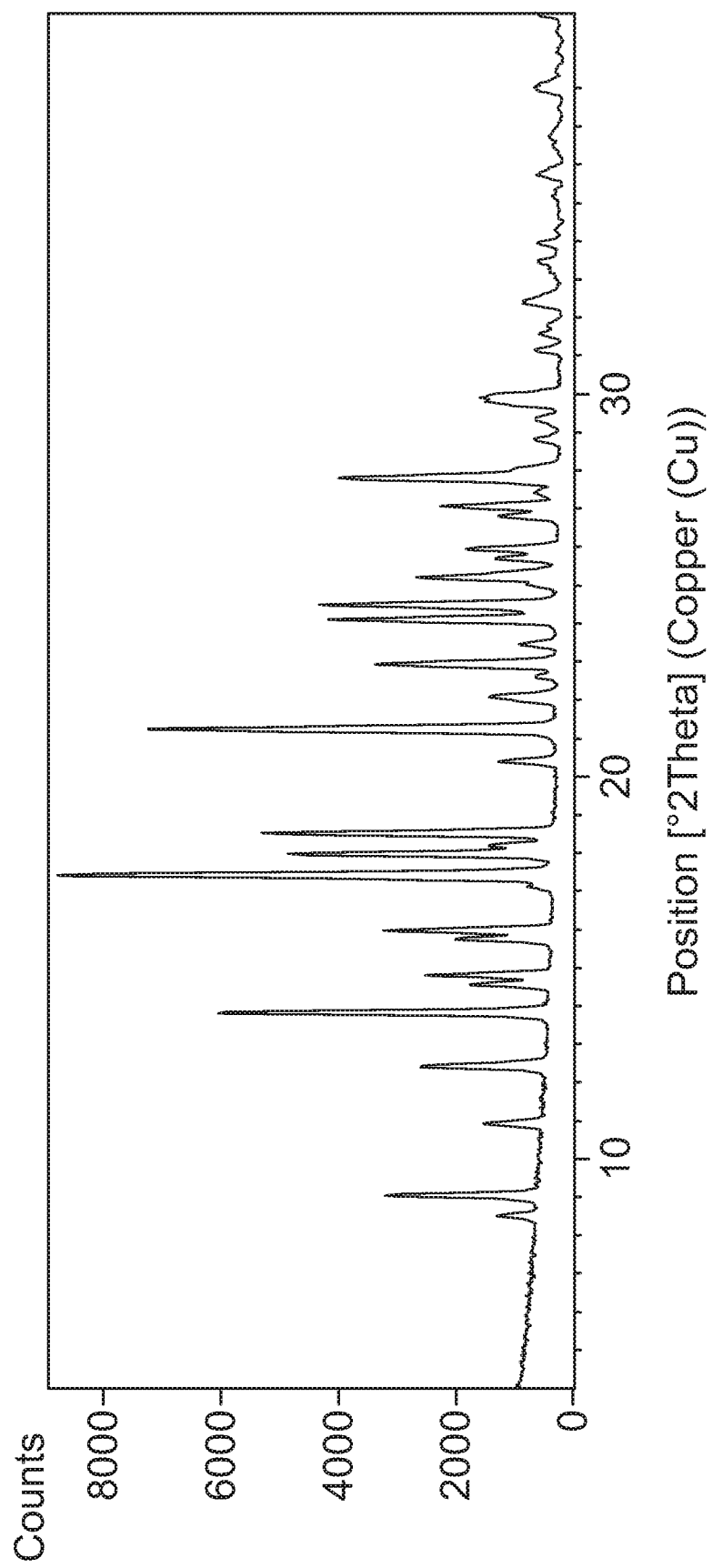
FIG. 5B depicts an X-ray powder diffraction pattern (XRPD) pattern of 8-(2-fluorobenzyl)-6-(3-(trifluoromethyl)-1H-1,2,4-triazol-5-yl)imidazo[1,2-a]pyrazine Form B, acquired at room temperature in reflection mode using a Panalytical Empyrean system.

In another aspect, crystalline Form B of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 5B.

In another aspect, crystalline Form B of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 2B.

Figure 6:
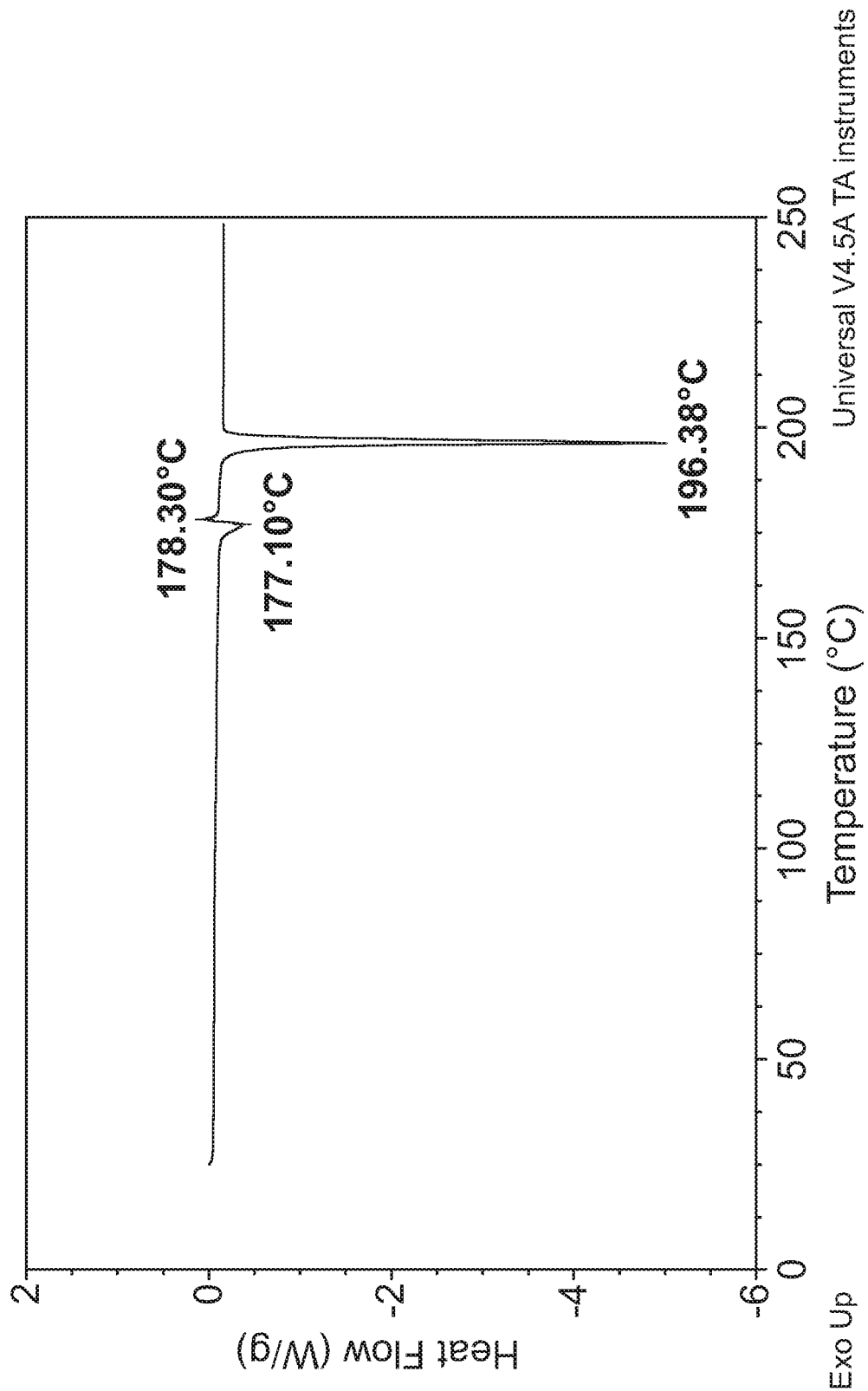
FIG. 6 depicts a DSC analysis of 8-(2-fluorobenzyl)-6-(3-(trifluoromethyl)-1H-1,2,4-triazol-5-yl)imidazo[1,2-a]pyrazine Form B.

In one aspect, crystalline Form B of 8-(2-fluorobenzyl)-6-(3-(trifluoromethyl)-1H-1,2,4-triazol-5-yl)imidazo[1,2-a]pyrazine has a DSC pattern that is substantially the same DSC pattern shown in FIG. 6. In particular, crystalline Form B is characterized by DSC phase transition temperature of 177°±2° C. and a melt at 195° C.±2° C.

Figure 7:
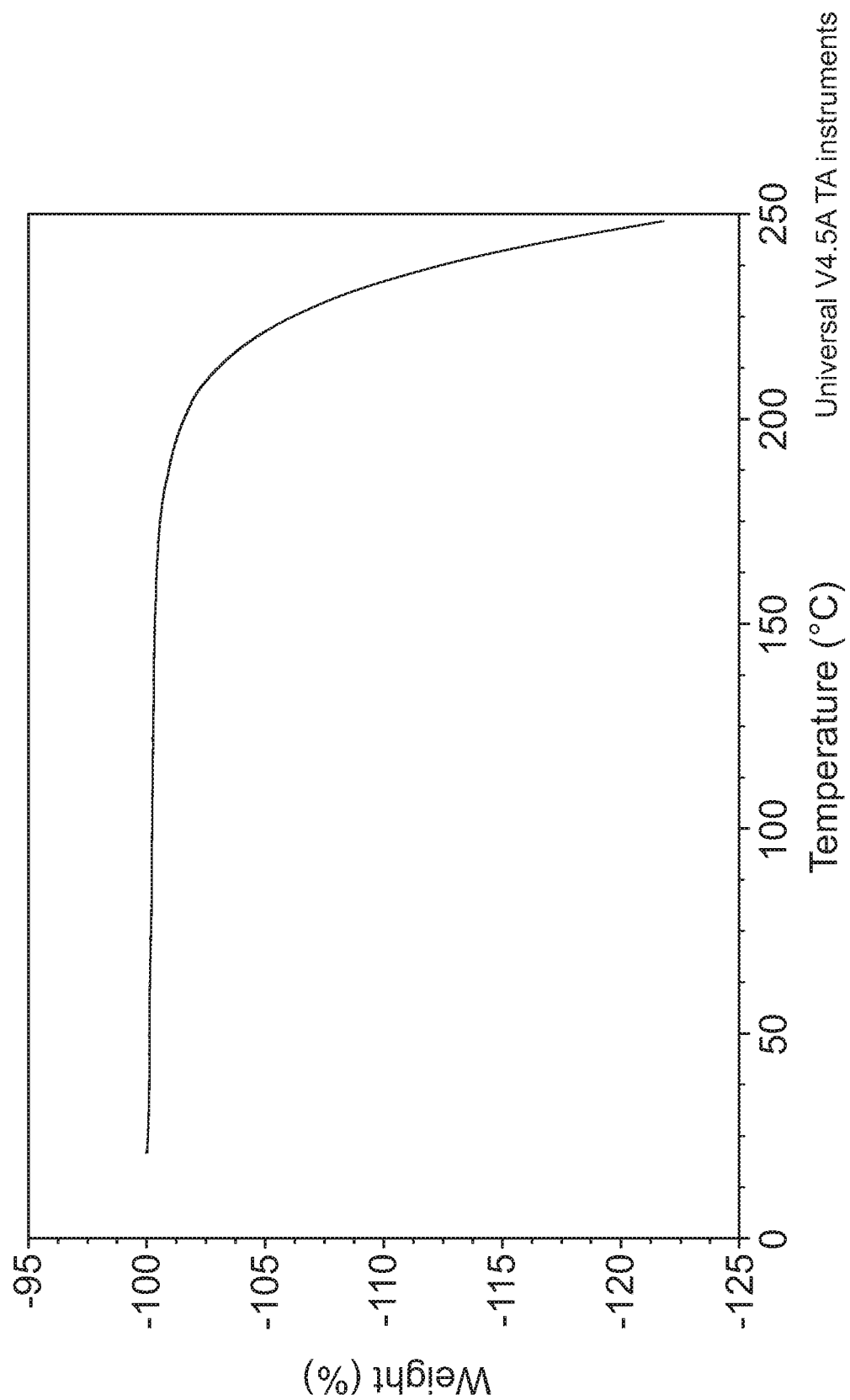
FIG. 7 depicts a TGA analysis of 8-(2-fluorobenzyl)-6-(3-(trifluoromethyl)-1H-1,2,4-triazol-5-yl)imidazo[1,2-a]pyrazine Form B.

In one aspect, crystalline Form B of 8-(2-fluorobenzyl)-6-(3-(trifluoromethyl)-1H-1,2,4-triazol-5-yl)imidazo[1,2-a]pyrazine has a TGA pattern that is substantially the same TGA pattern shown in FIG. 7.

In one aspect, the crystalline Form B of 8-(2-fluorobenzyl)-6-(3-(trifluoromethyl)-1H-1,2,4-triazol-5-yl)imidazo[1,2-a]pyrazine is characterized by at least three, at least four, or by at least five, x-ray powder diffraction peaks at 2Θ angles selected from 8.9°, 12.2°, 13.6°, 17.2°, and 21.0°; optionally together with one or both of the TGA, and DSC parameters recited above for Form B. Alternatively, crystalline Form B is characterized by at least three, at least four, at least five, at least six, at least seven, at least eight, at least nine, or at least ten x-ray powder diffraction peaks at 2Θ angles selected from 8.9°, 12.2°, 13.6°, 14.5°, 15.7°, 17.2°, 17.7°, 21.0°, 22.7°, 23.9°, 25.0°, 26.7°, and 27.6° optionally together with one or both of the TGA, and DSC parameters recited above for Form B.

In one aspect, the crystalline Form B of 8-(2-fluorobenzyl)-6-(3-(trifluoromethyl)-1H-1,2,4-triazol-5-yl)imidazo[1,2-a]pyrazine is characterized by at least three, at least four, or by at least five, x-ray powder diffraction peaks at 2Θ angles selected from 13.8°, 16.0°, 17.4°, 18.0°, 18.5°, and 21.2°; optionally together with one or both of the TGA, and DSC parameters recited above for Form B. Alternatively, crystalline Form B is characterized by at least three, at least four, at least five, at least six, at least seven, at least eight, at least nine, or at least ten x-ray powder diffraction peaks at 2Θ angles selected from 9.1°, 10.9°, 12.4°, 13.8°, 14.8°, 16.0°, 17.4°, 18.0°, 18.5°, 21.2°, 22.9°, 24.1°, 24.5°, 27.8°, 30.0°, optionally together with one or both of the TGA, and DSC parameters recited above for Form B.

In one aspect, the crystalline Form B of 8-(2-fluorobenzyl)-6-(3-(trifluoromethyl)-1H-1,2,4-triazol-5-yl)imidazo[1,2-a]pyrazine is characterized by at least three, at least four, at least five, at least six, at least seven, at least eight, or at least nine x-ray powder diffraction peaks at 2Θ angles selected from 8.9°, 12.2°, 13.6°, 14.5°, 15.7°, 17.2°, 21.0°, 22.7°, and 23.9°, optionally together with one or both of the TGA, and DSC parameters recited above for Form B.

In one aspect, crystalline Hydrate 1 of 8-(2-fluorobenzyl)-6-(3-(trifluoromethyl)-1H-1,2,4-triazol-5-yl)imidazo[1,2-a]pyrazine is characterized by x-ray powder diffraction pattern. The x-ray powder diffraction pattern can be acquired at room temperature in reflection mode using a Bruker D8 Discover system described herein. In one embodiment, crystalline Hydrate 1 is characterized by at least three, at least four, or at least five x-ray powder diffraction peaks at 2Θ angles selected from 11.5°, 15.2°, 17.0°, 17.7°, and 18.3°. Alternatively, crystalline Hydrate 1 of 8-(2-fluorobenzyl)-6-(3-(trifluoromethyl)-1H-1,2,4-triazol-5-yl)imidazo[1,2-a]pyrazine is characterized by at least three, or at least four x-ray powder diffraction peaks at 2Θ angles selected from 11.5°, 15.2°, 17.0°, and 18.3°. Alternatively, crystalline Hydrate 1 is characterized by at least three, at least four, at least five, at least six, at least seven, at least eight, at least nine, or at least ten x-ray powder diffraction peaks at 2Θ angles selected from 11.5°, 13.5°, 15.2°, 17.0°, 17.7°, 18.3°, 19.1°, 22.1°, 23.1°, 23.3°, 24.2°, 24.9°, and 29.4°. Alternatively, crystalline Hydrate 1 is characterized by x-ray powder diffraction peaks at 2Θ angles 11.5°, 13.5°, 15.2°, 17.0°, 17.7°, 18.3°, 19.1°, 22.1°, 23.1°, 23.3°, 24.2°, 24.9°, and 29.4°. Alternatively, crystalline Hydrate 1 is characterized by at least three, at least four, at least five, at least six, at least seven, at least eight, at least nine, or at least ten x-ray powder diffraction peaks at 2Θ angles selected from 11.5°, 13.5°, 17.0°, 17.7°, 18.3°, 22.1°, 23.1°, 23.3°, 24.2°, 24.9°, and 29.4°. Alternatively, crystalline Hydrate 1 is characterized by x-ray powder diffraction peaks at 2Θ angles 11.5°, 13.5°, 17.0°, 17.7°, 18.3°, 22.1°, 23.1°, 23.3°, 24.2°, 24.9°, and 29.4°. In another alternative crystalline Hydrate 1 is characterized by x-ray powder diffraction peaks at 2Θ angles 9.1°, 11.5°, 13.5°, 15.2°, 17.0°, 17.7°, 18.3°, 19.1°, 20.1°, 22.1°, 23.1°, 23.3°, 24.2°, 24.9°, 25.4°, 26.7°, 27.5°, 29.4°, 29.9°, 30.6°, and 33.5°. In some embodiments, the peaks described above for crystalline Hydrate 1 have a relative intensity of at least 10%, of at least 15%, of at least 20%, or of at least 25%.

Figure 8A:
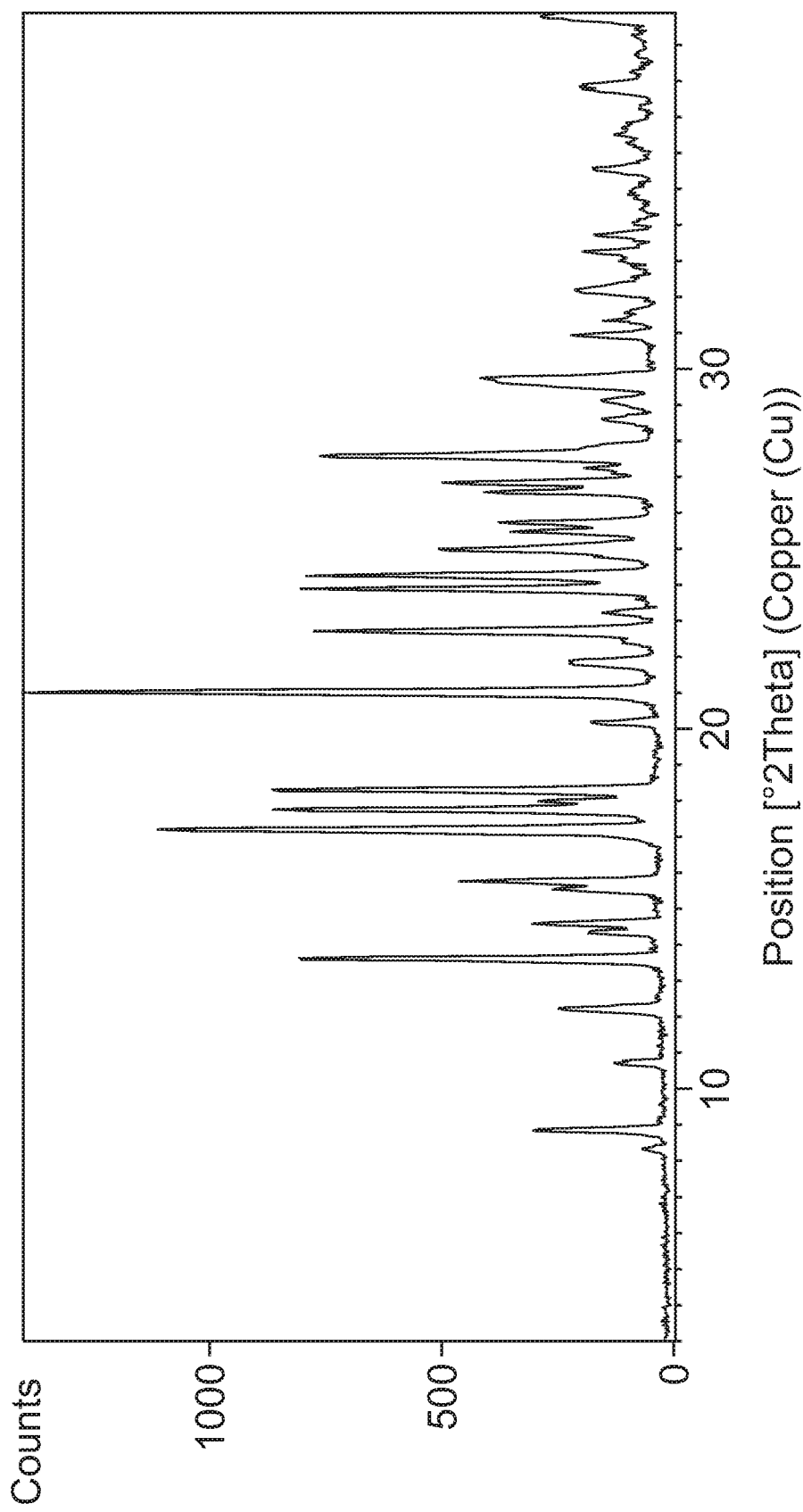
FIG. 8A depicts an XRPD pattern of 8-(2-fluorobenzyl)-6-(3-(trifluoromethyl)-1H-1,2,4-triazol-5-yl)imidazo[1,2-a]pyrazine Hydrate 1, acquired at room temperature in reflection mode using a Bruker D8 Discover system.

In another aspect, crystalline Hydrate 1 of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 8A.

In another aspect, crystalline Hydrate 1 of 8-(2-fluorobenzyl)-6-(3-(trifluoromethyl)-1H-1,2,4-triazol-5-yl)imidazo

[1,2-a]pyrazine has an XRPD pattern that substantially includes the peaks in Table 3A.

In one aspect, crystalline Hydrate 1 of 8-(2-fluorobenzyl)-6-(3-(trifluoromethyl)-1H-1,2,4-triazol-5-yl)imidazo[1,2-a]pyrazine is characterized by x-ray powder diffraction pattern, acquired at room temperature in reflection mode using a Panalytical Empyrean system described herein. In one embodiment, crystalline Hydrate 1 is characterized by at least three, at least four, or at least five x-ray powder diffraction peaks at 2Θ angles selected from 11.7°, 15.5°, 17.2°, 17.9°, 18.5°, 23.3°, and 25.1°. Alternatively, crystalline Hydrate 1 of 8-(2-fluorobenzyl)-6-(3-(trifluoromethyl)-1H-1,2,4-triazol-5-yl)imidazo[1,2-a]pyrazine is characterized by at least three, or at least four x-ray powder diffraction peaks at 2Θ angles selected from 11.7°, 15.5°, 17.2°, 17.9°, 18.5°, 23.3°, and 25.1° Alternatively, crystalline Hydrate 1 is characterized by at least three, at least four, at least five, at least six, at least seven, at least eight, at least nine, or at least ten x-ray powder diffraction peaks at 2Θ angles selected from 9.4°, 11.7°, 13.7°, 15.5°, 17.2°, 17.9°, 18.5°, 22.3°, 23.3°, 24.4°, 25.1°, 29.6°, and 30.1°. Alternatively, crystalline Hydrate 1 is characterized by x-ray powder diffraction peaks at 2Θ angles 9.4°, 11.7°, 13.7°, 15.5°, 17.2°, 17.9°, 18.5°, 22.3°, 23.3°, 24.4°, 25.1°, 29.6°, and 30.1°. In another alternative crystalline Hydrate 1 is characterized by x-ray powder diffraction peaks at 2Θ angles 8.8°, 9.4°, 11.7°, 12.2°, 13.7°, 14.0°, 15.5°, 16.7°, 17.2°, 17.9°, 18.5°, 19.4°, 20.3°, 21.4°, 22.3°, 23.3°, 23.6°, 24.4°, 25.1°, 25.6°, 27.0°, 27.7°, 28.6°, 29.6°, 30.1°, 30.9°, 32.2°, 33.6°, 34.0°, 35.0°, 37.6°, and 38.9°. In some embodiments, the peaks described above for crystalline Hydrate 1 have a relative intensity of at least 10%, of at least 15%, of at least 20%, or of at least 25%.

Figure 8B:
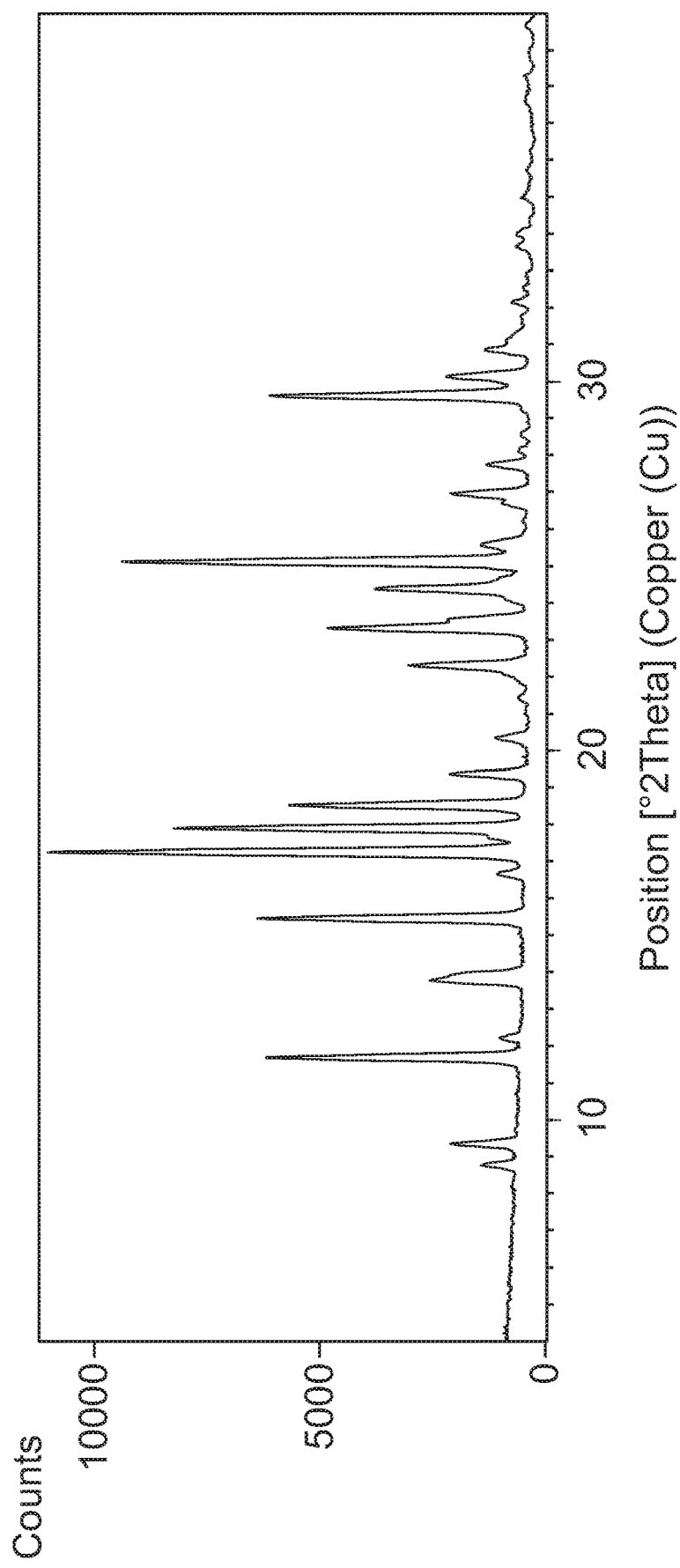
FIG. 8B depicts an X-ray powder diffraction pattern (XRPD) pattern of 8-(2-fluorobenzyl)-6-(3-(trifluoromethyl)-1H-1,2,4-triazol-5-yl)imidazo[1,2-a]pyrazine Hydrate 1, acquired at room temperature in reflection mode using a Panalytical Empyrean system.

In another aspect, crystalline Hydrate 1 of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 8B.

In another aspect, crystalline Hydrate 1 of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 3B.

Figure 9:
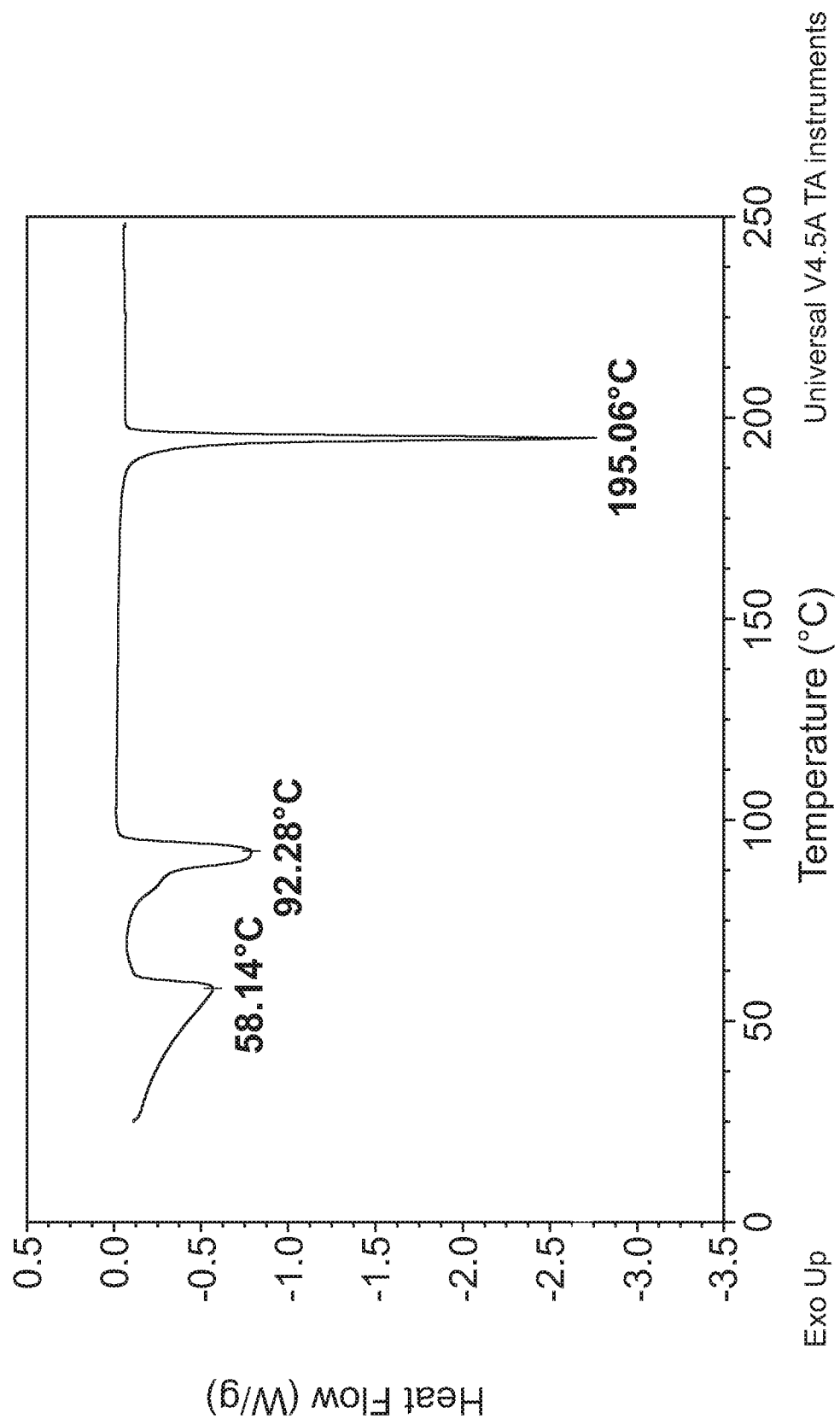
FIG. 9 depicts a DSC analysis of 8-(2-fluorobenzyl)-6-(3-(trifluoromethyl)-1H-1,2,4-triazol-5-yl)imidazo[1,2-a]pyrazine Hydrate 1.

In one aspect, crystalline Hydrate 1 of 8-(2-fluorobenzyl)-6-(3-(trifluoromethyl)-1H-1,2,4-triazol-5-yl)imidazo[1,2-a]pyrazine has a DSC pattern that is substantially the same DSC pattern shown in FIG. 9. In particular, crystalline Hydrate 1 is characterized by two endotherms in the DSC analysis at 58°±2° C., 92°±2° C., and a melt at 195° C.±2° C.

Figure 10:
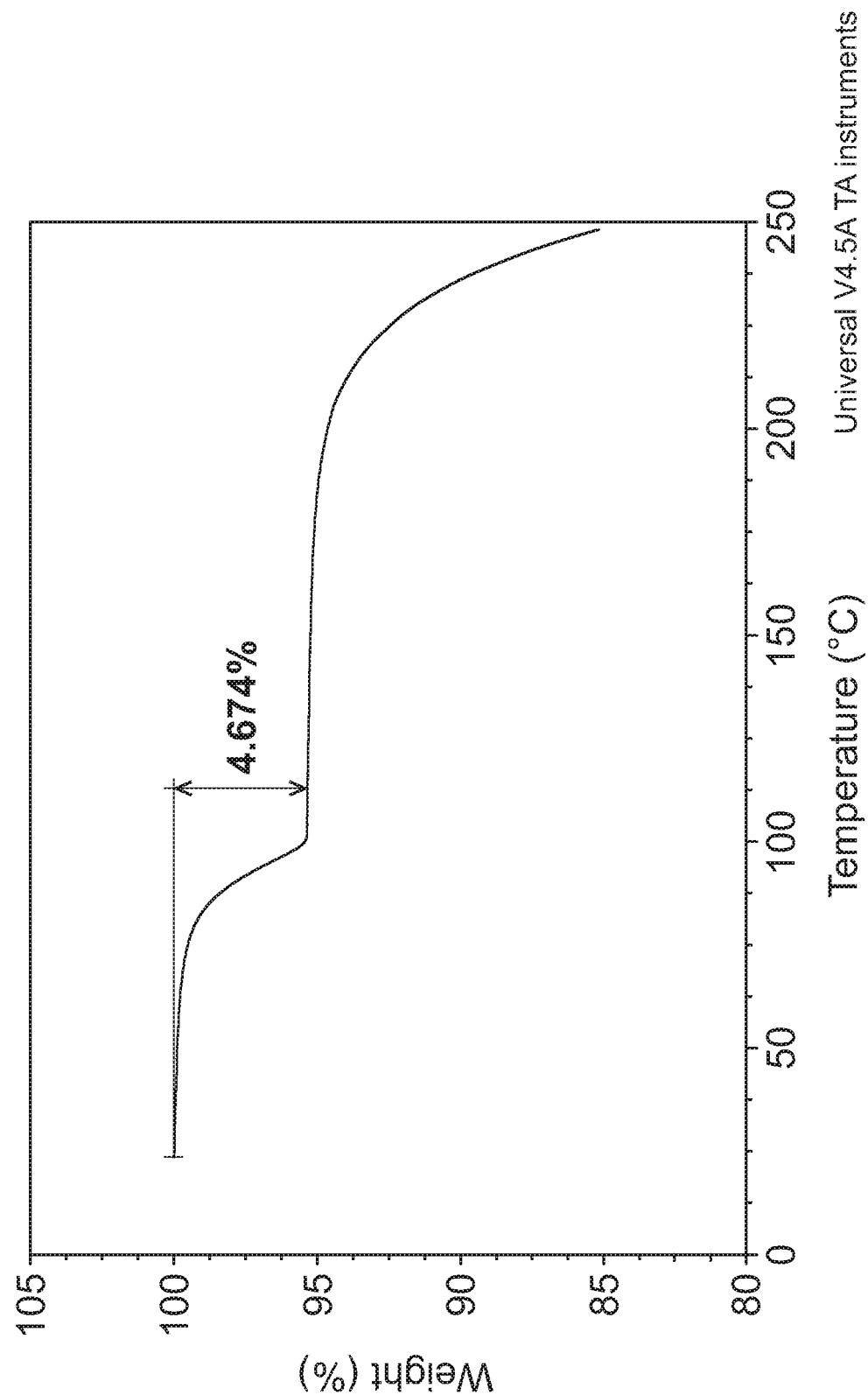
FIG. 10 depicts a TGA analysis of 8-(2-fluorobenzyl)-6-(3-(trifluoromethyl)-1H-1,2,4-triazol-5-yl)imidazo[1,2-a]pyrazine Hydrate 1.

In one aspect, crystalline Hydrate 1 of 8-(2-fluorobenzyl)-6-(3-(trifluoromethyl)-1H-1,2,4-triazol-5-yl)imidazo[1,2-a]pyrazine has a TGA pattern that is substantially the same TGA pattern shown in FIG. 10.

In one aspect, the crystalline Hydrate 1 of 8-(2-fluorobenzyl)-6-(3-(trifluoromethyl)-1H-1,2,4-triazol-5-yl)imidazo[1,2-a]pyrazine is characterized by at least three, at least four, or by at least five, x-ray powder diffraction peaks at 2Θ angles selected from 11.5°, 15.2°, 17.0°, 17.7°, and 18.3°; optionally together with one or both of the TGA, or DSC parameters recited above for Hydrate 1. Alternatively, crystalline Hydrate 1 is characterized by at least three, at least four, at least five, at least six, at least seven, at least eight, at least nine, or at least ten x-ray powder diffraction peaks at 2Θ angles selected from 11.5°, 13.5°, 15.2°, 17.0°, 17.7°, 18.3°, 19.1°, 22.1°, 23.1°, 23.3°, 24.2°, 24.9°, and 29.4° optionally together with one or both of the TGA, or DSC parameters recited above for Hydrate 1.

In one aspect, the crystalline Hydrate 1 of 8-(2-fluorobenzyl)-6-(3-(trifluoromethyl)-1H-1,2,4-triazol-5-yl)imidazo[1,2-a]pyrazine is characterized by at least three, at least four, or by at least five, x-ray powder diffraction peaks at 2Θ angles selected from 11.7°, 15.5°, 17.2°, 17.9°, 18.5°, 23.3°, and 25.1°; optionally together with one or both of the TGA, or DSC parameters recited above for Hydrate 1. Alternatively, crystalline Hydrate 1 is characterized by at least three, at least four, at least five, at least six, at least seven, at least eight, at least nine, or at least ten x-ray powder diffraction peaks at 2Θ angles selected from 9.4°, 11.7°, 13.7°, 15.5°, 17.2°, 17.9°, 18.5°, 22.3°, 23.3°, 24.4°, 25.1°, 29.6°, and 30.1°, optionally together with one or both of the TGA, or DSC parameters recited above for Hydrate 1.

In one aspect, the crystalline Hydrate 1 of 8-(2-fluorobenzyl)-6-(3-(trifluoromethyl)-1H-1,2,4-triazol-5-yl)imidazo[1,2-a]pyrazine is characterized by at least three, at least four, at least five, at least six, at least seven, at least eight, at least nine, or at least ten x-ray powder diffraction peaks at 2Θ angles selected from 11.5°, 13.5°, 17.0°, 17.7°, 18.3°, 22.1°, 23.1°, 23.3°, 24.2°, 24.9°, and 29.4°; optionally together with one or both of the TGA, or DSC parameters recited above for Hydrate 1. In one aspect, crystalline Hydrate 2 of 8-(2-fluorobenzyl)-6-(3-(trifluoromethyl)-1H-1,2,4-triazol-5-yl)imidazo[1,2-a]pyrazine is characterized by x-ray powder diffraction pattern. The x-ray powder diffraction pattern can be acquired at room temperature in reflection mode using a Bruker D8 Discover system described herein. In one embodiment, crystalline Hydrate 2 is characterized by at least three, at least four, or at least five x-ray powder diffraction peaks at 2Θ angles selected from 10.4°, 15.5°, 18.4°, 18.7°, and 21.9°. Alternatively, crystalline Hydrate 2 of 8-(2-fluorobenzyl)-6-(3-(trifluoromethyl)-1H-1,2,4-triazol-5-yl)imidazo[1,2-a]pyrazine is characterized at least three, or at least four x-ray powder diffraction peaks at 2Θ angles selected from 10.4°, 15.5°, 18.4°, and 18.7°. Alternatively, crystalline Hydrate 2 is characterized by at least three, at least four, at least five, at least six, at least seven, at least eight, at least nine, or at least ten x-ray powder diffraction peaks at 2Θ angles selected from 10.4°, 15.5°, 18.4°, 18.7°, 20.7°, 21.2°, 21.9°, 22.7°, 24.6°, 25.9°, 26.3°, and 27.4°. Alternatively, crystalline Hydrate 2 is characterized by x-ray powder diffraction peaks at 2Θ angles 10.4°, 15.5°, 18.4°, 18.7°, 20.7°, 21.2°, 21.9°, 22.7°, 24.6°, 25.9°, 26.3°, and 27.4°. Alternatively, crystalline Hydrate 2 is characterized by at least three, at least four, or at least five x-ray powder diffraction peaks at 2Θ angles selected from 10.4°, 18.7°, 21.2°, 24.6°, and 27.4°. Alternatively, crystalline Hydrate 2 is characterized by x-ray powder diffraction peaks at 2Θ angles 10.4°, 18.7°, 21.2°, 24.6°, and 27.4°. In another alternative crystalline Hydrate 2 is characterized by x-ray powder diffraction peaks at 2Θ angles 9.0°, 10.4°, 14.9°, 15.5°, 17.8°, 18.4°, 18.7°, 20.7°, 21.2°, 21.9°, 22.7°, 24.6°, 25.9°, 26.3°, 27.4°, 28.0°, 29.5°, 31.0°, 31.7°, 32.6°, and 34.5°. In some embodiments, the peaks described above for crystalline Hydrate 2 have a relative intensity of at least 10%, of at least 15%, of at least 20%, or of at least 25%.

Figure 11A:
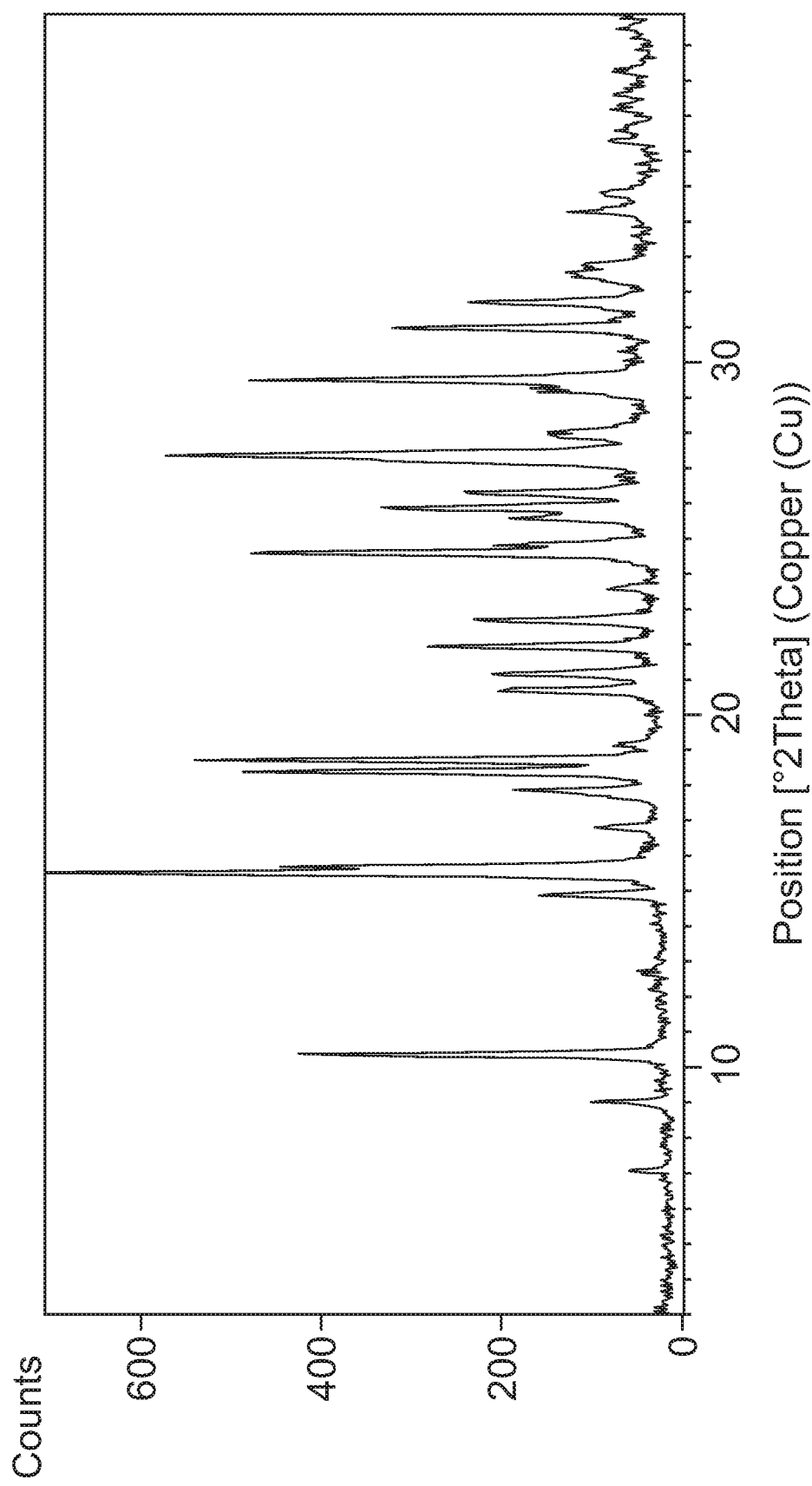
FIG. 11A is an XRPD pattern of 8-(2-fluorobenzyl)-6-(3-(trifluoromethyl)-1H-1,2,4-triazol-5-yl)imidazo[1,2-a]pyrazine Hydrate 2, acquired at room temperature in reflection mode using a Bruker D8 Discover system.

In another aspect, crystalline Hydrate 2 of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 11A.

In another aspect, crystalline Hydrate 2 of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 4A.

In one aspect, crystalline Hydrate 2 of 8-(2-fluorobenzyl)-6-(3-(trifluoromethyl)-1H-1,2,4-triazol-5-yl)imidazo[1,2-a]

pyrazine is characterized by x-ray powder diffraction pattern, acquired at room temperature in reflection mode using a Panalytical Empyrean system described herein. In one embodiment, crystalline Hydrate 2 is characterized by at least three, at least four, or at least five x-ray powder diffraction peaks at 2Θ angles selected from 7.3°, 10.6°, 15.8°, 15.9°, and 27.6°. Alternatively, crystalline Hydrate 2 of 8-(2-fluorobenzyl)-6-(3-(trifluoromethyl)-1H-1,2,4-triazol-5-yl)imidazo[1,2-a]pyrazine is characterized at least three, or at least four x-ray powder diffraction peaks at 2Θ angles selected from 7.3°, 10.6°, 15.8°, 15.9°, and 27.6°. Alternatively, crystalline Hydrate 2 is characterized by at least three, at least four, at least five, at least six, at least seven, at least eight, at least nine, or at least ten x-ray powder diffraction peaks at 2Θ angles selected from 7.3°, 10.6°, 15.2°, 15.8°, 15.9°, 18.1°, 18.7°, 19.0°, 23.0°, 24.8°, 25.1°, 26.6°, 27.6°, and 29.8°. Alternatively, crystalline Hydrate 2 is characterized by x-ray powder diffraction peaks at 2Θ angles 7.3°, 10.6°, 15.2°, 15.8°, 15.9°, 18.1°, 18.7°, 19.0°, 23.0°, 24.8°, 25.1°, 26.6°, 27.6°, and 29.8°. In another alternative crystalline Hydrate 2 is characterized by x-ray powder diffraction peaks at 2Θ angles 7.3°, 9.3°, 10.6°, 13.2°, 15.2°, 15.8°, 15.9°, 17.1°, 18.1°, 18.7°, 19.0°, 21.0°, 21.5°, 22.2°, 23.0°, 23.8°, 24.8°, 25.1°, 26.2°, 26.6°, 27.6°, 29.8°, 31.2°, 32.0°, 32.8°, 34.6°, 35.1°, and 36.9°. In some embodiments, the peaks described above for crystalline Hydrate 2 have a relative intensity of at least 10%, of at least 15%, of at least 20%, or of at least 25%.

Figure 11B:
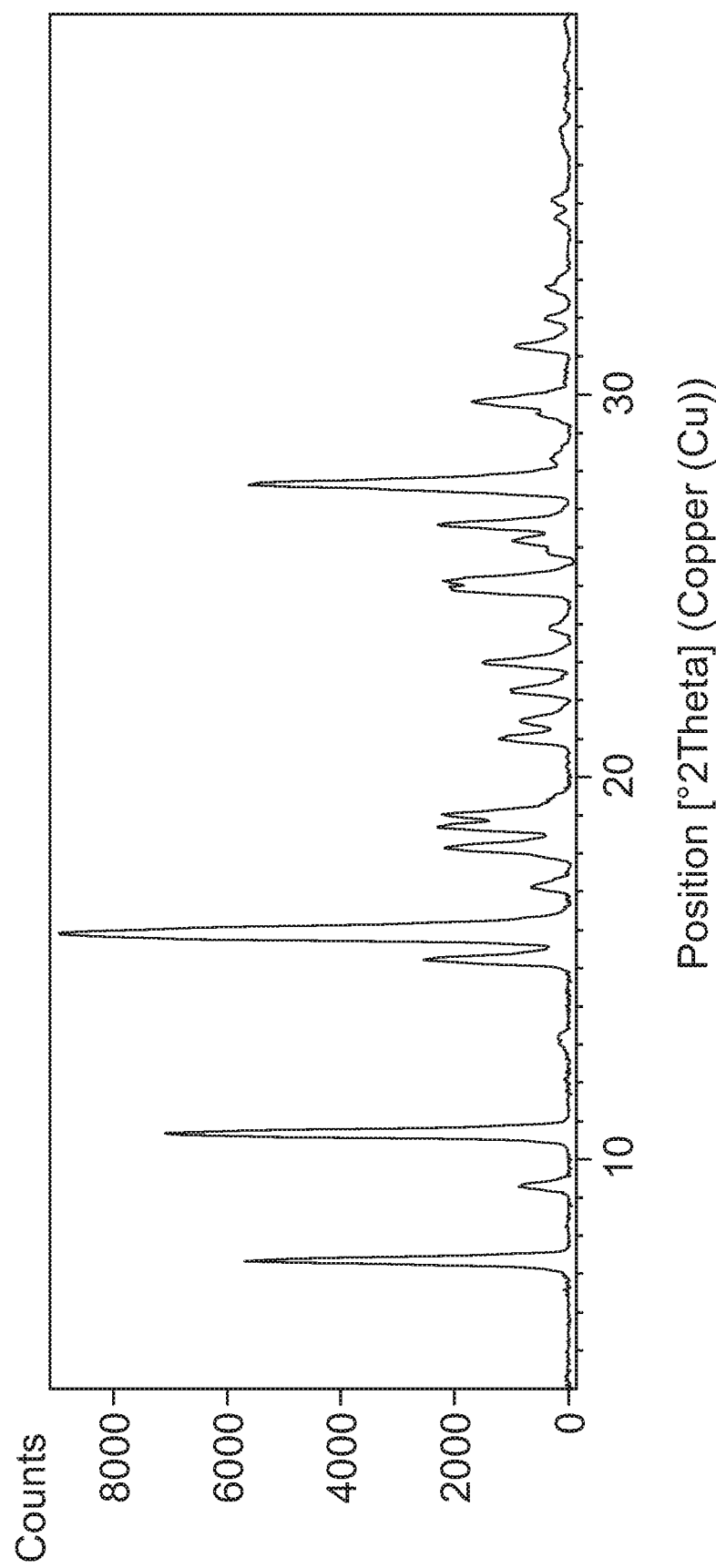
FIG. 11B depicts an X-ray powder diffraction pattern (XRPD) pattern of 8-(2-fluorobenzyl)-6-(3-(trifluoromethyl)-1H-1,2,4-triazol-5-yl)imidazo[1,2-a]pyrazine Hydrate 2, acquired at room temperature in reflection mode using a Panalytical Empyrean system.

In another aspect, crystalline Hydrate 2 of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 11B.

In another aspect, crystalline Hydrate 2 of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 4B.

Figure 12:
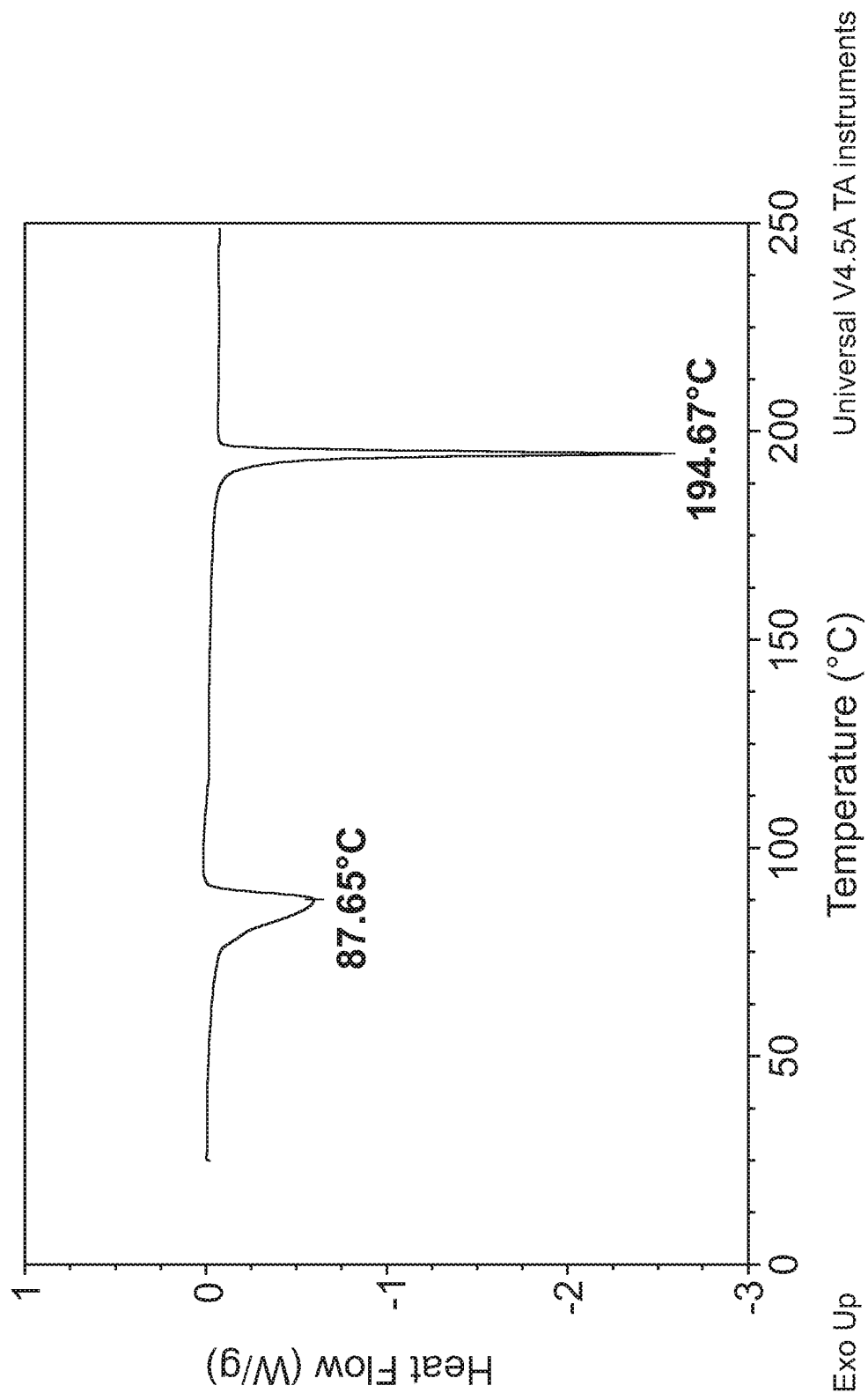
FIG. 12 is a DSC analysis of 8-(2-fluorobenzyl)-6-(3-(trifluoromethyl)-1H-1,2,4-triazol-5-yl)imidazo[1,2-a]pyrazine Hydrate 2.

In one aspect, crystalline Hydrate 2 of 8-(2-fluorobenzyl)-6-(3-(trifluoromethyl)-1H-1,2,4-triazol-5-yl)imidazo[1,2-a]pyrazine has a DSC pattern that is substantially the same DSC pattern shown in FIG. 12. In particular, crystalline Hydrate 2 is characterized by DSC an endotherm at 87°±2° C., and a melt at 195° C.±2° C.

Figure 13:
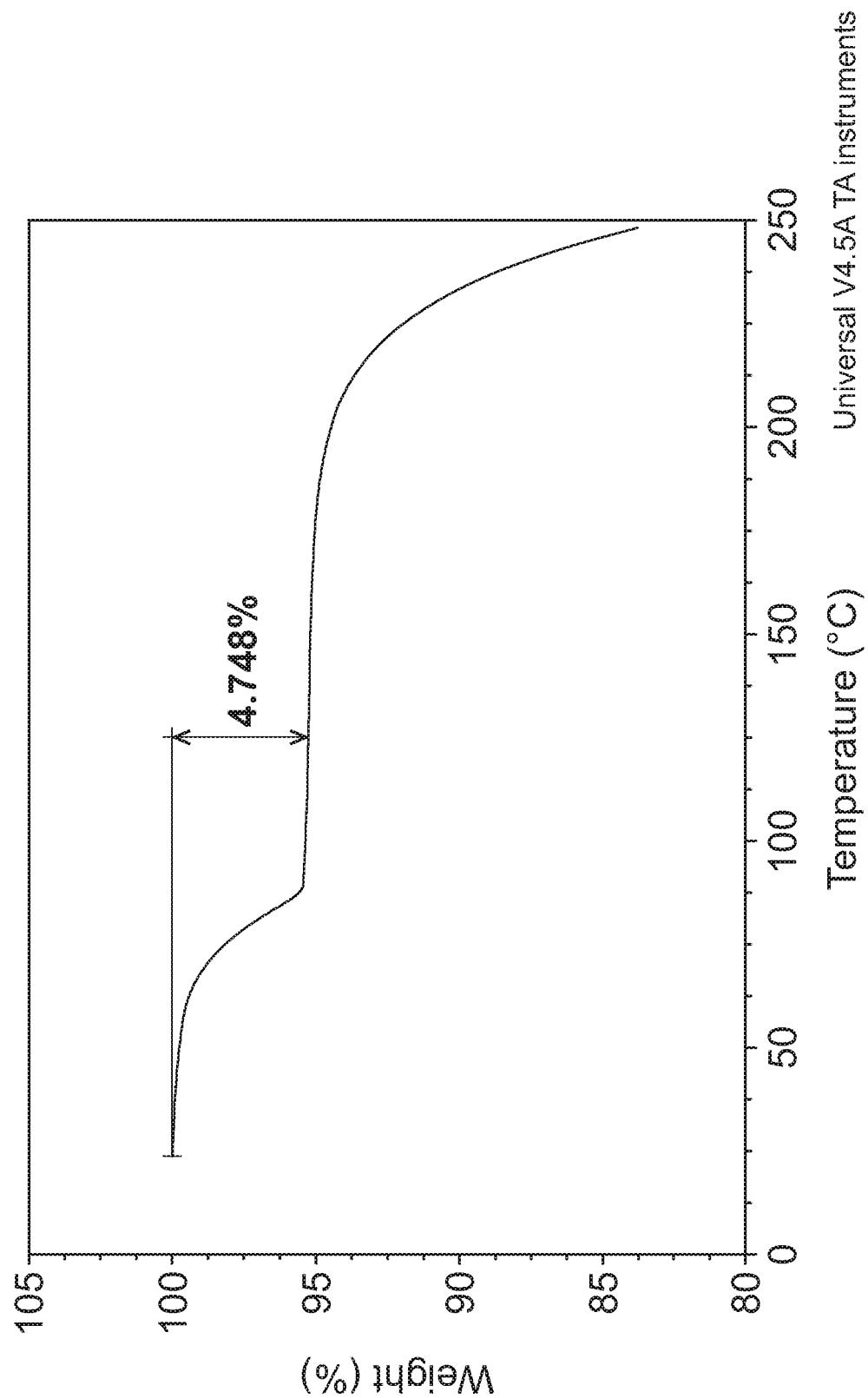
FIG. 13 is a TGA analysis of 8-(2-fluorobenzyl)-6-(3-(trifluoromethyl)-1H-1,2,4-triazol-5-yl)imidazo[1,2-a]pyrazine Hydrate 2.

In one aspect, crystalline Hydrate 2 of 8-(2-fluorobenzyl)-6-(3-(trifluoromethyl)-1H-1,2,4-triazol-5-yl)imidazo[1,2-a]pyrazine has a TGA pattern that is substantially the same TGA pattern shown in FIG. 13.

In one aspect, the crystalline Hydrate 2 of 8-(2-fluorobenzyl)-6-(3-(trifluoromethyl)-1H-1,2,4-triazol-5-yl)imidazo[1,2-a]pyrazine is characterized by at least three, at least four, or by at least five, x-ray powder diffraction peaks at 2Θ angles selected from 10.4°, 15.5°, 17.8°, 18.4°, and 18.7°; optionally together with one or both of the TGA, or DSC parameters recited above for Hydrate 2. Alternatively, crystalline Hydrate 2 is characterized by at least three, at least four, at least five, at least six, at least seven, at least eight, at least nine, or at least ten x-ray powder diffraction peaks at 2Θ angles selected from 10.4°, 15.5°, 18.4°, 18.7°, 20.7°, 21.2°, 21.9°, 22.7°, 24.6°, 25.9°, 26.3°, and 27.4° optionally together with one or both of the TGA, or DSC parameters recited above for Hydrate 2.

In one aspect, the crystalline Hydrate 2 of 8-(2-fluorobenzyl)-6-(3-(trifluoromethyl)-1H-1,2,4-triazol-5-yl)imidazo[1,2-a]pyrazine is characterized by at least three, at least four, or by at least five, x-ray powder diffraction peaks at 2Θ angles selected from 7.3°, 10.6°, 15.8°, 15.9°, and 27.6°; optionally together with one or both of the TGA, or DSC parameters recited above for Hydrate 2. Alternatively, crystalline Hydrate 2 is characterized by at least three, at least four, at least five, at least six, at least seven, at least eight, at least nine, or at least ten x-ray powder diffraction peaks at 2Θ angles selected from 7.3°, 10.6°, 15.2°, 15.8°, 15.9°, 18.1°, 18.7°, 19.0°, 23.0°, 24.8°, 25.1°, 26.6°, 27.6°, and 29.8°, optionally together with one or both of the TGA, or DSC parameters recited above for Hydrate 2.

In one aspect, the crystalline Hydrate 2 of 8-(2-fluorobenzyl)-6-(3-(trifluoromethyl)-1H-1,2,4-triazol-5-yl)imidazo[1,2-a]pyrazine is characterized by at least three, at least four, or by at least five, x-ray powder diffraction peaks at 2Θ angles selected from 10.4°, 18.7°, 21.2°, 24.6°, and 27.4°; optionally together with one or both of the TGA, or DSC parameters recited above for Hydrate 2. In one aspect, crystalline Hydrate 3 of 8-(2-fluorobenzyl)-6-(3-(trifluoromethyl)-1H-1,2,4-triazol-5-yl)imidazo[1,2-a]pyrazine is characterized by x-ray powder diffraction pattern. The x-ray powder diffraction pattern can be acquired at room temperature in reflection mode using a Bruker D8 Discover system described herein. In one embodiment, crystalline Hydrate 3 is characterized by at least three, at least four, or at least five x-ray powder diffraction peaks at 2Θ angles selected from 10.3°, 12.1°, 13.5°, 16.9°, and 24.4°. Alternatively, crystalline Hydrate 3 is characterized by at least three, at least four, at least five, at least six, at least seven, at least eight, at least nine, or at least ten x-ray powder diffraction peaks at 2Θ angles selected from 10.3°, 12.1°, 13.5°, 15.9°, 16.9°, 17.6°, 22.0°, 22.9°, 24.4°, and 28.9°. Alternatively, crystalline Hydrate 3 is characterized by x-ray powder diffraction peaks at 2Θ angles 10.3°, 12.1°, 13.5°, 15.9°, 16.9°, 17.6°, 22.0°, 22.9°, 24.4°, and 28.9°. Alternatively, crystalline Hydrate 3 is characterized by at least three, or at least four x-ray powder diffraction peaks at 2Θ angles selected from 10.3°, 12.1°, 17.6°, and 22.0°. Alternatively, crystalline Hydrate 3 is characterized by x-ray powder diffraction peaks at 2Θ angles 10.3°, 12.1°, 17.6°, and 22.0°. In another alternative crystalline Hydrate 3 is characterized by x-ray powder diffraction peaks at 2Θ angles 8.5°, 10.3°, 12.1°, 13.5°, 14.5°, 15.9°, 16.9°, 17.6°, 18.5°, 20.3°, 21.0°, 22.0°, 22.9°, 24.4°, 25.0°, 26.6°, 28.9°, 30.8°, 33.0°, and 36.0°. In some embodiments, the peaks described above for crystalline Hydrate 3 have a relative intensity of at least 10%, of at least 15%, of at least 20%, or of at least 25%.

Figure 14A:
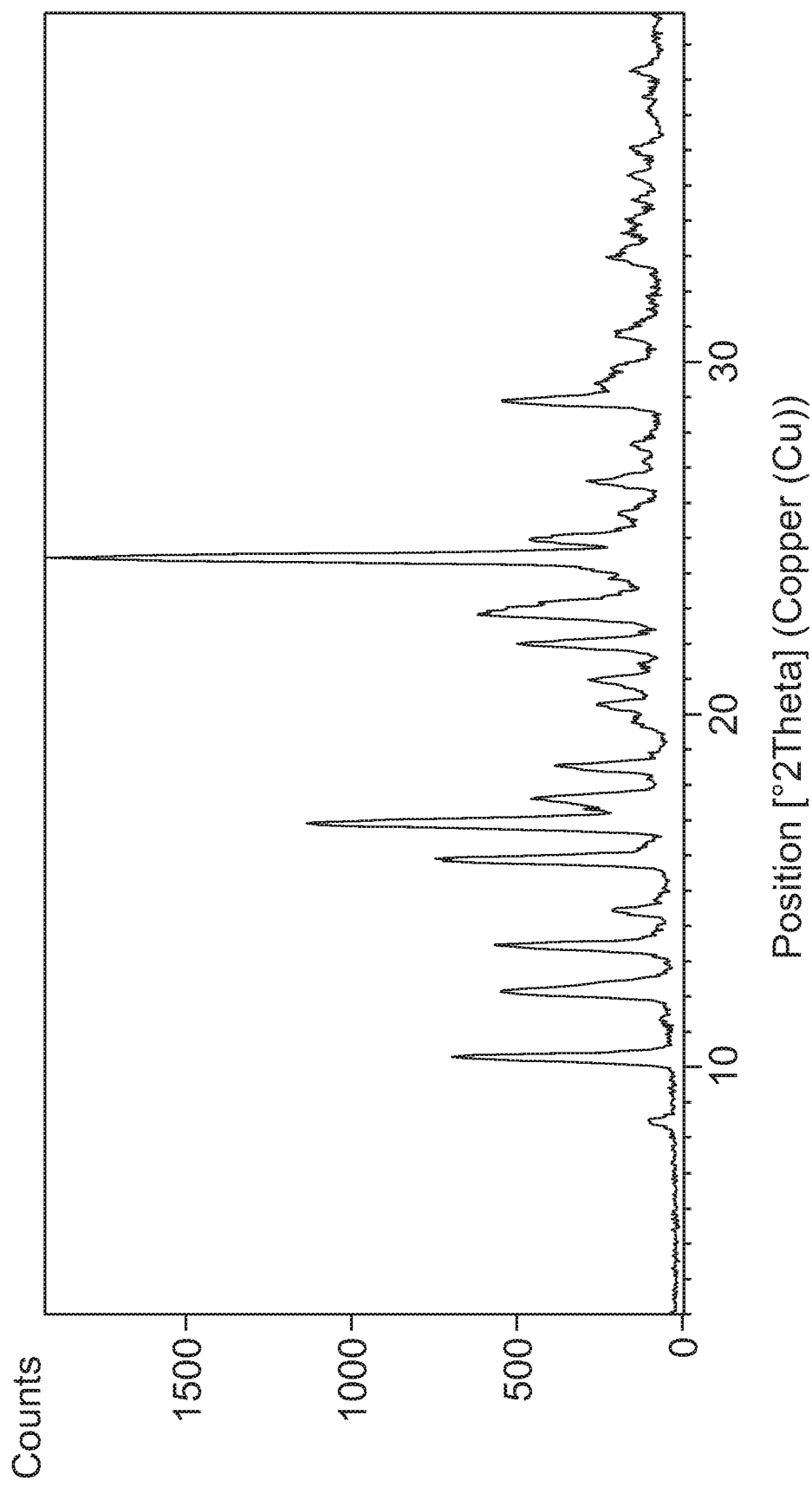
FIG. 14A is a XRPD pattern of 8-(2-fluorobenzyl)-6-(3-(trifluoromethyl)-1H-1,2,4-triazol-5-yl)imidazo[1,2-a]pyrazine Hydrate 3, acquired at room temperature in reflection mode using a Bruker D8 Discover system.

In another aspect, crystalline Hydrate 3 of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 14A.

In another aspect, crystalline Hydrate 3 of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 5A.

In one aspect, crystalline Hydrate 3 of 8-(2-fluorobenzyl)-6-(3-(trifluoromethyl)-1H-1,2,4-triazol-5-yl)imidazo[1,2-a]pyrazine is characterized by x-ray powder diffraction pattern, acquired at room temperature in reflection mode using a Panalytical Empyrean system described herein. In one embodiment, crystalline Hydrate 3 is characterized by at least three, at least four, or at least five x-ray powder diffraction peaks at 2Θ angles selected from 10.5°, 13.9°, 15.0°, 16.5°, 17.2°, and 17.6°. Alternatively, crystalline Hydrate 3 is characterized by at least three, at least four, at least five, at least six, at least seven, at least eight, at least nine, or at least ten x-ray powder diffraction peaks at 2Θ angles selected from 10.5°, 13.9°, 15.0°, 16.5°, 17.2°, 17.6°, 18.3°, 19.1°, 20.3°, 23.7°, and 30.1°. Alternatively, crystalline Hydrate 3 is characterized by x-ray powder diffraction peaks at 2Θ angles 10.5°, 13.9°, 15.0°, 16.5°, 17.2°, 17.6°, 18.3°, 19.1°, 20.3°, 23.7°, and 30.1°. In another alternative crystalline Hydrate 3 is characterized by x-ray powder diffraction peaks at 2Θ angles 8.3°, 8.7°, 10.5°, 12.0°, 12.8°, 13.9°, 14.5°, 15.0°, 16.5°, 17.2°, 17.6°, 18.3°, 19.1°, 20.3°, 21.1°, 21.6°, 22.2°, 22.6°, 23.7°, 24.1°, 24.7°, 25.0°, 25.6°, 26.2°, 27.7°, 28.5°, 30.1°, 31.9°, 34.1°, 35.0°, 35.6°, 37.1°, and 38.8°. In some embodiments, the peaks described above for crystalline Hydrate 3 have a relative intensity of at least 10%, of at least 15%, of at least 20%, or of at least 25%.

Figure 14B:
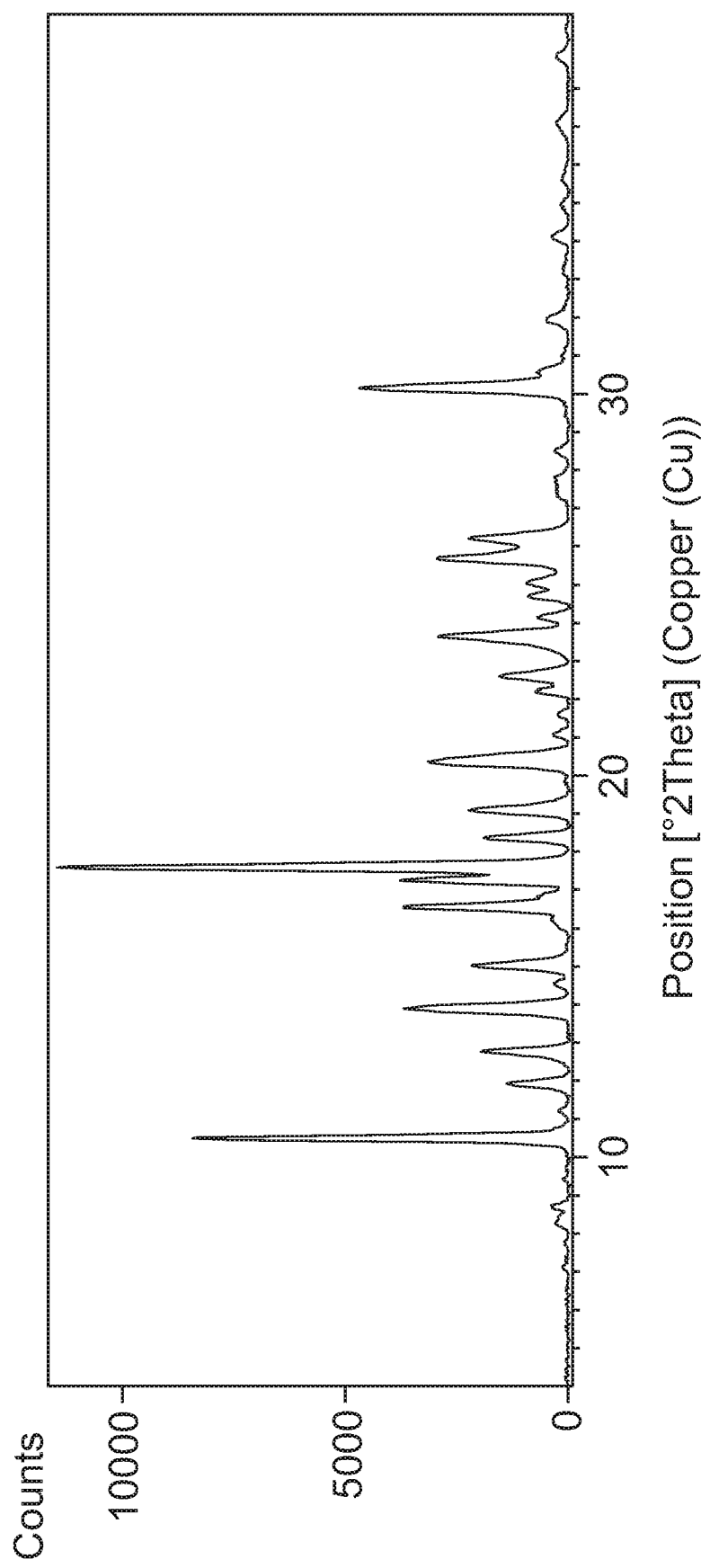
FIG. 14B depicts an X-ray powder diffraction pattern (XRPD) pattern of 8-(2-fluorobenzyl)-6-(3-(trifluoromethyl)-1H-1,2,4-triazol-5-yl)imidazo[1,2-a]pyrazine Hydrate 3, acquired at room temperature in reflection mode using a Panalytical Empyrean system.

In another aspect, crystalline Hydrate 3 of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 14B.

In another aspect, crystalline Hydrate 3 of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 5B.

Figure 15:
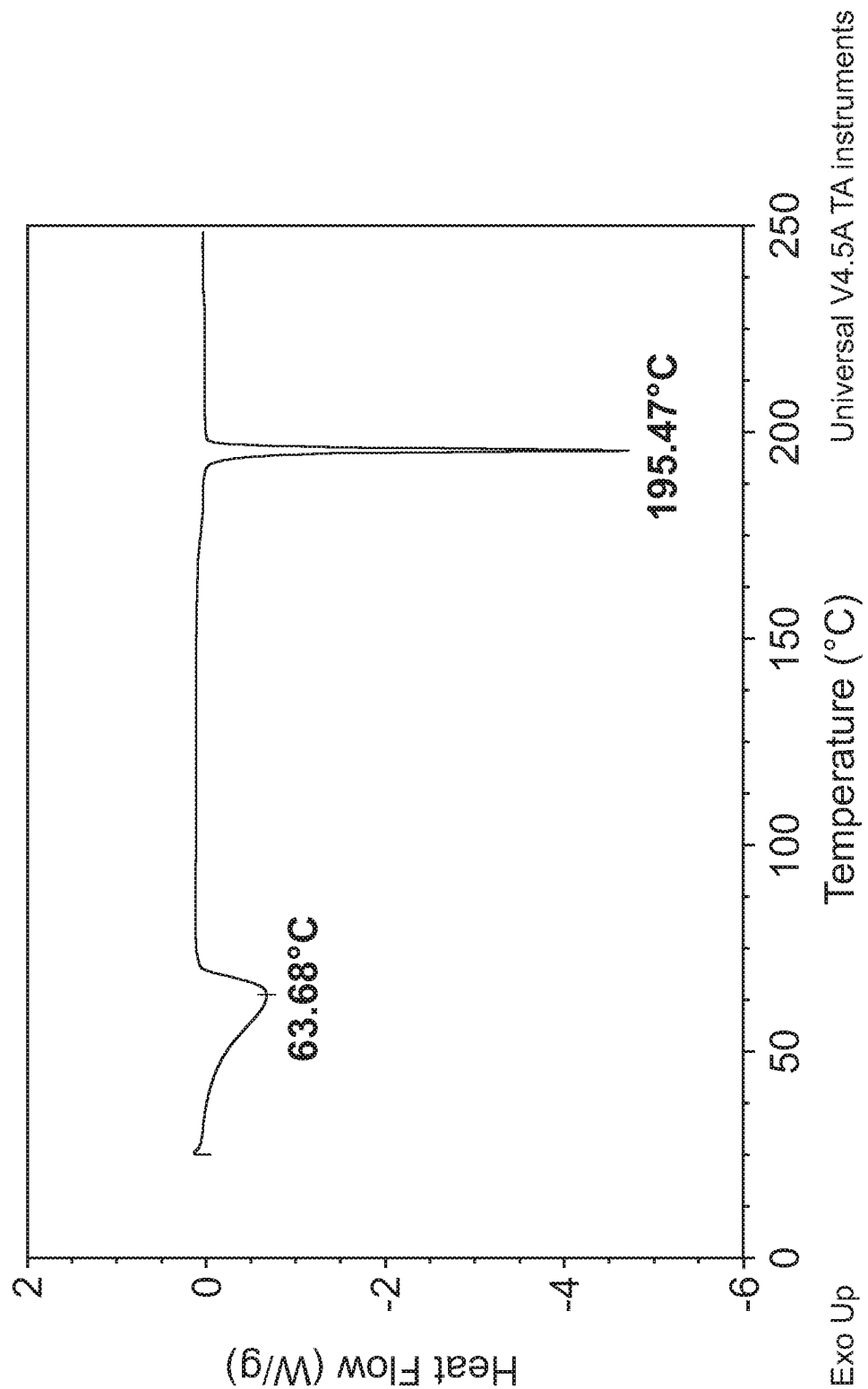
FIG. 15 is a DSC analysis of 8-(2-fluorobenzyl)-6-(3-(trifluoromethyl)-1H-1,2,4-triazol-5-yl)imidazo[1,2-a]pyrazine Hydrate 3.

In one aspect, crystalline Hydrate 3 of 8-(2-fluorobenzyl)-6-(3-(trifluoromethyl)-1H-1,2,4-triazol-5-yl)imidazo[1,2-a]pyrazine has a DSC pattern that is substantially the same DSC pattern shown in FIG. 15. In particular, crystalline Hydrate 3 is characterized by an endotherm at 64°±2° C., and a melt at 195° C.±2° C.

Figure 16:
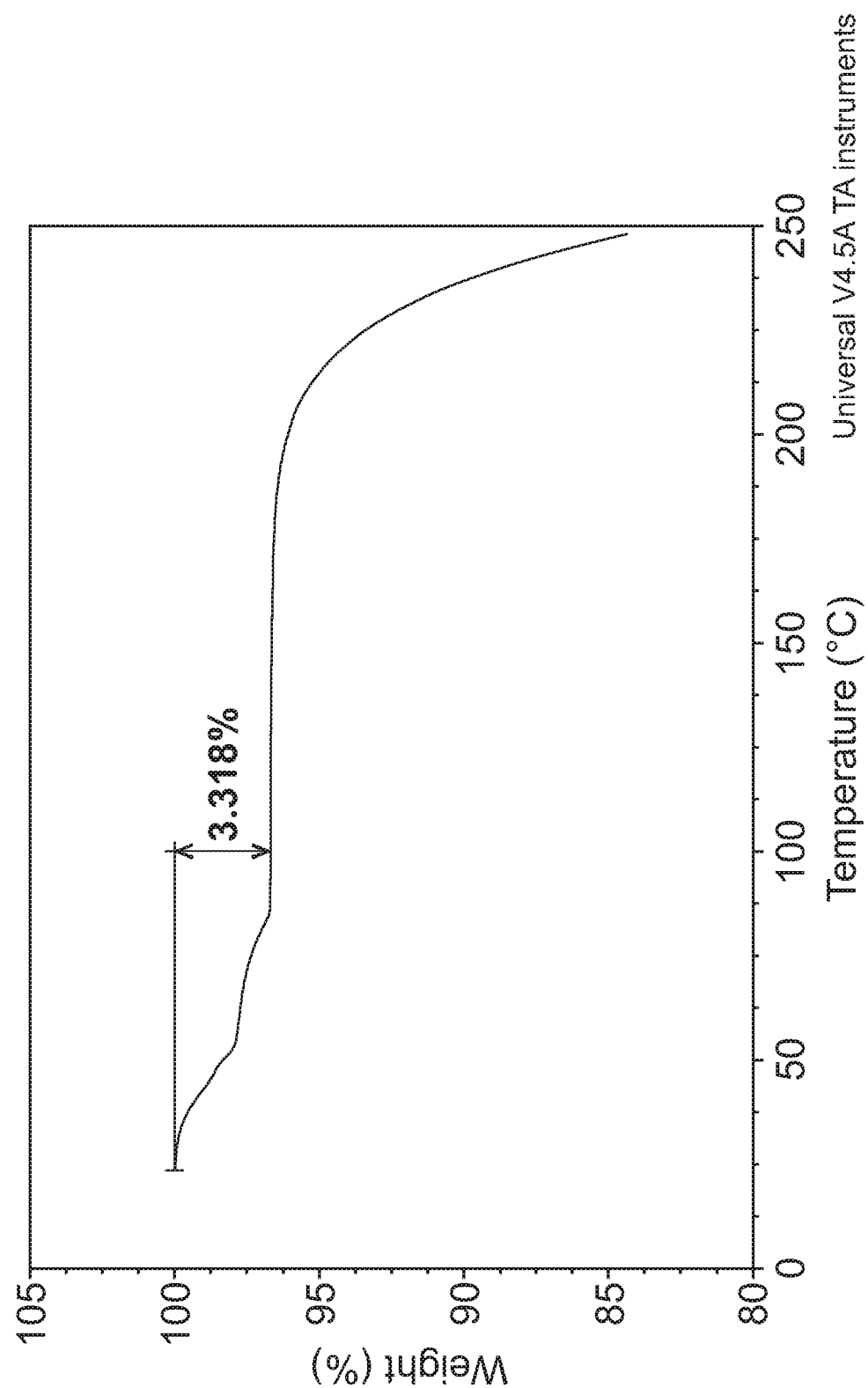
FIG. 16 is a TGA analysis of 8-(2-fluorobenzyl)-6-(3-(trifluoromethyl)-1H-1,2,4-triazol-5-yl)imidazo[1,2-a]pyrazine Hydrate 3.

In one aspect, crystalline Hydrate 3 of 8-(2-fluorobenzyl)-6-(3-(trifluoromethyl)-1H-1,2,4-triazol-5-yl)imidazo[1,2-a]pyrazine has a TGA pattern that is substantially the same TGA pattern shown in FIG. 16.

In one aspect, the crystalline Hydrate 3 of 8-(2-fluorobenzyl)-6-(3-(trifluoromethyl)-1H-1,2,4-triazol-5-yl)imidazo[1,2-a]pyrazine is characterized by at least three, at least four, or by at least five, x-ray powder diffraction peaks at 2Θ angles selected from 10.3°, 12.1°, 13.5°, 16.9°, and 24.4°; optionally together with one or both of the TGA, and DSC parameters recited above for Hydrate 3. Alternatively, crystalline Hydrate 3 is characterized by at least three, at least four, at least five, at least six, at least seven, at least eight, at least nine, or at least ten x-ray powder diffraction peaks at 2Θ angles selected from 10.3°, 12.1°, 13.5°, 15.9°, 16.9°, 17.6°, 22.0°, 22.9°, 24.4°, and 28.9° optionally together with one or both of the TGA, and DSC parameters recited above for Hydrate 3.

In one aspect, the crystalline Hydrate 3 of 8-(2-fluorobenzyl)-6-(3-(trifluoromethyl)-1H-1,2,4-triazol-5-yl)imidazo[1,2-a]pyrazine is characterized by at least three, at least four, or by at least five, x-ray powder diffraction peaks at 2Θ angles selected from 10.5°, 13.9°, 15.0°, 16.5°, 17.2°, and 17.6°, optionally together with one or both of the TGA, and DSC parameters recited above for Hydrate 3. Alternatively, crystalline Hydrate 3 is characterized by at least three, at least four, at least five, at least six, at least seven, at least eight, at least nine, or at least ten x-ray powder diffraction peaks at 2Θ angles selected from 10.5°, 13.9°, 15.0°, 16.5°, 17.2°, 17.6°, 18.3°, 19.1°, 20.3°, 23.7°, and 30.1°, optionally together with one or both of the TGA, and DSC parameters recited above for Hydrate 3.

In one aspect, the crystalline Hydrate 3 of 8-(2-fluorobenzyl)-6-(3-(trifluoromethyl)-1H-1,2,4-triazol-5-yl)imidazo[1,2-a]pyrazine is characterized by at least three, at least four, or by at least five, x-ray powder diffraction peaks at 2Θ angles selected from at least three, or at least four x-ray powder diffraction peaks at 2Θ angles selected from 10.3°, 12.1°, 17.6°, and 22.0°, optionally together with one or both of the TGA, and DSC parameters recited above for Hydrate 3.

In one aspect, crystalline ethanol solvate of 8-(2-fluorobenzyl)-6-(3-(trifluoromethyl)-1H-1,2,4-triazol-5-yl)imidazo[1,2-a]pyrazine is characterized by x-ray diffraction pattern. The x-ray powder diffraction pattern can be acquired at room temperature in reflection mode using a Bruker D8 Discover system described herein. In one embodiment, crystalline ethanol solvate is characterized by at least three, at least four, at least five, at least six, or at least seven x-ray powder diffraction peaks at 2Θ angles selected from 10.4°, 13.8°, 17.1°, 17.5°, 20.2°, 25.5°, and 30.0°. In some embodiments, the peaks described above for crystalline ethanol solvate have a relative intensity of at least 10%, of at least 15%, of at least 20%, or of at least 25%.

Figure 17:
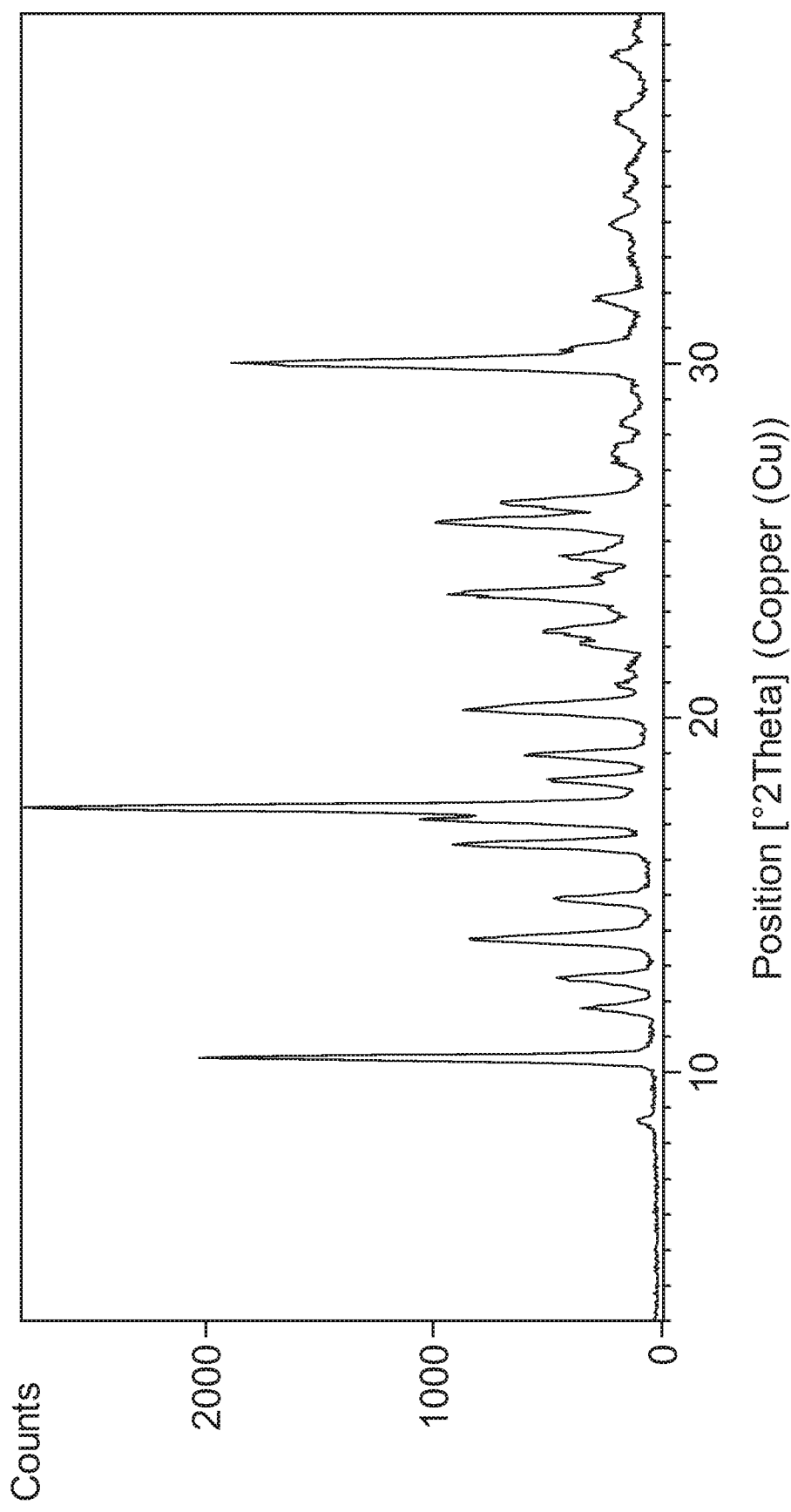
FIG. 17 is a XRPD pattern of 8-(2-fluorobenzyl)-6-(3-(trifluoromethyl)-1H-1,2,4-triazol-5-yl)imidazo[1,2-a]pyrazine ethanol solvate, acquired at room temperature in reflection mode using a Bruker D8 Discover system.

In another aspect, crystalline ethanol solvate of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 17.

In another aspect, crystalline ethanol solvate of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 6.

Figure 18:
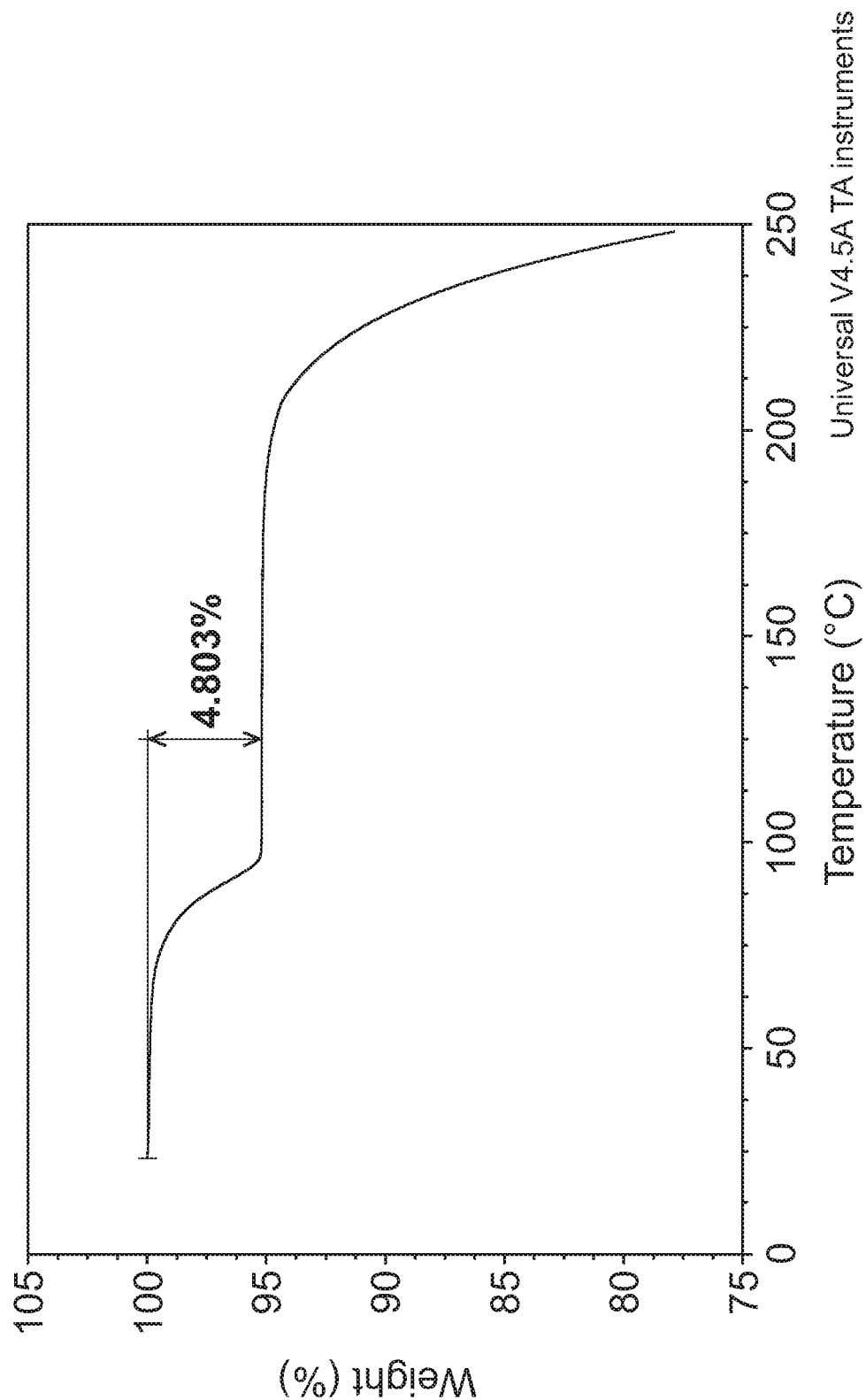
FIG. 18 is a TGA analysis of 8-(2-fluorobenzyl)-6-(3-(trifluoromethyl)-1H-1,2,4-triazol-5-yl)imidazo[1,2-a]pyrazine ethanol solvate.

In one aspect, crystalline ethanol solvate of 8-(2-fluorobenzyl)-6-(3-(trifluoromethyl)-1H-1,2,4-triazol-5-yl)imidazo[1,2-a]pyrazine has a TGA pattern that is substantially the same TGA pattern shown in FIG. 18.

In one aspect, the crystalline ethanol solvate of 8-(2-fluorobenzyl)-6-(3-(trifluoromethyl)-1H-1,2,4-triazol-5-yl)imidazo[1,2-a]pyrazine is characterized by at least three, at least four, by at least five, at least six, or at least seven x-ray powder diffraction peaks at 2Θ angles selected from 10.4°, 13.8°, 17.1°, 17.5°, 20.2°, 25.5°, and 30.0°; together with the TGA parameters recited above for ethanol solvate.

In one aspect, crystalline methanol solvate of 8-(2-fluorobenzyl)-6-(3-(trifluoromethyl)-1H-1,2,4-triazol-5-yl)imidazo[1,2-a]pyrazine is characterized by x-ray powder diffraction pattern. The x-ray powder diffraction pattern can be acquired at room temperature in reflection mode using a Bruker D8 Discover system described herein. In one embodiment, crystalline methanol solvate is characterized by at least three, at least four, at least five, at least six, at least seven or at least eight x-ray powder diffraction peaks at 2Θ angles selected from 7.7°, 11.0°, 14.2°, 16.2°, 17.1°, 23.0°, and 24.2°. In some embodiments, the peaks described above for crystalline methanol solvate have a relative intensity of at least 10%, of at least 15%, of at least 20%, or of at least 25%.

Figure 19:
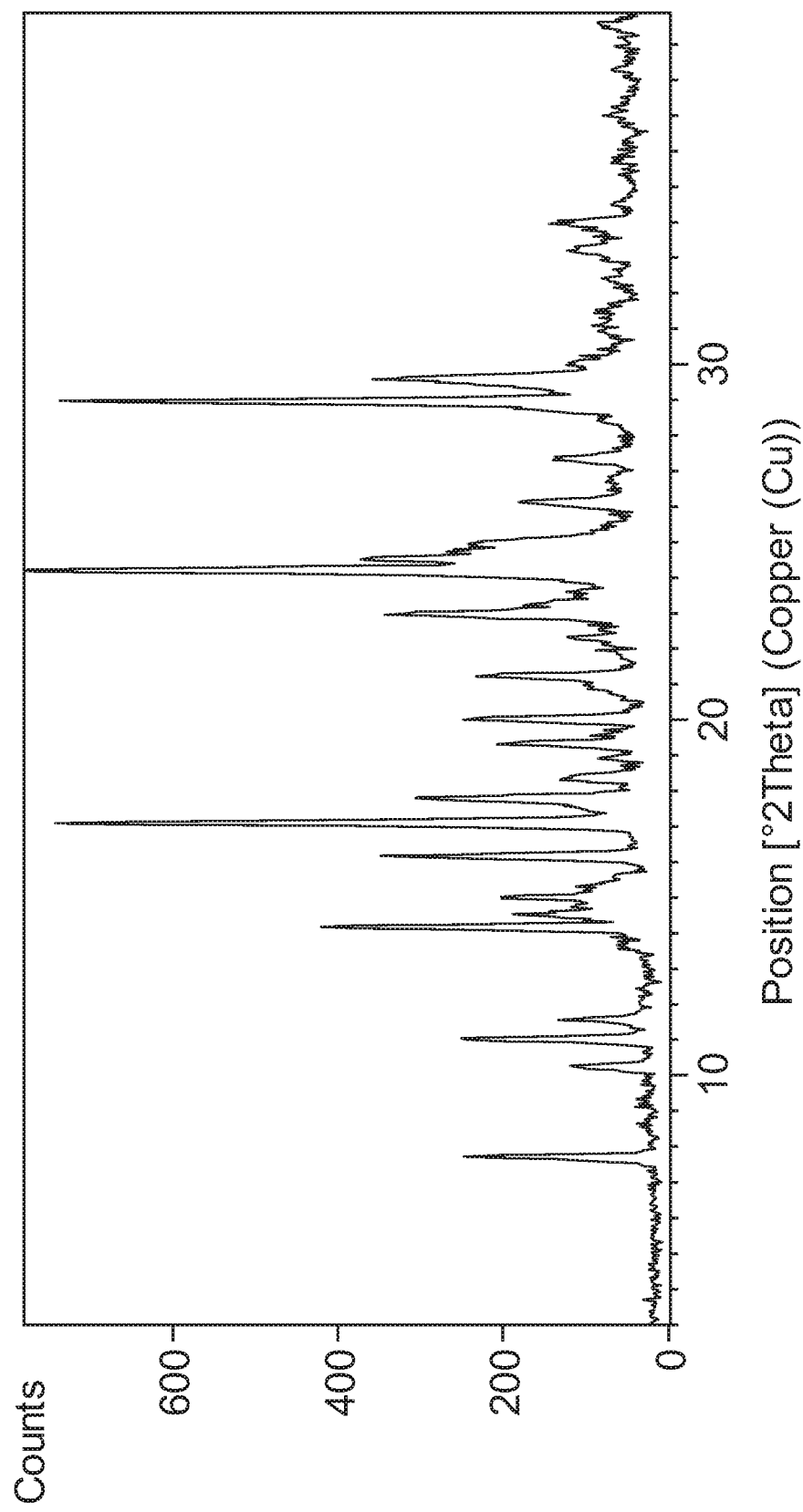
FIG. 19 is a XRPD pattern of 8-(2-fluorobenzyl)-6-(3-(trifluoromethyl)-1H-1,2,4-triazol-5-yl)imidazo[1,2-a]pyrazine methanol solvate, acquired at room temperature in reflection mode using a Bruker D8 Discover system.

In another aspect, crystalline methanol solvate of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 19.

In another aspect, crystalline methanol solvate of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 7.

Figure 20:
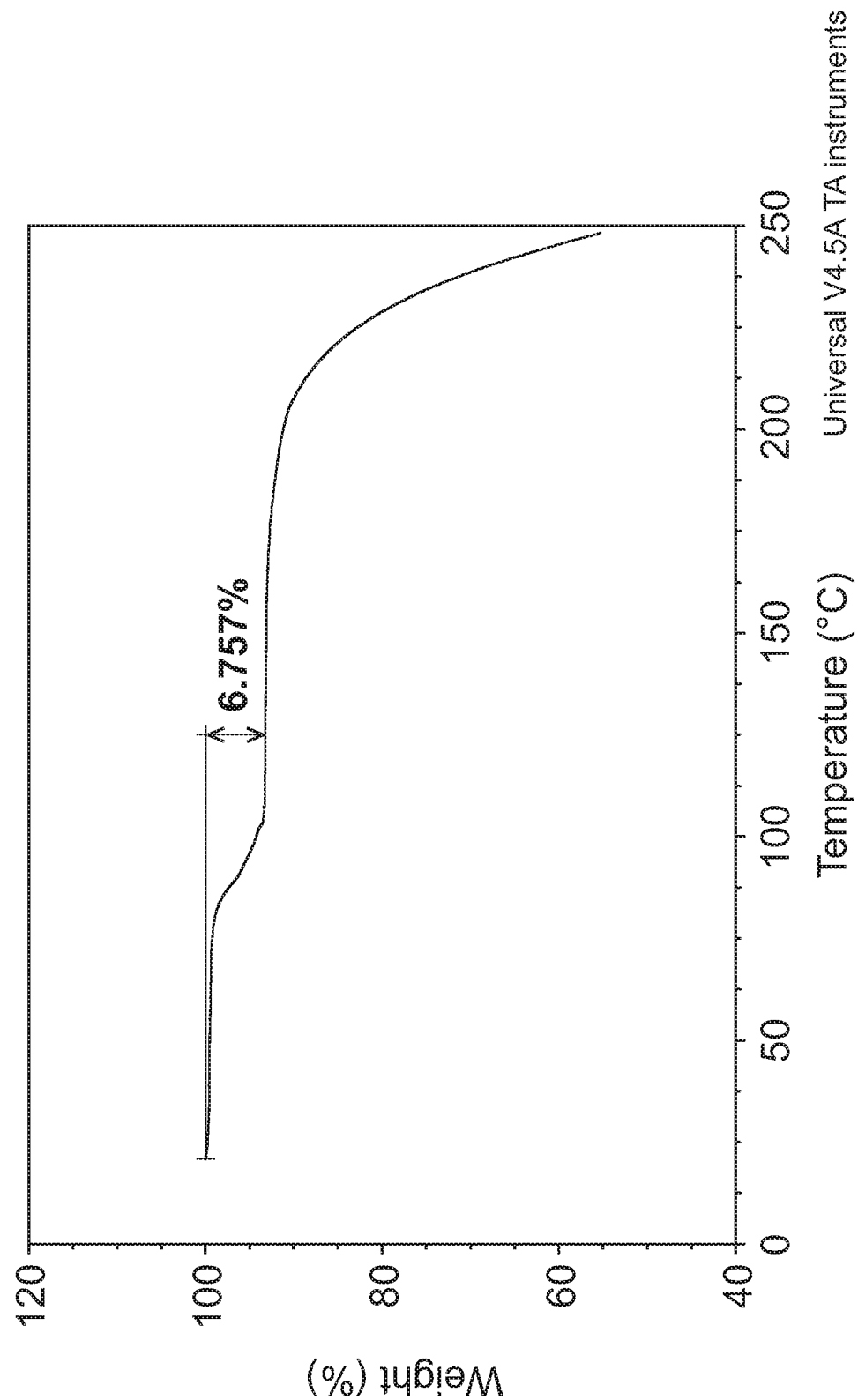
FIG. 20 is a TGA analysis of 8-(2-fluorobenzyl)-6-(3-(trifluoromethyl)-1H-1,2,4-triazol-5-yl)imidazo[1,2-a]pyrazine methanol solvate.

In one aspect, crystalline methanol solvate of 8-(2-fluorobenzyl)-6-(3-(trifluoromethyl)-1H-1,2,4-triazol-5-yl)imidazo[1,2-a]pyrazine has a TGA pattern that is substantially the same TGA pattern shown in FIG. 20.

In one aspect, the crystalline methanol solvate of 8-(2-fluorobenzyl)-6-(3-(trifluoromethyl)-1H-1,2,4-triazol-5-yl)imidazo[1,2-a]pyrazine is characterized by at least three, at least four, by at least five, at least six, at least seven, or at least eight x-ray powder diffraction peaks at 2Θ angles selected from 7.7°, 13.8°, 11.0°, 14.2°, 16.2°, 17.1°, 23.0°, and 24.2°; together with the TGA parameters recited above for methanol solvate.

In one aspect, crystalline methyl ethyl ketone solvate of 8-(2-fluorobenzyl)-6-(3-(trifluoromethyl)-1H-1,2,4-triazol-5-yl)imidazo[1,2-a]pyrazine is characterized by x-ray powder diffraction pattern. The x-ray powder diffraction pattern can be acquired at room temperature in reflection mode using a Bruker D8 Discover system described herein. In one embodiment, crystalline methyl ethyl ketone solvate is characterized by at least three, at least four, at least five, at least six, at least seven, at least eight, at least nine or at least ten x-ray powder diffraction peaks at 2Θ angles selected from 13.7°, 17.3°, 17.8°, 18.4°, 21.1°, 22.8°, 24.0°, 24.3°, and 25.1°. In some embodiments, the peaks described above for crystalline methyl ethyl ketone solvate have a relative intensity of at least 10%, of at least 15%, of at least 20%, or of at least 25%.

Figure 21:
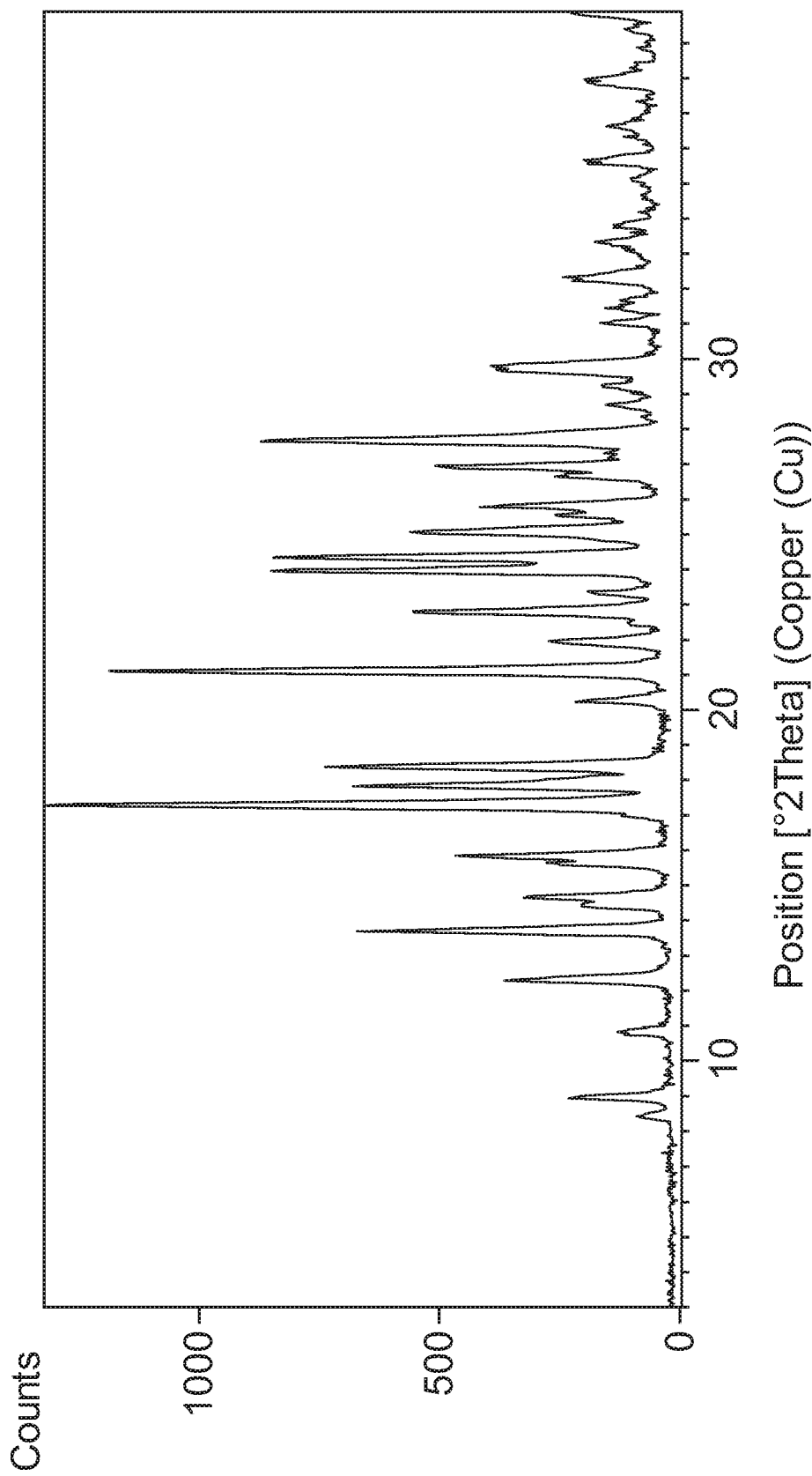
FIG. 21 is a XRPD pattern of 8-(2-fluorobenzyl)-6-(3-(trifluoromethyl)-1H-1,2,4-triazol-5-yl)imidazo[1,2-a]pyrazine methyl ethyl ketone solvate, acquired at room temperature in reflection mode using a Bruker D8 Discover system.

In another aspect, crystalline methyl ethyl ketone solvate of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 21.

In another aspect, crystalline methyl ethyl ketone solvate of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 8.

In one aspect, crystalline dichloromethane solvate of 8-(2-fluorobenzyl)-6-(3-(trifluoromethyl)-1H-1,2,4-triazol-5-yl)imidazo[1,2-a]pyrazine is characterized by x-ray powder diffraction pattern. The x-ray powder diffraction pattern can be acquired at room temperature in reflection mode using a Bruker D8 Discover system described herein. In one embodiment, crystalline dichloromethane solvate is characterized by at least three, at least four, at least five, at least six, or at least seven x-ray powder diffraction peaks at 2Θ angles selected from 14.4°, 15.7°, 19.7°, 20.9°, 21.8°, 22.7°, and 24.0°. In some embodiments, the peaks described above for crystalline dichloromethane solvate have a relative intensity of at least 10%, of at least 15%, of at least 20%, or of at least 25%.

Figure 22:
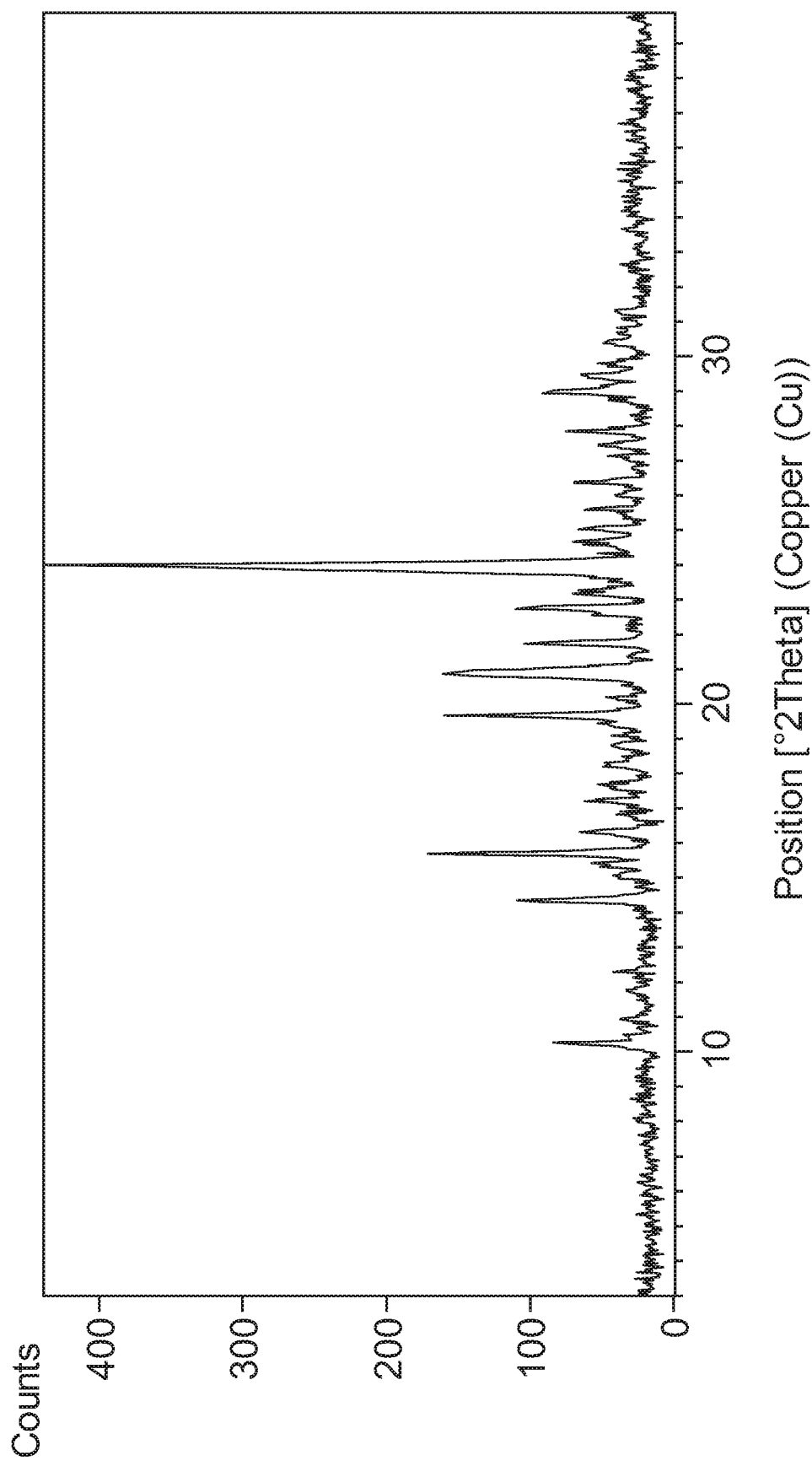
FIG. 22 is a XRPD pattern of 8-(2-fluorobenzyl)-6-(3-(trifluoromethyl)-1H-1,2,4-triazol-5-yl)imidazo[1,2-a]pyrazine dichloromethane solvate, acquired at room temperature in reflection mode using a Bruker D8 Discover system.

In another aspect, crystalline dichloromethane solvate of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 22.

In another aspect, crystalline dichloromethane solvate of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 9.

Figure 23:
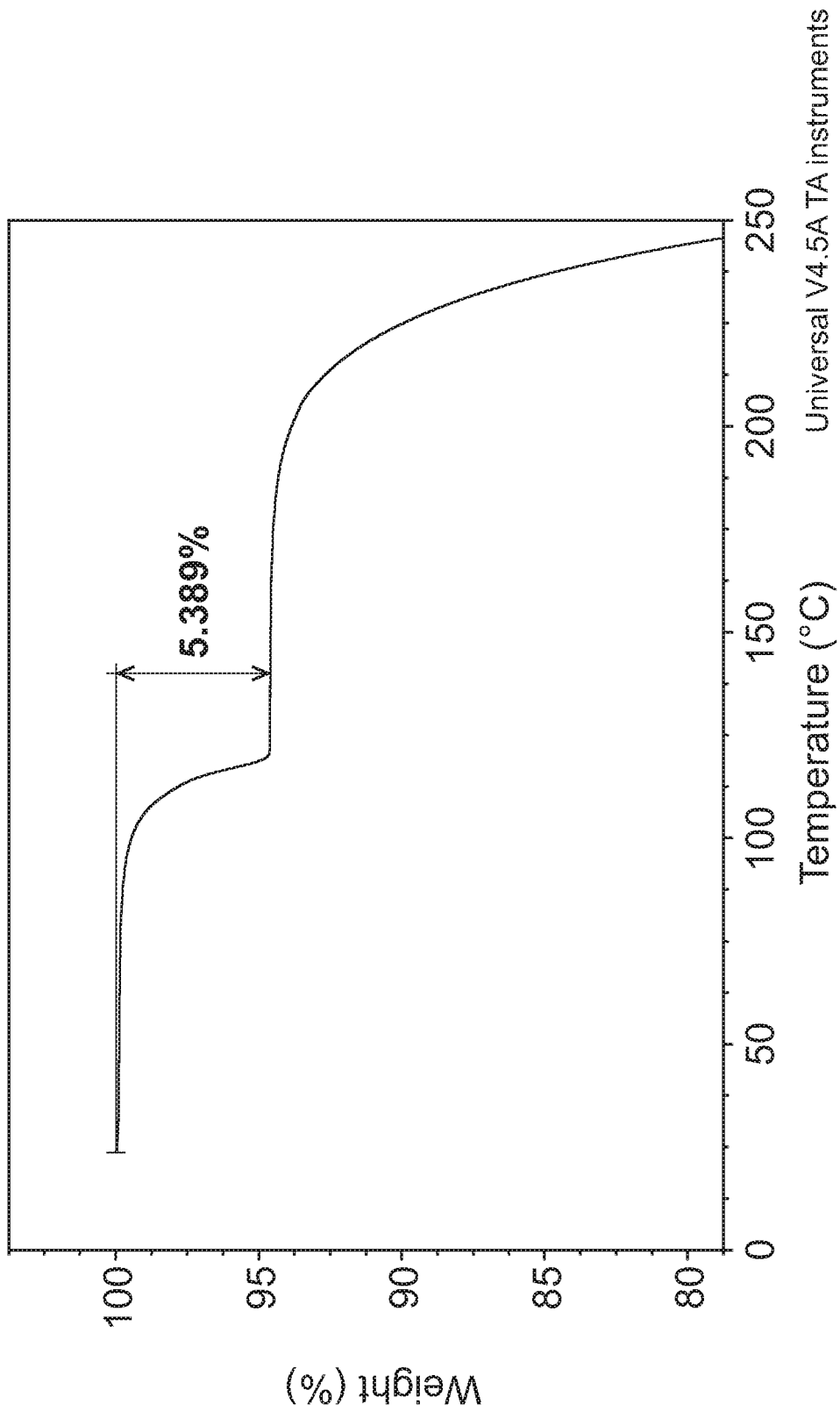
FIG. 23 is a TGA analysis of 8-(2-fluorobenzyl)-6-(3-(trifluoromethyl)-1H-1,2,4-triazol-5-yl)imidazo[1,2-a]pyrazine dichloromethane solvate.

In one aspect, crystalline dichloromethane solvate of 8-(2-fluorobenzyl)-6-(3-(trifluoromethyl)-1H-1,2,4-triazol-5-yl)imidazo[1,2-a]pyrazine has a TGA pattern that is substantially the same TGA pattern shown in FIG. 23.

In one aspect, the crystalline dichloromethane solvate of 8-(2-fluorobenzyl)-6-(3-(trifluoromethyl)-1H-1,2,4-triazol-5-yl)imidazo[1,2-a]pyrazine is characterized by at least three, at least four, by at least five, at least six, at least seven, or at least eight x-ray powder diffraction peaks at 2Θ angles selected from 14.4°, 15.7°, 19.7°, 20.9°, 21.8°, 22.7°, and 24.0°; together with the TGA parameters recited above for dichloromethane solvate.

In one aspect, crystalline acetonitrile solvate of 8-(2-fluorobenzyl)-6-(3-(trifluoromethyl)-1H-1,2,4-triazol-5-yl)imidazo[1,2-a]pyrazine is characterized by x-ray powder diffraction pattern. The x-ray powder diffraction pattern can be acquired at room temperature in reflection mode using a Bruker D8 Discover system described herein. In one embodiment, crystalline acetonitrile solvate is characterized by at least three, at least four, at least five, at least six, or at least seven x-ray powder diffraction peaks at 2Θ angles selected from 10.6°, 14.4°, 17.3°, 18.7°, 21.7°, 25.3°, and 25.9°. In some embodiments, the peaks described above for crystalline acetonitrile solvate have a relative intensity of at least 10%, of at least 15%, of at least 20%, or of at least 25%.

Figure 24:
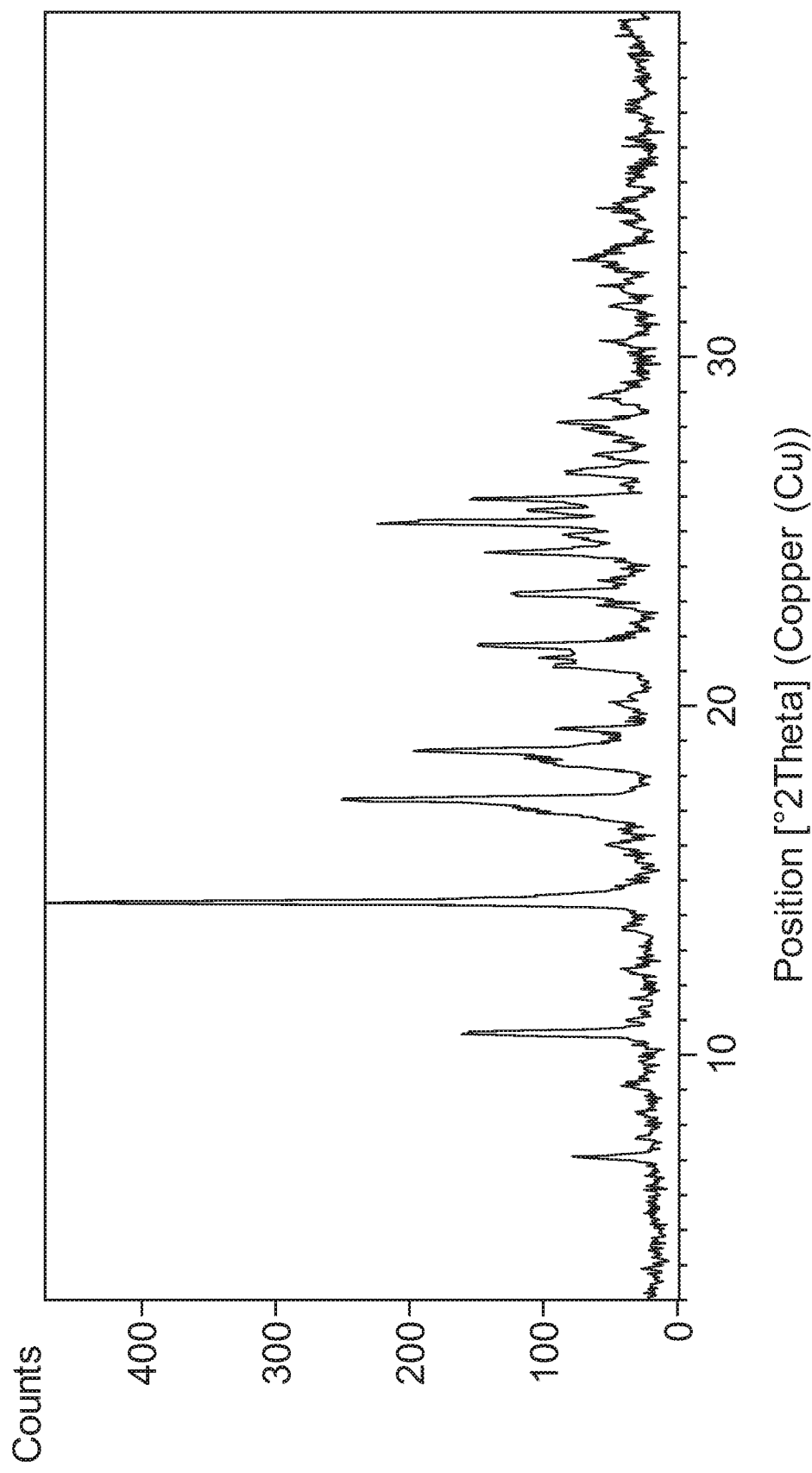
FIG. 24 is a XRPD pattern of 8-(2-fluorobenzyl)-6-(3-(trifluoromethyl)-1H-1,2,4-triazol-5-yl)imidazo[1,2-a]pyrazine acetonitrile solvate, acquired at room temperature in reflection mode using a Bruker D8 Discover system.

In another aspect, crystalline acetonitrile solvate of 8-(2-fluorobenzyl)-6-(3-(trifluoromethyl)-1H-1,2,4-triazol-5-yl)imidazo[1,2-a]pyrazine has an XRPD pattern that is substantially the same XRPD pattern shown in FIG. 24.

In another aspect, crystalline acetonitrile solvate of 8-(2-fluorobenzyl)-6-(3-(trifluoromethyl)-1H-1,2,4-triazol-5-yl)imidazo[1,2-a]pyrazine has an XRPD pattern that substantially includes the peaks in Table 10.

Figure 25:
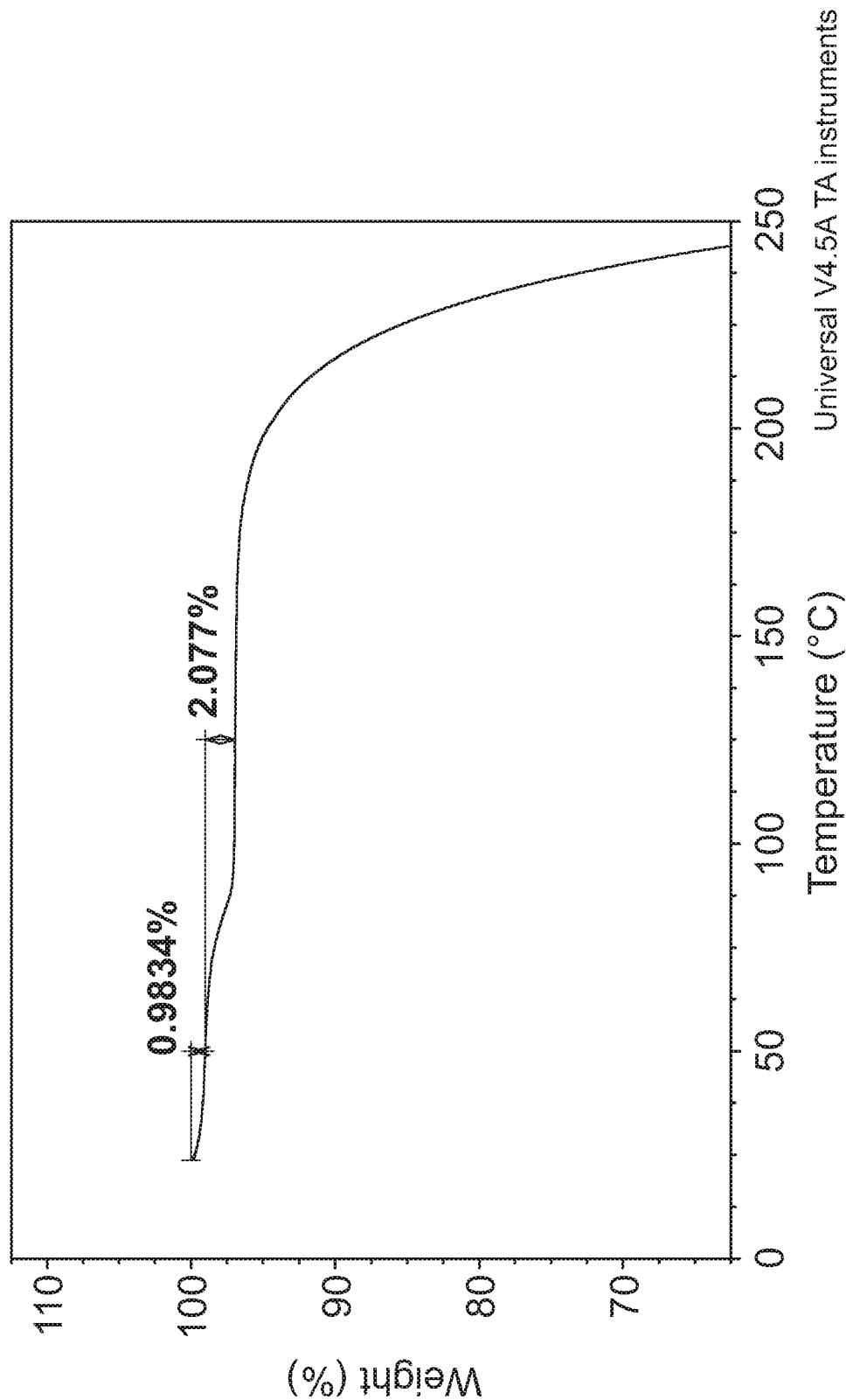
FIG. 25 is a TGA analysis of 8-(2-fluorobenzyl)-6-(3-(trifluoromethyl)-1H-1,2,4-triazol-5-yl)imidazo[1,2-a]pyrazine acetonitrile solvate.

In one aspect, crystalline acetonitrile solvate of 8-(2-fluorobenzyl)-6-(3-(trifluoromethyl)-1H-1,2,4-triazol-5-yl)imidazo[1,2-a]pyrazine has a TGA pattern that is substantially the same TGA pattern shown in FIG. 25.

In one aspect, the crystalline acetonitrile solvate of 8-(2-fluorobenzyl)-6-(3-(trifluoromethyl)-1H-1,2,4-triazol-5-yl)imidazo[1,2-a]pyrazine is characterized by at least three, at least four, by at least five, at least six, at least seven, or at least eight x-ray powder diffraction peaks at 2Θ angles selected from 10.6°, 14.4°, 17.3°, 18.7°, 21.7°, 25.3°, and 25.9°; together with the TGA parameters recited above for acetonitrile solvate.

It will be understood that the 2-theta values of the X-ray powder diffraction patterns for crystalline Form A, Form B, Hydrate 1, Hydrate 2, Hydrate 3, ethanol solvate, methanol solvate, methyl ethyl ketone solvate, dichloromethane solvate, or acetonitrile solvate may vary slightly from one instrument to another and depending on variations in sample preparation and batch to batch variation. Therefore, the XRPD peak positions for crystalline Form A, Form B, Hydrate 1, Hydrate 2, Hydrate 3, ethanol solvate, methanol solvate, methyl ethyl ketone solvate, dichloromethane solvate, or acetonitrile solvate are not to be construed as absolute and can vary ±0.2 degrees.

As intended herein, "substantially the same XRPD pattern as shown in FIG. 1A" and "substantially the same XRPD pattern as shown in FIG. 1B" and "substantially the same XRPD pattern as shown in FIG. 5A" and "substantially the same XRPD pattern as shown in FIG. 5B" and "substantially the same XRPD pattern as shown in FIG. 8A" and "substantially the same XRPD pattern as shown in FIG. 8B" and "substantially the same XRPD pattern as shown in FIG. 11A" and "substantially the same XRPD pattern as shown in FIG. 11B" and "substantially the same XRPD pattern as shown in FIG. 14A" and "substantially the same XRPD pattern as shown in FIG. 14B" means that for comparison purposes, at least 90% of the peaks shown in FIG. 1A, FIG. 1B, FIG. 5A, FIG. 5B, FIG. 8A, FIG. 8B, FIG. 11A, FIG. 11B, FIG. 14A and FIG. 14B are present. It is to be further understood that for comparison purposes some variability in peak position from those shown in FIG. 1A, FIG. 1B FIG. 5A, FIG. 5B, FIG. 8A, FIG. 8B, FIG. 11A, FIG. 11B, FIG. 14A and FIG. 14B are allowed, such as ±0.2 degrees. Similarly, substantially the same XRPD pattern as shown in FIG. 17 (or FIG. 19 or FIG. 21 or FIG. 22 or FIG. 24 or FIG. 26)" means that for comparison purposes, at least 90% of the peaks shown in FIG. 17 (or FIG. 19, FIG. 21, FIG. 22, FIG. 24, or FIG. 26) are present. It is to be further understood that for comparison purposes some variability in peak position from those shown in FIG. 17, FIG. 19, FIG. 21, FIG. 22, FIG. 24, FIG. 26 are allowed, such as ±0.2 degrees.

In one aspect, the present disclosure provides a process for preparing crystalline Form A of 8-(2-fluorobenzyl)-6-(3-(trifluoromethyl)-1H-1,2,4-triazol-5-yl)imidazo[1,2-a]pyrazine. Such a process includes, e.g., forming crystalline Form A from a mixture comprising 8-(2-fluorobenzyl)-6-(3-(trifluoromethyl)-1H-1,2,4-triazol-5-yl)imidazo[1,2-a]pyrazine, isopropyl acetate (IPAC) and n-heptane, where the n-heptane makes up more than 50% by volume of the composition. In one aspect, the process comprises stirring the mixture comprising 8-(2-fluorobenzyl)-6-(3-(trifluoromethyl)-1H-1,2,4-triazol-5-yl)imidazo[1,2-a]pyrazine and IPAC and n-heptane, where the n-heptane makes up more than 50% by volume of the composition for 24 hours to 1 week at room temperature. In one aspect, the processes described above results in the formation of crystalline Form A.

In one aspect, the present disclosure provides a process for preparing crystalline Form A of 8-(2-fluorobenzyl)-6-(3-(trifluoromethyl)-1H-1,2,4-triazol-5-yl)imidazo[1,2-a]pyrazine. Such a process includes, e.g., forming crystalline Form A from a mixture comprising 8-(2-fluorobenzyl)-6-(3-(trifluoromethyl)-1H-1,2,4-triazol-5-yl)imidazo[1,2-a]pyrazine and 100% n-heptane or cyclohexane. In one aspect, the process comprises stirring the mixture comprising 8-(2-fluorobenzyl)-6-(3-(trifluoromethyl)-1H-1,2,4-triazol-5-yl)imidazo[1,2-a]pyrazine and 100% n-heptane or cyclohexane for 24 hours to 1 week at room temperature. In one aspect, the processes described above results in the formation of crystalline Form A.

In one aspect, the present disclosure provides a process for preparing crystalline Form A of 8-(2-fluorobenzyl)-6-(3-(trifluoromethyl)-1H-1,2,4-triazol-5-yl)imidazo[1,2-a]pyrazine. Such a process includes, e.g., forming crystalline Form A from a mixture comprising 8-(2-fluorobenzyl)-6-(3-(trifluoromethyl)-1H-1,2,4-triazol-5-yl)imidazo[1,2-a]pyrazine and isopropyl acetate and heating the mixture to 45°, immediately diluting the suspension with n-heptane and stirred for 2 hours while slowly cooling to 20°, and then stirring for another 2 hours to 5°. In one aspect, the processes described above results in the formation of crystalline Form A.

In one aspect, the present disclosure provides a process for preparing crystalline Form B of 8-(2-fluorobenzyl)-6-(3-(trifluoromethyl)-1H-1,2,4-triazol-5-yl)imidazo[1,2-a]pyrazine. Such a process includes, e.g., forming crystalline Form B from a mixture comprising 8-(2-fluorobenzyl)-6-(3-(trifluoromethyl)-1H-1,2,4-triazol-5-yl)imidazo[1,2-a]pyrazine Form A and a solvent selected from (i) isopropyl acetate (IPAC), (ii) isopropyl alcohol (IPA); (iii) IPA/IPAC mixtures; (iv) mixtures of IPAC and hexane with IPAC making up 50% or more by volume of the composition, and (v) tetrahydrofuran. In one aspect, the process comprises stirring the mixture comprising 8-(2-fluorobenzyl)-6-(3-(trifluoromethyl)-1H-1,2,4-triazol-5-yl)imidazo[1,2-a]pyrazine Form A and in a solvent selected from isopropyl acetate (IPAC), isopropyl alcohol (IPA); IPA/IPAC mixtures; mixtures of IPAC and hexane with IPAC making up 50% or more by volume of the composition, and tetrahydrofuran for 24 hours to 1 week at room temperature. In one aspect, the processes described above results in the formation of crystalline Form B.

In one aspect, the present disclosure provides a process for preparing crystalline Hydrate 1 of 8-(2-fluorobenzyl)-6-(3-(trifluoromethyl)-1H-1,2,4-triazol-5-yl)imidazo[1,2-a]pyrazine. Such a process includes, e.g., forming crystalline Hydrate 1 from a mixture comprising 8-(2-fluorobenzyl)-6-(3-(trifluoromethyl)-1H-1,2,4-triazol-5-yl)imidazo[1,2-a]pyrazine Form A or Form B and water. In one aspect, the process comprises stirring the mixture comprising 8-(2-fluorobenzyl)-6-(3-(trifluoromethyl)-1H-1,2,4-triazol-5-yl)imidazo[1,2-a]pyrazine Form A or Form B and water for 24 hours to 1 week at room temperature. In one aspect, the processes described above results in the formation of crystalline Hydrate 1.

In one aspect, the present disclosure provides a process for preparing crystalline Hydrate 2 of 8-(2-fluorobenzyl)-6-(3-(trifluoromethyl)-1H-1,2,4-triazol-5-yl)imidazo[1,2-a]pyrazine. Such a process includes, e.g., forming crystalline Hydrate 1 from a mixture comprising 8-(2-fluorobenzyl)-6-(3-(trifluoromethyl)-1H-1,2,4-triazol-5-yl)imidazo[1,2-a]pyrazine Form A or Form B and an aqueous mixture containing cellulose-based polymers such as methylcellulose, surfactants such as Tween 80 and sodium lauryl sulfate, or a combination thereof, or forming crystalline Hydrate 1 from a mixture comprising 8-(2-fluorobenzyl)-6-(3-(trifluoromethyl)-1H-1,2,4-triazol-5-yl)imidazo[1,2-a]pyrazine Form A or Form B and an aqueous mixture containing 10% of organic solvents such as isopropyl alcohol. In one aspect, the process comprises stirring the mixture comprising 8-(2-fluorobenzyl)-6-(3-(trifluoromethyl)-1H-1,2,4-triazol-5-yl)imidazo[1,2-a]pyrazine Form A or Form B and an aqueous mixture containing cellulose-based polymers such as methylcellulose, surfactants such as Tween 80 and sodium lauryl sulfate, or a combination thereof, or the mixture comprising 8-(2-fluorobenzyl)-6-(3-(trifluoromethyl)-1H-1,2,4-triazol-5-yl)imidazo[1,2-a]pyrazine Form A or Form B and an aqueous mixture containing 10% of organic solvents such as isopropyl alcohol for 24 hours to 1 week at room temperature. In one aspect, the processes described above results in the formation of crystalline Hydrate 1.

In one aspect, the present disclosure provides a process for preparing crystalline Hydrate 3 of 8-(2-fluorobenzyl)-6-(3-(trifluoromethyl)-1H-1,2,4-triazol-5-yl)imidazo[1,2-a]pyrazine. Such a process includes, e.g., forming crystalline Hydrate 3 from a mixture comprising 8-(2-fluorobenzyl)-6-(3-(trifluoromethyl)-1H-1,2,4-triazol-5-yl)imidazo[1,2-a]pyrazine Form A or Form B and a solvent mixture containing 50% water and 50% organic solvent such as isopropyl alcohol. In one aspect, the process comprises stirring the mixture comprising 8-(2-fluorobenzyl)-6-(3-(trifluoromethyl)-1H-1,2,4-triazol-5-yl)imidazo[1,2-a]pyrazine Form A or Form B and a solvent mixture containing 50% water and 50% organic solvent such as isopropyl alcohol for 24 hours to 1 week at room temperature. In one aspect, the processes described above results in the formation of crystalline Hydrate 3.

In one aspect, the present disclosure provides a process for preparing crystalline ethanol solvate of 8-(2-fluorobenzyl)-6-(3-(trifluoromethyl)-1H-1,2,4-triazol-5-yl)imidazo[1,2-a]pyrazine. Such a process includes, e.g., forming crystalline ethanol solvate from a mixture comprising 8-(2-fluorobenzyl)-6-(3-(trifluoromethyl)-1H-1,2,4-triazol-5-yl)imidazo[1,2-a]pyrazine Form A or Form B and 100% ethanol. In one aspect, the process comprises stirring the mixture comprising 8-(2-fluorobenzyl)-6-(3-(trifluoromethyl)-1H-1,2,4-triazol-5-yl)imidazo[1,2-a]pyrazine Form A or Form B and ethanol for 24 hours to 1 week at room temperature. In one aspect, the processes described above results in the formation of crystalline ethanol solvate.

In one aspect, the present disclosure provides a process for preparing crystalline methanol solvate of 8-(2-fluorobenzyl)-6-(3-(trifluoromethyl)-1H-1,2,4-triazol-5-yl)imidazo[1,2-a]pyrazine. Such a process includes, e.g., forming crystalline methanol solvate from a mixture comprising 8-(2-fluorobenzyl)-6-(3-(trifluoromethyl)-1H-1,2,4-triazol-5-yl)imidazo[1,2-a]pyrazine Form A or Form B and 100% methanol. In one aspect, the process comprises stirring the mixture comprising 8-(2-fluorobenzyl)-6-(3-(trifluoromethyl)-1H-1,2,4-triazol-5-yl)imidazo[1,2-a]pyrazine Form A or Form B and methanol for 24 hours to 1 week at room temperature. In one aspect, the processes described above results in the formation of crystalline methanol solvate.

In one aspect, the present disclosure provides a process for preparing crystalline methyl ethyl ketone solvate of 8-(2-fluorobenzyl)-6-(3-(trifluoromethyl)-1H-1,2,4-triazol-5-yl)imidazo[1,2-a]pyrazine. Such a process includes, e.g., forming crystalline methyl ethyl ketone solvate from a mixture comprising 8-(2-fluorobenzyl)-6-(3-(trifluoromethyl)-1H-1,2,4-triazol-5-yl)imidazo[1,2-a]pyrazine Form A or Form B and 100% methyl ethyl ketone. In one aspect, the process comprises stirring the mixture comprising 8-(2-fluorobenzyl)-6-(3-(trifluoromethyl)-1H-1,2,4-triazol-5-yl) imidazo[1,2-a]pyrazine Form A or Form B and methyl ethyl ketone for 24 hours to 1 week at room temperature. In one aspect, the processes described above results in the formation of crystalline methyl ethyl ketone solvate.

In one aspect, the present disclosure provides a process for preparing crystalline dichloromethane solvate of 8-(2-fluorobenzyl)-6-(3-(trifluoromethyl)-1H-1,2,4-triazol-5-yl) imidazo[1,2-a]pyrazine. Such a process includes, e.g., forming crystalline dichloromethane solvate from a mixture comprising 8-(2-fluorobenzyl)-6-(3-(trifluoromethyl)-1H-1, 2,4-triazol-5-yl)imidazo[1,2-a]pyrazine Form A or Form B and 100% dichloromethane. In one aspect, the process comprises stirring the mixture comprising 8-(2-fluorobenzyl)-6-(3-(trifluoromethyl)-1H-1,2,4-triazol-5-yl)imidazo [1,2-a]pyrazine Form A or Form B and dichloromethane for 24 hours to 1 week at room temperature. In one aspect, the processes described above results in the formation of crystalline dichloromethane solvate.

In one aspect, the present disclosure provides a process for preparing crystalline acetonitrile solvate of 8-(2-fluorobenzyl)-6-(3-(trifluoromethyl)-1H-1,2,4-triazol-5-yl)imidazo[1,2-a]pyrazine. Such a process includes, e.g., forming crystalline acetonitrile solvate from a mixture comprising 8-(2-fluorobenzyl)-6-(3-(trifluoromethyl)-1H-1,2,4-triazol-5-yl)imidazo[1,2-a]pyrazine Form A or Form B and 100% acetonitrile. In one aspect, the process comprises stirring the mixture comprising 8-(2-fluorobenzyl)-6-(3-(trifluoromethyl)-1H-1,2,4-triazol-5-yl)imidazo[1,2-a]pyrazine Form A or Form B and in acetonitrile for 24 hours to 1 week at room temperature. In one aspect, the processes described above results in the formation of crystalline acetonitrile solvate.

Pharmaceutical Compositions and Methods of Administration

The polymorphic forms disclosed herein (e.g., Form A, Form B, Hydrate 1, Hydrate 2, Hydrate 3, ethanol solvate, methanol solvate, methyl ethyl ketone solvate, dichloromethane solvate, or acetonitrile solvate of the compound of Formula (I)) may be formulated as pharmaceutical compositions or "formulations".

A typical formulation is prepared by mixing Form A, Form B, Hydrate 1, Hydrate 2, Hydrate 3, ethanol solvate, methanol solvate, methyl ethyl ketone solvate, dichloromethane solvate, or acetonitrile solvate of the compound of Formula (I) and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which a compound of Formula I is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g. enteric or slow release) preservatives, antioxidants, opaquing agents, glidants, processing aids, colorants, sweeteners, perfuming agents, flavoring agents and other known additives to provide an elegant presentation of the drug (i.e., a compound of Formula I or pharmaceutical composition thereof) or aid in the manufacturing of the pharmaceutical product (i.e., medicament).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively; in colloidal drug delivery systems (for example, liposomes, albumin microspheres, microemulsions, nano-particles and nanocapsules) or in macroemulsions. Such techniques are disclosed in Remington's: The Science and Practice of Pharmacy, 21$^{st}$ Edition, University of the Sciences in Philadelphia, Eds., 2005 (hereafter "Remington's").

The formulations may be prepared using conventional dissolution and mixing procedures. The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically effective amount of the compound to be administered will be governed by such considerations, and is the minimum amount necessary to ameliorate, cure or treat the disease, or one or more of its symptoms.

The terms "administer", "administering" or "administration" in reference to a compound, composition or dosage form of the invention means introducing the compound into the system of the subject or patient in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g. orally (including, but not limited to solid dosage forms including hard or soft capsules (e.g.

gelatin capsules), tablets, pills, powders, sublingual tablets, troches, lozenges, and granules; and liquid dosage forms including, but are not limited to, pharmaceutically acceptable emulsions, microemulsions, aqueous or oil solutions, suspensions, syrups and elixirs, by inhalation (e.g. with an aerosol, gas, inhaler, nebulizer or the like), to the ear (e.g. using ear drops), topically (e.g. using creams, gels, inhalants, liniments, lotions, ointments, patches, pastes, powders, solutions, sprays, transdermal patches, etc.), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc.), via ear drops, via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Formulations of a compound intended for oral use may be prepared according to any method known to the art for the manufacture of pharmaceutical compositions.

In solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

The oral compositions (either solid or liquid) can also include excipients and adjuvants such as dispersing or wetting agents, such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate); emulsifying and suspending agents, such as sodium carboxymethylcellulose, croscarmellose, povidone, methylcellulose, hydroxypropyl methylcelluose, sodium alginate, polyvinylpyrrolidone, gum tragacanth and gum acacia; sweetening, flavoring, and perfuming agents; and/or one or more preservatives such as ethyl or n-propyl p-hydroxy-benzoate, one or more coloring agents, one or more flavoring agents and one or more sweetening agents, such as sucrose or saccharin.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc.) which is administered by rapid inhalation through the nasal passage or by inhalation through the mouth so as to reach the alveolar sacs.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs. The active component is admixed under sterile conditions with a pharmaceutically acceptable carrier and any needed preservatives or buffers as may be required.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using a compound of Formula I may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of a compound of Formula I include Tween™-60, Span™-80, cetostearyl alcohol, benzyl alcohol, myristyl alcohol, glyceryl mono-stearate and sodium lauryl sulfate.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

Sterile injectable forms of the compositions described herein (e.g. for parenteral administration) may be aqueous or oleaginous suspension. These suspensions may be formulated according to techniques known in the art using suitable dispersing or wetting agents and suspending agents (including those described in the preceding paragraph). The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as a vegetable oil, for example arachis oil, olive oil, sesame oil or coconut oil, especially in their polyoxyethylated versions, or in mineral oil such as liquid paraffin. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

In another aspect, Form A, Form B, Hydrate 1, Hydrate 2, Hydrate 3, ethanol solvate, methanol solvate, methyl ethyl ketone solvate, dichloromethane solvate, or acetonitrile solvate of the compound of Formula (I) may be formulated in a veterinary composition comprising a veterinary carrier. Veterinary carriers are materials useful for the purpose of administering the composition and may be solid, liquid or gaseous materials which are otherwise inert. In the veterinary art and are compatible with the active ingredient. These veterinary compositions may be administered parenterally, orally or by any other desired route.

Therapeutic Methods

In another aspect, the invention also provides a method of treating a disease in a subject in need thereof, comprising administering, alone or in combination therapy, a therapeutically effective amount of Form A, Form B, Hydrate 1, Hydrate 2, Hydrate 3, ethanol solvate, methanol solvate, methyl ethyl ketone solvate, dichloromethane solvate, or acetonitrile solvate of the compound of Formula (I) to the subject; wherein the disease is one that benefits from sGC stimulation or from an increase in the concentration of NO or cGMP or both, or from the upregulation of the NO pathway. The invention also provides a method of treating a disease in a subject in need thereof, comprising administering, alone or in combination therapy, a pharmaceutical composition comprising Form A, Form B, Hydrate 1, Hydrate 2, Hydrate 3, ethanol solvate, methanol solvate, methyl ethyl ketone solvate, dichloromethane solvate, or acetonitrile solvate to the subject or a dosage form comprising the pharmaceutical composition, wherein the disease is one that benefits from sGC stimulation or from an increase in the concentration of NO or cGMP or both, or from the upregulation of the NO pathway.

In some embodiments, the compounds here disclosed are sGC stimulators that may be useful in the prevention and/or treatment of diseases characterized by undesirable reduced bioavailability of and/or sensitivity to NO, such as those associated with conditions of oxidative stress or nitrosative stress.

Increased concentration of cGMP leads to vasodilation, inhibition of platelet aggregation and adhesion, anti-hypertensive effects, anti-remodeling effects, anti-apoptotic effects, anti-inflammatory, anti-fibrotic effects, metabolic effects and neuronal signal transmission effects. Thus, sGC stimulators may be used to treat and/or prevent a range of diseases.

Specific diseases or disorders which may be treated and/or prevented by administering an sGC stimulator of the invention (e.g., Form A, Form B, Hydrate 1, Hydrate 2, Hydrate 3, ethanol solvate, methanol solvate, methyl ethyl ketone solvate, dichloromethane solvate, or acetonitrile solvate), include but are not limited to:

A beta lipoproteinemia, achalasia (e.g., esophageal achalasia), acute respiratory distress syndrome (ARDS), adhesive capsulitis, age-related learning and memory disturbances, age-related memory loss, alcoholism, alopecia or hair loss, altitude sickness, Alzheimer's disease (including pre-Alzheimer's disease, mild to moderate Alzheimer's disease and moderate to severe Alzheimer's disease), amyotrophic lateral sclerosis (ALS or Lou Gehrig's disease), anal fissures, aneurysm, angina (e.g., stable or unstable angina pectoris, variant angina, Prinzmetal's angina, microvascular angina), anxiety or anxiety disorders, arginosuccinic aciduria, arterial and venous thromboses, arthritis, Asperger's syndrome, asthma and asthmatic diseases, ataxia, telangliectasia, atherosclerosis (e.g., atherosclerosis associated with endothelial injury, platelet and monocyte adhesion and aggregation, smooth muscle proliferation or migration), atrophic vaginitis, attention deficit disorder (ADD) and attention deficit hyperactivity disorder (ADHD), autism and disorders in the autism spectrum, benign prostatic hyperplasia (BPH) or hypertrophy or enlargement, bipolar disorder, bladder outlet obstruction, bladder pain syndrome (BPS), blepharitis, bone and carbohydrate metabolism disturbances, bone healing (e.g. bone healing following osteoclastic bone remodeling, osteoclastic bone resorption, new bone formation), brain aneurysm, brain hypoxia, cancer metastasis, cerebral amyloid angiopathy (CAA) or congophilic angiopathy, cerebral autosomal-dominant arteriopathy with subcortical infarcts and leukoencephalopathy (CADASIL or CADASIL syndrome), cerebral perfusion, cerebral small vessel disease, cerebral vasospasm, chemo-brain, childhood disintegrative disorder, chronic bronchitis, chronic fatigue, chronic traumatic encephalopathy (CTE), ciliopathies, cirrhosis (e.g., liver cirrhosis, liver cirrhosis associated with chronic liver disease, primary biliary cirrhosis), CNS-disease related sexual dysfunction, CNS-disease related sleep disturbances, cognitive defect associated with Huntington's Disease, cognitive dysfunction, cognitive impairment (e.g., vascular cognitive impairment, mild cognitive impairment, cognitive impairment associated with diabetes, cognitive impairment associated with Multiple Sclerosis, cognitive impairment associated with obstructive sleep apnea, cognitive impairment associated with schizophrenia (CIAS), cognitive impairment associated with sickle cell disease, concussion, congenital myasthenic syndrome, connective tissue disease, consequences of cerebral infarction (apoplexia cerebri), conservation of blood substituents in trauma patients, CREST syndrome, Crohn's disease, cystic fibrosis (CF), delusional disorder, dementia (e.g., vascular dementia, post-stroke dementia, Lewy body dementia, dementia with frontal lobe degeneration, dementia with frontotemporal lobar degeneration, dementia with corticobasal degeneration, Creutzfeldt-Jakob dementia, HIV-dementia, multi-infarct dementia, post-operative dementia, strategic single-infarct dementia, HIV-associated dementia (including asymptomatic neurocognitive impairment (ANI), minor neurocognitive disorder (MND), HIV-associated dementia (HAD, also called AIDS dementia complex [ADC] or HIV encephalopathy), pre-senile dementia (mild cognitive impairment, MCI), mixed dementia, Binswanger's dementia (subcortical arteriosclerotic encephalopathy), Parkinson's Dementia), demyelination, depression, depressive disorder, dermatomyositis, diabetic angiopathy, diabetic macular edema, diabetic microangiopathies, diabetic ulcers or wounds (e.g., diabetic food ulcer), diseases associated with or related to metabolic syndrome (e.g. obesity, diabetes, insulin resistance, elevated fasting glucose, elevated fasting insulin, elevated lipids), diseases involving downregulated neurotransmitters, diseases involving impaired cerebral blood flow, diseases involving impaired neurodegeneration, diseases involving impaired synaptic function, diseases involving neuroinflammation, diseases involving neurotoxicity, diseases of the organs of the male and female urogenital system (benign and malignant), disturbances of concentration in children with learning and memory problems, Down syndrome, drug addiction, drug-induced psychosis, dry eye syndrome, Duchenne muscular dystrophy, Dupuytren's contracture, dyskinesia (e.g., acute dyskinesia, chronic or tardive dyskinesia, non-motor dyskinesia, levo-dopa induced dyskinesia (LID)), dysmenhorrea (e.g., primary dysmenhorrea, secondary dysmenhorrea), dyspareunia, dysphagia, dystonia (e.g., generalized dystonia, focal dystonia, segmental dystonia, sexual dystonia, intermediate dystonia, acute dystonic reaction, genetic or primary dystonia), edema, electrolyte disturbances (e.g., herkalemia, hyponatremia), emphysema, endometriosis, endothelial dysfunction or injury and diseases associated with endothelial dysfunction, erectile dysfunction, esophageal achalasia, Fabry Disease, female sexual dysfunction (e.g., female sexual arousal dysfunction), fibromyalgia, fibrosis (e.g., endomyocardial fibrosis, atrial fibrosis, cardiac interstitial fibrosis, cardiac fibrosis, pulmonary fibrosis, eye fibrosis, skin fibrosis, intestinal fibrosis, renal or kidney fibrosis, interstitial renal fibrosis, pulmonary fibrosis, idiopathic pulmonary fibrosis, progressive massive fibrosis of the lungs, liver fibrosis, mediastinal fibrosis, retroperitoneal fibrosis, arthrofibrosis, bone marrow fibrosis, myelofibrosis, osteomyelofibrosis, radiation-induced fibrosis, pancreatic fibrosis), Fragile X, functional dyspepsia, gastroparesis, Gaucher Disease, general disturbances of concentration, general psychosis, glaucoma, glioblastoma, glomerulopathies (e.g., glomerulonephritis, acute glomerulonephritis, glomerulosclerosis, focal segmental glomerulosclerosis), granulomas, head injury, hearing impairment (e.g., partial hearing loss, total hearing loss, partial deafness, total deafness, noise-induced hearing loss), heart disease (e.g., left ventricular myocardial remodeling, left ventricular systolic dysfunction, ischemic cardiomyopathy, dilated cardiomyopathy, alcoholic cardiomyopathy, storage cardiomyopathies, congenital heart defects, decreased coronary blood flow, diastolic or systolic dysfunction, coronary insufficiency, acute coronary syndrome, coronary artery disease, arrhythmias, reduction of ventricular preload, cardiac hypertrophy, right heart hypertrophy, disturbances of atrial and ventricular rhythm and heart conduction disturbances, atrioventricular blocks of degree I-III (AVB I-III), supraventricular tachyarrhythmia, premature ventricular contraction, atrial fibrillation, atrial flutter, ventricular fibrillation, ventricular flutter, ventricular tachyarrhythmia, torsade-depointes tachycardia, atrial and ventricular extrasystoles, AV-junction extrasystoles, sick-sinus syndrome, AV-node reentry tachycardia, Wolff-Parkinson-White syndrome, myocardial insufficiency, chronic, acute or viral myocarditis, cardiogenic shock, cardiac remodeling), heart failure (HF; e.g.: Heart failure with preserved ejection fraction (HFPEF), Heart failure with reduced ejection fraction (HFREF), acute heart failure, chronic heart failure, acute phases of an existing chronic heart failure (worsening HF), transient heart failure, post-acute heart failure, systolic heart failure, diastolic heart failure, congestive heart failure, acute decompensated heart failure, right ventricular failure, total heart failure, high output heart failure, heart failure with valvular defects, diabetic heart failure, heart failure/cardiorenal syndrome, right heart failure), high concentration of plasminogen activator inhibitor 1 (PA-1), high levels of fibrinogen and low density DLD, histiocytosis X, Huntington's disease or chorea (HD), hyperammonemia and related, hypertension (e.g., arterial hypertension, resistant hypertension, diabetic hypertension, idiopathic hypertension, essential hypertension, secondary hypertension, gestational hypertension, portal hypertension, systemic hypertension, pre-eclampsia, increased acute and chronic coronary blood pressure), hypertonia, hypertrophic scars, hypoactive sexual arousal disorder, hypoperfusion, impotence, Inflammatory bowel disease (e.g., Crohn's disease, Ulcerative Colitis), inflammation caused by cerebral malaria, inflammation caused by infectious disease, inflammatory response in perioperative care, platelet aggregation, intellectual disability, intermittent claudication, interstitial cystitis (IC), intradialytic hypotension, ischemia (e.g., cerebral ischemia, myocardial ischemia, thromboembolic ischemia, critical limb ischemia), keloids, kidney disease (e.g., chronic kidney disease, acute and chronic renal failure, acute and chronic renal insufficiency, sequelae of renal insufficiency, renal-insufficiency related to pulmonary enema, renal-insufficiency related to HF, renal-insufficiency related to uremia or anemia, primary kidney disease, congenital kidney disease, polycystic kidney disease progression, kidney transplant rejection, immune complex-induced kidney disease, abnormally reduced creatinine and/or water excretion, abnormally increased blood concentrations of urea, nitrogen, potassium and/or creatinine, altered activity of renal enzymes (e.g. glutamyl synthetase), altered urine osmolarity or urine volume, increased microalbuminuria, microalbuminuria, lesions of glomeruli and arterioles, tubular dilatation, hyperphosphatemia, vascular kidney disease, renal cysts, renal edema due to HF), Korsakoff psychosis, leukocyte activation, levo-dopa induced addictive behavior, lichen sclerosus, lipid related disorders (e.g., excessive adiposity, excessive subcutaneous fat, hyperlipidemias, dyslipidemia, hypercholesterolemias, decreased high-density lipoprotein cholesterol (HDL-cholesterol), moderately elevated low-density lipoprotein cholesterol (LDL-cholesterol) levels, hypertriglyceridemias, hyperglyceridemia, hypolipoproteinanemias, sitosterolemia, fatty liver disease, liver steatosis or abnormal lipid accumulation in the liver, steatosis of the heart, kidney or muscle, sitosterolemia, xanthomatosis, Tangier disease), liver diseases (e.g., vascular liver disease, hepatic stellate cell activation, hepatic fibrous collagen and total collagen accumulation, liver disease of necro-inflammatory and/or of immunological, cholestatic liver disease associated with granulomatous liver diseases, cholestatic liver disease associated with liver malignancies, cholestatic liver disease associated with intrahepatic cholestasis of pregnancy, cholestatic liver disease associated with hepatitis, cholestatic liver disease associated with sepsis, cholestatic liver disease associated with drugs or toxins, cholestatic liver disease associated with graft-versus-host disease, cholestatic liver disease associated with post-liver transplantation, cholestatic liver disease associated with choledocholithiasis, cholestatic liver disease associated with bile duct tumors, cholestatic liver disease associated with pancreatic carcinoma, cholestatic liver disease associated with Mirizzi's syndrome, cholestatic liver disease associated with AIDS, cholangiopathy, cholestatic liver disease associated with parasites, cholestatic liver disease associated with schistosomiasis, hepatitis, non-alcoholic steatohepatitis (NASH), non-alcoholic fatty liver disease (NAFLD), hepatic vaso-occlusive disease (VOD), hepatic sinusoidal obstruction syndrome (SOS), hepatic encephalopathy), localized thrombosis, lower urinary tract syndromes (LUTS), lumbar spinal canal stenosis, lupus nephritis, lupus or Systemic Lupus Erythematosus, microalbuminuria, microcirculation abnormalities, migraines, minor neurocognitive disorder (MND), morphea, moyamoya, multiple lacunar infarction, multiple organ dysfunction syndrome (MODS), multiple organ failure (MOF), multiple sclerosis (MS, including clinically isolated syndrome (CIS), relapsing-remitting MS (RRMS), primary progressive MS (PPMS), secondary progressive MS (SPMS)), multiple system atrophy (MSA), myocardial infarction or heart attack (e.g., ST-segment elevation myocardial infarction, Non-ST-segment elevation myocardial infarction, old myocardial infarction), myopic choroidal neovascularization, naevi, narcotic dependence, nephropathies (e.g., diabetic nephropathy, non-diabetic nephropathy, nephritis, nephropathy induced by toxins, contrast medium induced nephropathy, diabetic or non-diabetic nephrosclerosis, nephrotic syndrome, pyelonephritis, nephrogenic fibrosis), neurodegenerative diseases, neurogenic bladder and incontinence, neuroinflammation, neurologic disorders associated with decreased nitric oxide production, neuromuscular diseases (e.g., Duchenne muscular dystrophy (DMD), Becker muscular dystrophy (BMD), limb girdle muscular dystrophies, distal myopathies, type I and type II myotonic dystrophies, facio-scapulo-peroneal muscular dystrophy, autosomal and X-linked Emery-Dreifuss muscular dystrophy, oculopharyngeal muscular dystrophy, amyotrophic lateral sclerosis, spinal muscle atrophy (SMA)), neuromyelitis optica, neuropathies (e.g., peripheral neuropathy, autonomic neuropathy, central nervous system neuropathy, chemotherapy induced neuropathy, diabetic neuropathy, painful neuropathies, neuropathic pain, non-painful neuropathies, painful diabetic neuropathy, non-painful diabetic neuropathy, neuropathies associated to a CNS disease (e.g., Multiple sclerosis, MS), radiation-induced neuropathy), neuropathic pain associated with shingles, neuropathic pain associated with spine surgery), obsessive compulsive disorder (OCD), obstructive thromboanginitis, obstructive uropathy, oesinophilic fasciitis, osteoporosis, overactive bladder, pain (e.g., acute pain, central pain syndrome, inflammatory pain, postoperative pain, tonic pain, visceral pain, claudication pain, orphan pain indications (e.g., Acetazolamide-responsive myotonia, Autoerythrocyte sensitization syndrome, Autosomal dominant Charcot-Marie-Tooth disease type 2V, Autosomal dominant intermediate Charcot-Marie-Tooth disease with neuropathic pain, Autosomal recessive limb-girdle muscular dystrophy type 2A, Channelopathy-associated congenital insensitivity to pain, Chronic pain requiring intraspinal analgesia, Complex regional pain syndrome, Complex regional pain syndrome type 1, Complex regional pain syndrome type 2, Congenital insensitivity to pain with hyperhidrosis, Congenital insensitivity to pain with severe intellectual disability, Congenital insensitivity to pain-hypohidrosis syndrome, Diffuse palmoplantar keratoderma with painful fissures, Familial episodic pain syndrome, Familial episodic pain syndrome with predominantly lower limb involvement, Familial episodic pain syndrome with predominantly upper body involvement, Hereditary painful callosities, Hereditary sensory and autonomic neuropathy type 4, Hereditary sensory and autonomic neuropathy type 5, Hereditary sensory and autonomic neuropathy type 7, Interstitial cystitis, Painful orbital and systemic neurofibromas-marfanoid habitus syndrome, Paroxysmal extreme pain disorder, Persistent idiopathic facial pain, Qualitative or quantitative defects of calpain, Tolosa-Hunt syndrome, pancreatitis, panic disorder, Parkinson's disease, Parkinsonism Plus, Parkinson's Dysphagia, pathological eating disorders, pelvic pain, peripheral vascular disease (e.g., peripheral arterial disease, peripheral arterial occlusive disease, peripheral embolism, peripheral perfusion disturbances), peritonitis, pervasive development disorder, Peyronie's disease, Picks syndrome, polychondritis, polymyositis, post herpetic neuralgia, post-traumatic head injury, post-traumatic stress disorder (PTSD), premature ejaculation, progressive nuclear palsy, prostate hypertrophy, pulmonary disease (e.g., plexogenic pulmonary arteriopathy, bronchoconstriction or pulmonary bronchoconstriction, vascular disease of the lung, chronic obstructive pulmonary disease (COPD), pulmonary capillary hemangiomatosis, lymphangiomatosis and compressed pulmonary vessels (e.g., due to adenopathy, tumor or fibrosing mediastinitis), pulmonary vascular remodeling, pulmonary hypertonia), pulmonary hypertension (PH, e.g., pulmonary arterial hypertension (PAH), primary PH, secondary PH, sporatid PH, pre-capically PH, idiopathic PH, PH associated with left ventricular disease, PH associated with HIV, PH associated with SCD, PH associated with thromboembolism (chronic thromboembolic PH or CTEPH), PH associated with sarcoidosis, PH associated with chronic obstructive pulmonary disease, PH associated with acute respiratory distress syndrome (ARDS), PH associated with acute lung injury, PH associated with alpha-1-antitrypsin deficiency (AATD), PH associated with pulmonary emphysema (e.g., smoking induced emphysema), PH associated with lung disease, PH associated with hypoxemia, PH associated with scleroderma, PH associated with cystic fibrosis (CF), PH associated with left ventricular dysfunction, PH associated with hypoxemia, PH (WHO groups I, II, III, IV and V), PH associated with mitral valve disease, PH associated with pericarditis, PH associated with constrictive pericarditis, PH associated with aortic stenosis, PH associated with dilated cardiomyopathy, PH associated with hyperthrophic cardiomyopathy, PH associated with restrictive cardiomyopathy, PH associated with mediastinal fibrosis, PH associated with pulmonary fibrosis, PH associated with anomalous pulmonary venous drainage, PH associated with pulmonary veno-occlusive disease, PH associated with pulmonary vasculitis, PH associated with collagen vascular disease, PH associated with congenital heart disease, PH associated with pulmonary venous hypertension, PH associated with interstitial lung disease, PH associated with sleep-disordered breathing, PH associated with chronic airflow obstruction, PH associated with obstructive sleep apnea, PH associated with central sleep apnea, PH associated with mixed sleep apnea, PH associated with alveolar hypoventilation disorders, PH associated with chronic exposure to high altitude, PH associated with neonatal lung disease, PH associated with alveolar-capillary dysplasia, PH associated with sickle cell disease, PH associated with other coagulation disorders, PH associated with chronic thromboembolism), radiculopathy, Raynaud's disease, Raynaud's syndrome (primary or secondary), refractory epilepsy, Renpennings's syndrome, reperfusion injury (e.g., ischemia-reperfusion damage, ischemia-reperfusion associated with organ transplant), restenosis (e.g., restenosis developed after thrombolysis therapies, after percutaneous transluminal angioplasties (PTAs), after transluminal coronary angioplasties (PTCAs), after heart transplant or after bypass operations), retinopathies (e.g., diabetic retinopathy, non-diabetic retinopathy, non-proliferative diabetic retinopathy, proliferative vitroretinopathy, peripheral retinal degeneration, retinal vein occlusion), Rhett's disorder, rheumatoid or rheumatic disease (e.g., arthritis, rheumatoid arthritis), sarcoidosis, sarcoids, schistosomiasis, schizoaffective disorder, schizophrenia, schizophrenia with dementia, scleroderma (e.g., localized scleroderma or circumscribed scleroderma, systemic scleroderma), sclerosis (e.g. renal sclerosis, progressive sclerosis, liver sclerosis, primary sclerosing cholanginitis, sclerosis of the gastro-intestinal tract, hippocampal sclerosis, focal sclerosis, primary lateral sclerosis, osteosclerosis, otosclerosis, atherosclerosis, tuberous sclerosis, systemic sclerosis), sepsis or septic shock or anaphylactic shock, Sickle Cell Anemia, Sickle Cell Disease, Sjogren's syndrome, sleep-wake disorders, Sneddon's syndrome, spasms (e.g., coronary spasms, vascular spasms, spasms of the peripheral arteries), spinal cord injury, spinal muscular atrophy, spinal subluxations, spinocerebellar ataxias, Steel-Richardson-Olszewski disease (progressive supranuclear palsy), stroke, subarachnoid hemorrhage, subcortical arteriosclerotic encephalopathy, syncopes, tauopathies, tension, thalamic degeneration, thromboembolic or thrombogenic disorders, transient ischemic attacks (TIAs), traumatic brain injury, tubulointerstitial diseases, ulcers, uterine fibroids, vaginal atrophy, valve defects (e.g., mitral valve stenosis, mitral valve regurgitation, insufficiency or incompetence, aortic valve stenosis, aortic valve insufficiency, tricuspic valve insufficiency, pulmonary valve stenosis, pulmonar valve insufficiency, combined valvular defects), vascular disease of the brain, vascular disorder resulting from cardiac and renal complications, vascular leakage or permeability, vasculitis (e.g., thrombotic vasculitis, occlusive thrombotic vasculitis, Kawasaki disease, arteritis, aortitis), vaso-occlusive crisis, venus graft failure, wet age-related macular degeneration and Williams syndrome.

In a specific embodiment of the invention, the disease is selected from, for example, Alzheimer's disease (including pre-Alzheimer's disease, mild to moderate Alzheimer's disease and moderate to severe Alzheimer's disease), dementia (e.g., vascular dementia, post-stroke dementia, Lewy body dementia, dementia with frontal lobe degeneration, dementia with frontotemporal lobar degeneration, dementia with corticobasal degeneration, Creutzfeldt-Jakob dementia, HIV-dementia, multi-infarct dementia, post-operative dementia, strategic single-infarct dementia, HIV-associated dementia (including asymptomatic neurocognitive impairment (ANI), minor neurocognitive disorder (MND), HIV-associated dementia (HAD, also called AIDS dementia complex [ADC] or HIV encephalopathy), pre-senile dementia (mild cognitive impairment, MCI), mixed dementia, Binswanger's dementia (subcortical arteriosclerotic encephalopathy), Parkinson's Dementia); -chronic traumatic encephalopathy (CTE); stroke; -traumatic brain injury; concussion; ischemia (e.g., cerebral ischemia, myocardial ischemia, thromboembolic ischemia, critical limb ischemia), and neuropathies (e.g., peripheral neuropathy, autonomic neuropathy, central nervous system neuropathy, chemotherapy induced neuropathy, diabetic neuropathy, painful neuropathies, neuropathic pain, non-painful neuropathies, painful diabetic neuropathy, non-painful diabetic neuropathy, neuropathies associated to a CNS disease (e.g., Multiple sclerosis, MS), radiation-induced neuropathy), neuropathic pain associated with shingles, neuropathic pain associated with spine surgery).

The term "disease", as used herein refers to any deviation from or interruption of the normal structure or function of any body part, organ, or system that is manifested by a characteristic set of symptoms and signs and whose etiology, pathology, and prognosis may be known or unknown. The term disease encompasses other related terms such as disorder and condition (or medical condition) as well as syndromes, which are defined as a combination of symptoms resulting from a single cause or so commonly occurring together as to constitute a distinct clinical picture. In some embodiments, the term disease refers to an sGC, cGMP and/or NO mediated medical or pathological disease.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a companion animal or pet (e.g., a dog, cat, mice, rats, hamsters, gerbils, guinea pig or rabbit). In some embodiments, the subject is a human.

The invention also provides a method for treating one of the above diseases in a subject, comprising administering a therapeutically effective amount of Form A, Form B, Hydrate 1, Hydrate 2, Hydrate 3, ethanol solvate, methanol solvate, methyl ethyl ketone solvate, dichloromethane solvate, or acetonitrile solvate to the subject in need of the treatment. Alternatively, the invention provides the use of Form A, Form B, Hydrate 1, Hydrate 2, Hydrate 3, ethanol solvate, methanol solvate, methyl ethyl ketone solvate, dichloromethane solvate, or acetonitrile solvate in the treatment of one of these diseases in a subject in need of the treatment. Also included in the invention is the use of Form A, Form B, Hydrate 1, Hydrate 2, Hydrate 3, ethanol solvate, methanol solvate, methyl ethyl ketone solvate, dichloromethane solvate, or acetonitrile solvate for the manufacture of medicament for treating one of the above diseases in a subject in need of the treatment. The invention further provides a method of making or manufacturing a medicament useful for treating one of these diseases comprising using Form A, Form B, Hydrate 1, Hydrate 2, Hydrate 3, ethanol solvate, methanol solvate, methyl ethyl ketone solvate, dichloromethane solvate, or acetonitrile solvate.

The term "biological sample", as used herein, refers to an in vitro or ex vivo sample, and includes, without limitation, cell cultures or extracts thereof, biopsied material obtained from a mammal or extracts thereof, blood, saliva, urine, faeces, semen, tears, lymphatic fluid, ocular fluid, vitreous humour, cerebrospinal fluid (CSF), or other body fluids or extracts thereof.

"Treat", "treating" or "treatment" with regard to a disease, refers to alleviating or abrogating the cause and/or the effects of the disease. In one embodiment, the terms "treat", "treatment" and "treating" refer to the reduction or amelioration of the progression, severity and/or duration of disease, or the amelioration of one or more symptoms of the disease (i.e., "managing" without "curing" the disease). In specific embodiments, the terms "treat"; "treatment" and "treating" refer to the amelioration of at least one measurable physical parameter of a disease. In other embodiments the terms "treat", "treatment" and "treating" refer to the inhibition of the progression of a disease, either physically by, e.g., stabilization of a discernible symptom or physiologically by, e.g., stabilization of a physiological parameter, or both.

The compounds and pharmaceutical compositions described herein can be used alone or in combination therapy for the treatment of a disease mediated, regulated or influenced by sGC, cGMP and/or NO.

In other embodiments, the invention provides a method of stimulating sGC activity in a biological sample, comprising contacting said biological sample with a compound or composition of the invention. Use of a sGC stimulator in a biological sample is useful for a variety of purposes known to one of skill in the art. Examples of such purposes include, without limitation, biological assays and biological specimen storage.

Combination Therapies

As used herein, the terms "in combination" (as in the phrase "in combination therapy") or "co-administration" can be used interchangeably to refer to the use of more than one therapy (e.g., one or more therapeutic agents). The use of the terms does not restrict the order in which therapies (e.g., therapeutic agents) are administered to a subject.

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When used in combination therapy with other agents, a "therapeutically effective amount" of the compounds and pharmaceutical compositions described herein and of the other agent or agents will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed.

In some embodiments, co-administration or combination therapy encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order.

When co-administration involves the separate administration of a first amount of a compound of Formula I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Formula I and the second therapeutic agent can be administered in any order within about 24 hours of each other, within about 16 hours of each other, within about 8 hours of each other, within about 4 hours of each other, within about 1 hour of each other or within about 30 minutes of each other.

Examples of other therapeutic agents that may be combined with Form A, Form B, Hydrate 1, Hydrate 2, Hydrate 3, ethanol solvate, methanol solvate, methyl ethyl ketone solvate, dichloromethane solvate, or acetonitrile solvate either administered separately or in the same pharmaceutical composition include, but are not limited to:

(1) Endothelium-derived releasing factor (EDRF) or NO gas.

(2) NO donors such as a nitrosothiol, a nitrite, a sydnonimine, a NONOate, a N-nitrosamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitrogylcerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; isosorbide (Dilatrate®-SR, Imdur®, Ismo®, Isordil®, Isordil®, Titradose®, Monoket®), 3-morpholinosydnonimine; linsidomine chlorohydrate ("SIN-1"); S-nitroso-N-acetylpenicillamine ("SNAP"); S-nitrosoglutathione (GSNO), sodium nitroprusside, S-nitrosoglutathione mono-ethyl-ester (GSNO-ester), 6-(2-hydroxy-1-methyl-nitrosohydrazino)-N-methyl-1-hexanamine or diethylamine NONOate.

(3) Other substances that enhance cGMP concentrations such as protoporphyrin IX, arachidonic acid and phenyl hydrazine derivatives.

(4) Nitric Oxide Synthase substrates: for example, L-arginine, n-hydroxyguanidine based analogs, such as N[G]-hydroxy-L-arginine (NOHA), 1-(3, 4-dimethoxy-2-chlorobenzylideneamino)-3-hydroxyguanidine, and PR5 (1-(3, 4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-caproic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluoromethyl) propylguanidine.

(5) Compounds which enhance eNOS transcription.

(6) NO independent heme-independent sGC activators, including, but not limited to:
BAY 58-2667 (described in patent publication DE19943635); HMR-1766 (ataciguat sodium, described in patent publication WO2000002851); S 3448 (2-(4-chlorophenylsulfonylamino)-4,5-dimethoxy-N-(4-(thiomorpholine-4-sulfonyl)-phenyl)-benzamide (described in patent publications DE19830430 and WO2000002851); and
HMR-1069 (Sanofi-Aventis).

(7) Heme-dependent, NO-independent sGC stimulators including, but not limited to:
YC-1 (see patent publications EP667345 and DE19744026); riociguat (BAY 63-2521, Adempas®, described in DE19834044); neliciguat (BAY 60-4552, described in WO 2003095451); vericiguat (BAY 1021189); BAY 41-2272 (described in DE19834047 and DE19942809); BAY 41-8543 (described in DE19834044); etriciguat (described in WO 2003086407); CFM-1571 (described in patent publication WO2000027394); A-344905, its acrylamide analogue A-350619 and the aminopyrimidine analogue A-778935;
other sGC stimulators described in one of publications US20090209556, U.S. Pat. No. 8,455,638, US20110118282 (WO2009032249), US20100292192, US20110201621, U.S. Pat. Nos. 7,947,664, 8,053,455 (WO2009094242), US20100216764, U.S. Pat. No. 8,507,512, (WO2010099054) US20110218202 (WO2010065275), US20130012511 (WO2011119518), US20130072492 (WO2011149921), US20130210798 (WO2012058132) and Tetrahedron Letters (2003), 44(48): 8661-8663; and
IW-1973 and IW1701.

(8) Compounds that inhibit the degradation of cGMP and/or cAMP, such as:
PDE1 inhibitors, PDE2 inhibitors, PDE-3 inhibitors such as, for example, marinone, milrinone, enoximone, vesnarinone, pimobendan, and olprinone, PDE4 inhibitors, such as, for example, roflumilast, PDE5 inhibitors, such as, for example, sildenafil (Viagra®) and related agents such as avanafil, lodenafil, mirodenafil, sildenafil citrate (Revatio®), tadalafil (Cialis® or Adcirca®), vardenafil (Levitra®) and udenafil; alprostadil; dipyridamole and PF-00489791; PDE6 inhibitors, PDE9 inhibitors, such as, for example, PF-04447943, PDE10 inhibitors such as, for example, PF-02545920 (PF-10), and PDE11 inhibitors.

(9) Calcium channel blockers of the following types:
dihydropyridine calcium channel blockers such asamlodipine (Norvasc®), aranidipine (Sapresta®), azelnidipine (Calblock®), barnidipine (HypoCa®), benidipine (Coniel®), cilnidipine (Atelec®, Cinalong®, Siscard®), clevidipine (Cleviprex®), diltiazem, efonidipine (Landel®), felodipine (Plendil®), lacidipine (Motens®, Lacipil®), lercanidipine (Zanidip®), manidipine (Calslot®, Madipine®), nicardipine (Cardene®, Carden SR®), nifedipine (Procardia®, Adalat®), nilvadipine (Nivadil®), nimodipine (Nimotop®), nisoldipine (Baymycard®, Sular®, Syscor®), nitrendipine (Cardif®, Nitrepin®, Baylotensin®), pranidipine (Acalas®), and isradipine (Lomir®);
phenylalkylamine calcium channel blockers such as verapamil (Calan®, Isoptin®); and gallopamil (Procorum®, D600);
benzothiazepines such asdiltiazem (Cardizem®); and
nonselective calcium channel inhibitors such as mibefradil, bepridil, fluspirilene, and fendiline.

(10) Endothelin receptor antagonists (ERAs) such as the dual (ETA and ETB) endothelin receptor antagonist bosentan (Tracleer®), sitaxentan (Thelin®) or ambrisentan (Letairis®).

(11) Prostacyclin derivatives or analogues, such asprostacyclin (prostaglandin I2), epoprostenol (synthetic prostacyclin, Flolan®), treprostinil (Remodulin®), iloprost (Ilomedin®), iloprost (Ventavis®); and oral and inhaled forms of Remodulin® under development.

(12) Antihyperlipidemics such as the following types:
bile acid sequestrants like cholestyramine, colestipol, colestilan, colesevelam or sevelamer;
statins like atorvastatin, simvastatin, lovastatin, fluvastatin, pitavastatin, rosuvastatin and pravastatin;
cholesterol absorption inhibitors such as ezetimibe;
other lipid lowering agents such as icosapent ethyl ester, omega-3-acid ethyl esters, reducol;
fibric acid derivatives such as clofibrate, bezafibrate, clinofibrate, gemfibrozil, ronifibrate, binifibrate, fenofibrate, ciprofibrate, choline fenofibrate;
nicotinic acid derivatives such as acipimox and niacin;
combinations of statins, niacin and intestinal cholesterol absorption-inhibiting supplements (ezetimibe and others) and fibrates; and
antiplatelet therapies such as clopidogrel bisulfate.

(13) Anticoagulants, such as the following types:

coumarines (Vitamin K antagonists) such as warfarin (Coumadin®), cenocoumarol, phenprocoumon and phenindione;

heparin and derivatives such as low molecular weight heparin, fondaparinux and idraparinux;

direct thrombin inhibitors such as argatroban, lepirudin, bivalirudin, dabigatran and ximelagatran (Exanta®); and tissue-plasminogen activators, used to dissolve clots and unblock arteries, such as alteplase.

(14) Antiplatelet drugs such as, for instance, topidogrel, ticlopidine, dipyridamoleand aspirin.

(15) ACE inhibitors, for example the following types:

sulfhydryl-containing agents such as captopril (Capoten®) and zofenopril;

dicarboxylate-containing agents such as enalapril (Vasotec/Renitec®), ramipril (Altace®/Tritace®/Ramace®/Ramiwin®), quinapril (Accupril®), perindopril (Coversyl®/Aceon®), lisinopril (Lisodur®/Lopril®/Novatec®/Prinivil®/Zestril®) and benazepril (Lotensin®);

phosphonate-containing agents such as fosinopril;

naturally occurring ACE inhibitors such as casokinins and lactokinins, which are breakdown products of casein and whey that occur naturally after ingestion of milk products, especially cultured milk;

the lactotripeptides Val-Pro-Pro and Ile-Pro-Pro produced by the probiotic *Lactobacillus helveticus* or derived from casein also having ACE-inhibiting and antihypertensive functions;

other ACE inhibitors such as alacepril, delapril, cilazapril, imidapril, trandolapril, temocapril, moexipril and pirapril.

(16) Supplemental oxygen therapy.

(17) Beta blockers, such as the following types:

non-selective agents such as alprenolol, bucindolol, carteolol, carvedilol, labetalol, nadolol, penbutolol, pindolol, oxprenonol, acebutolol, sotalol, mepindolol, celiprolol, arotinolol, tertatolol, amosulalol, nipradilol, propranolol and timolol;

$\beta_1$-Selective agents such as cebutolol, atenolol, betaxolol, bisoprolol, celiprolol, dobutamine hydrochloride, irsogladine maleate, carvedilol, talinolol, esmolol, metoprolol and nebivolol; and $\beta_2$-Selective agents such as butaxamine.

(18) Antiarrhythmic agents such as the following types:

Type I (sodium channel blockers) such as quinidine, lidocaine, phenytoin, propafenone;

Type III (potassium channel blockers) such as amiodarone, dofetilide and sotalol; and Type V such as adenosine and digoxin.

(19) Diuretics such as thiazide diuretics, for example chlorothiazide, chlorthalidone and hydrochlorothiazide, bendroflumethiazide, cyclopenthiazide, methyclothiazide, polythiazide, quinethazone, xipamide, metolazone, indapamide, cicletanine; loop diuretics, such as furosemide and toresamide; potassium-sparing diuretics such as amiloride, spironolactone, canrenoate potassium, eplerenone and triamterene; combinations of these agents; other diuretics such as acetazolamid and carperitide.

(20) Direct-acting vasodilators such as hydralazine hydrochloride, diazoxide, sodium nitroprusside, cadralazine; other vasodilators such as isosorbide dinitrate and isosorbide 5-mononitrate.

(21) Exogenous vasodilators such as Adenocard® and alpha blockers.

(22) Alpha-1-adrenoceptor antagonists such as prazosin, indoramin, urapidil, bunazosin, terazosin and doxazosin; atrial natriuretic peptide (ANP), ethanol, histamine-inducers, tetrahydrocannabinol (THC) and papaverine.

(23) Bronchodilators of the following types:

short acting $\beta_2$ agonists, such as albutamol or albuterol (VentolinID) and terbutaline;

long acting $\beta_2$ agonists (LABAs) such as salmeterol and formoterol;

anticholinergics such as pratropium and tiotropium; and theophylline, a bronchodilator and phosphodiesterase inhibitor.

(24) Corticosteroids such as beclomethasone, methylprednisolone, betamethasone, prednisone, prednisolone, triamcinolone, dexamethasone, fluticasone, flunisolide, hydrocortisone, and corticosteroid analogs such as budesonide.

(25) Dietary supplements such as, for example omega-3 oils; folic acid, niacin, zinc, copper, Korean red ginseng root, ginkgo, pine bark, *Tribulus terrestris*, arginine, *Avena sativa*, horny goat weed, maca root, muira puama, saw palmetto, and Swedish flower pollen; vitamin C, Vitamin E, Vitamin K2; testosterone supplements, testosterone transdermal patch; zoraxel, naltrexone, bremelanotide and melanotan II.

(26) PGD2 receptor antagonists.

(27) Immunosuppressants such as cyclosporine (cyclosporine A, Sandimmune®, Neoral®), tacrolimus (FK-506, Prograf®), rapamycin (Sirolimus®, Rapamune®) and other FK-506 type immunosuppressants, mycophenolate, e.g., mycophenolate mofetil (CellCept®).

(28) Non-steroidal anti-asthmatics such as $\beta_2$-agonists like terbutaline, metaproterenol, fenoterol, isoetharine, albuterol, salmeterol, bitolterol and pirbuterol; $\beta_2$-agonist-corticosteroid combinations such as salmeterol-fluticasone (Advair®), formoterol-budesonide (Symbicort®), theophylline, cromolyn, cromolyn sodium, nedocromil, atropine, ipratropium, ipratropium bromide and leukotriene biosynthesis inhibitors (zileuton, BAY1005).

(29) Non-steroidal anti-inflammatory agents (NSAIDs) such as propionic acid derivatives like alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives such as indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac; fenamic acid derivatives such as flufenamic acid, meclofenamic acid, mefenamic acid, niflumic acid and tolfenamic acid; biphenylcarboxylic acid derivatives such as diflunisal and flufenisal; oxicams such as isoxicam, piroxicam, sudoxicam and tenoxican; salicylates such as acetyl salicylic acid and sulfasalazine; and the pyrazolones such as apazone, bezpiperylon, feprazone, mofebutazone, oxyphenbutazone and phenylbutazone.

(30) Cyclooxygenase-2 (COX-2) inhibitors such as celecoxib (Celebrex®), rofecoxib (Vioxx®), valdecoxib, etoricoxib, parecoxib and lumiracoxib; opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine;

(31) Anti-diabetic agents such as insulin and insulin mimetics; sulfonylureas such as glyburide, glybenclamide, glipizide, gliclazide, gliquidone, glimepiride, meglinatide, tolbutamide, chlorpropamide, acetohexamide and olazamide; biguanides such as metformin (Glucophage®); α-glucosidase inhibitors such as acarbose, epalrestat, voglibose, miglitol; thiazolidinone compounds such as rosiglitazone (Avandia®), troglitazone (Rezulin®), ciglitazone, pioglitazone (Actos®) and englitazone; insulin sensitizers such as pioglitazone and rosiglitazone; insulin secretagogues such as repaglinide, nateglinide and mitiglinide; incretin mimetics such as exanatide and liraglutide; amylin analogues such as pramlintide; glucose lowering agents such as chromium picolinate, optionally combined with biotin; dipeptidyl peptidase IV inhibitors such as sitagliptin, vildagliptin, saxagliptin, alogliptin and linagliptin.

(32) HDL cholesterol-increasing agents such as anacetrapib and dalcetrapib.

(33) Antiobesity drugs such as methamphetamine hydrochloride, amfepramone hydrochloride (Tenuate®), phentermine (Ionamin®), benzfetamine hydrochloride (Didrex®), phendimetrazine tartrate (Bontril®, Prelu-2 ®, Plegine®), mazindol (Sanorex®), orlistat (Xenical®), sibutramine hydrochloride monohydrate (Meridia®, Reductil®), rimonabant (Acomplia®), amfepramone, chromium picolinate; combination such as phentermine/topiramate, bupropion/naltrexone, sibutramine/metformin, bupropion SR/zonisamide SR, salmeterol, xinafoate/fluticasone propionate; lorcaserin hydrochloride, phentermine/topiramate, cetilistat, exenatide, liraglutide, metformin hydrochloride, sibutramine/metformin, bupropion SR/zonisamide SR, CORT-108297, canagliflozin, chromium picolinate, GSK-1521498, LY-377604, metreleptin, obinepitide, P-57AS3, PSN-821, salmeterol xinafoate/fluticasone propionate, sodium tungstate, somatropin (recombinant), tesamorelin, tesofensine, velneperit, zonisamide, beloranib hemioxalate, insulinotropin, resveratrol, sobetirome, tetrahydrocannabivarin and beta-lapachone.

(34) Angiotensin receptor blockers such as losartan, valsartan, candesartan, cilexetil, eprosaran, irbesartan, telmisartan, olmesartran, medoxomil, azilsartan and medoxomil.

(35) Renin inhibitors such as aliskiren hemifumirate.

(36) Centrally acting alpha-2-adrenoceptor agonists such as methyldopa, clonidine and guanfacine.

(37) Adrenergic neuron blockers such as guanethidine and guanadrel.

(38) Imidazoline I-1 receptor agonists such as rimenidine dihydrogen phosphate and moxonidine hydrochloride hydrate.

(39) Aldosterone antagonists such as spironolactone and eplerenone.

(40) Potassium channel activators such as pinacidil.

(41) Dopamine D1 agonists such as fenoldopam mesilate; other dopamine agonists such as ibopamine, dopexamine and docarpamine.

(42) 5-HT2 antagonists such as ketanserin.

(43) Vasopressin antagonists such as tolvaptan.

(44) Calcium channel sensitizers such as levosimendan or activators such as nicorandil.

(45) Adenylate cyclase activators such as colforsin dapropate hydrochloride.

(46) Positive inotropic agents such as digoxin and metildigoxin; metabolic cardiotonic agents such as ubidecarenone; brain natriuretic peptides such as nesiritide.

(47) Drugs used for the treatment of erectile dysfunction such as alprostadil, aviptadil, and phentolamine mesilate.

(48) Drugs used in the treatment of obesity, including but not limited to, methamphetamine hydrochloride (Desoxyn®), amfepramone hydrochloride (Tenuate®), phentermine (Ionamin®), benzfetamine hydrochloride (Didrex®), phendimetrazine hydrochloride (Bontril®, Prelu-2®, Plegine®), mazindol (Sanorex®) and orlistat (Xenical®).

(49) Drugs used for the treatment of Alzheimer's disease and dementias such as the following types: acetyl cholinesterase inhibitors including galantamine (Razadyne®), rivastigmine (Exelon®), donepezil (Aricept®) and tacrine (Cognex®); NMDA receptor antagonists such as memantine (Namenda®); and oxidoreductase inhibitors such as idebenone.

(50) Psychiatric medications such as the following types:
ziprasidone (Geodon™), risperidone (Risperdal™), olanzapine (Zyprexa™), valproate;
dopamine D4 receptor antagonists such as clozapine;
dopamine D2 receptor antagonists such as nemonapride;
mixed dopamine D1/D2 receptor antagonists such as zuclopenthixol;
GABA A receptor modulators such as carbamazepine;
sodium channel inhibitors such as lamotrigine;
monoamine oxidase inhibitors such as moclobemide and indeloxazine; and
primavanserin, and perospirone.

(51) Drugs used for the treatment of movement disorders or symptoms such as the following types:
catechol-O-methyl transferase inhibitors such as entacapone;
monoamine oxidase B inhibitors such as selegiline;
dopamine receptor modulators such as levodopa;
dopamine D3 receptor agonists such as pramipexole;
decarboxylase inhibitors such as carbidopa;
other dopamine receptor agonists such as pergolide, ropinirole, cabergoline;
ritigonide, istradefylline, talipexole; zonisamide and safinamide; and
synaptic vesicular amine transporter inhibitors such as tetrabenazine.

(52) Drugs used for the treatment of mood or affective disorders or OCD such as the following types:
tricyclic antidepressants such as amitriptyline (Elavil®), desipramine (Norpramin®), imipramine (Tofranil®), amoxapine (Asendin®), nortriptyline and clomipramine;
selective serotonin reuptake inhibitors (SSRIs) such as paroxetine (Paxil®), fluoxetine (Prozac®), sertraline (Zoloft®), and citralopram (Celexa®);
doxepin (Sinequan®), trazodone (Desyrel®) and agomelatine;
selective norepinephrine reuptake inhibitors (SNRIs) such as venlafaxine, reboxetine and atomoxetine; dopaminergic antidepressants such as bupropion and amineptine.

(53) Drugs for the enhancement of synaptic plasticity such as the following types:
nicotinic receptor antagonists such as mecamylamine; and
mixed 5-HT, dopamine and norepinephrine receptor agonists such as lurasidone.

(54) Drugs used for the treatment of ADHD such as amphetamine; 5-HT receptor modulators such as vortioxetine and alpha-2 adrenoceptor agonists such as clonidine.

(55) Neutral endopeptidase (NEP) inhibitors such as sacubitril, omapatrilat; and Methylene blue (MB).

(56) Nitric oxide synthase cofactors such as: tetrahydrobiopterin, dihydrobiopterin, and sapropterin (Kuvan®)

Packaging and Kits

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

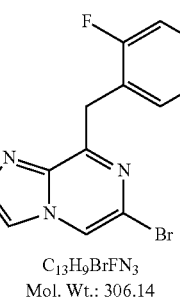

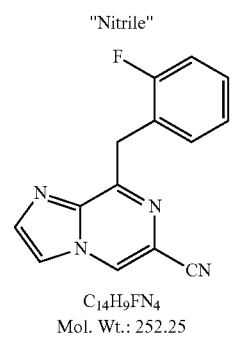

EXEMPLIFICATION

Preparation of and Characterization of 8-(2-fluorobenzyl)-6-(3-(trifluoromethyl)-1H-1,2,4-triazol-5-yl)imidazo[1,2-a]pyrazine Form A Synthesis of 8-(2-Fluorobenzyl)imidazo[1,2-a]pyrazine-6-carbonitrile (Nitrile)

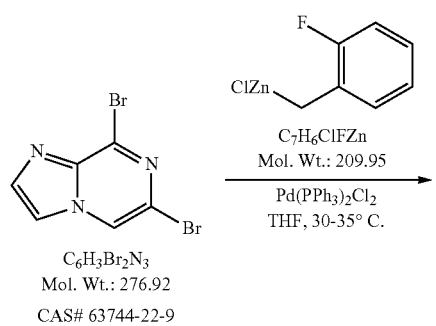

The title compound was synthesized in 2 steps according to a patent literature procedure (WO2015/187470A1) as a yellow solid (0.60 g, 39% yield over 2 steps). $^1$H NMR (500 MHz, Methanol-$d_4$) δ (ppm) 9.09 (s, 1H), 8.14 (s, 1H), 7.91 (s, 1H), 7.35 (t, 1H), 7.28 (m, 1H), 7.10 (m, 2H), 4.60 (s, 2H).

Synthesis of tert-butyl 2-((8-(2-fluorobenzyl)imidazo[1,2-a]pyrazin-6-yl)(imino)methyl)hydrazine-1-carboxylate (BOC-Amidrazone)

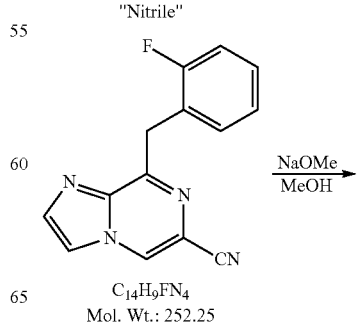

7.25-7.33 (m, 1H), 7.42 (t, J=7.63 Hz, 1H), 7.82 (s, 1H), 8.29 (s, 1H), 9.00-9.09 (m, 1H), 9.13 (br s, 1H).

$^{13}$C-NMR (D$_6$-DMSO): δ ppm 28.15, 31.91, 78.44, 115.04, 116.28, 116.50, 124.14, 124.37, 128.56, 131.58, 131.79, 135.40, 139.09, 142.53, 149.66, 152.87, 160.39.

Synthesis of 8-(2-fluorobenzyl)-6-(3-(trifluoromethyl)-1H-1,2,4-triazol-5-yl)imidazo[1,2-a]pyrazine (compound of Formula (I))

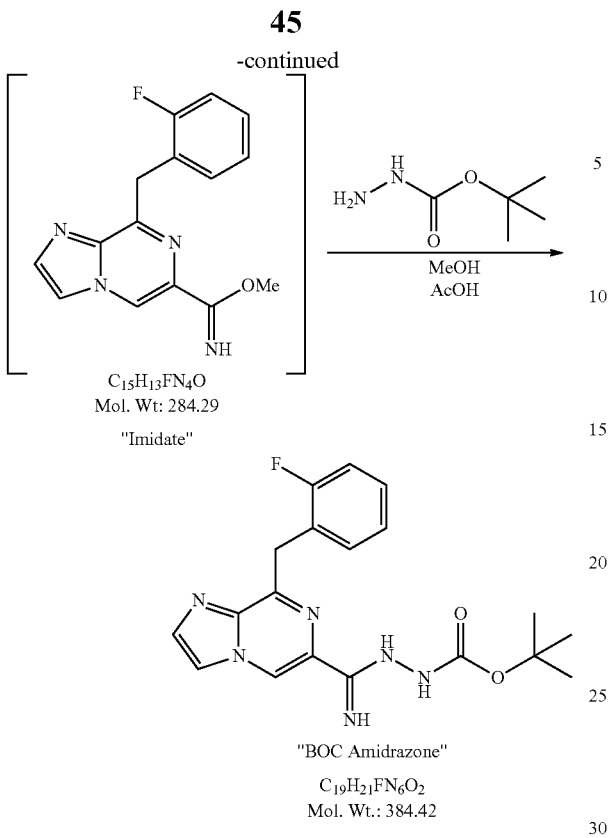

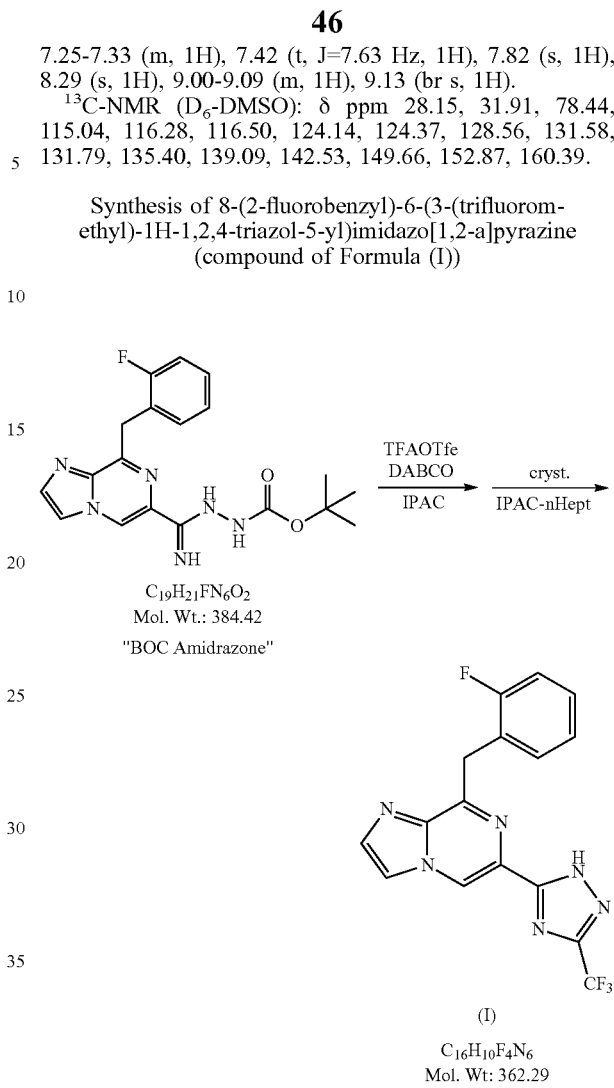

Charged 1 mol (252.25 g) of the Nitrile compound to a 2 L cylindrical reactor equipped with a mechanical stirrer, followed by dry methanol (1.5 L). Stirred at 120-140 RPM to give an ochre, grainy suspension. To the suspension, 5 mol % (100 mL 0.5M soln.) sodium methoxide in methanol was added at room temperature. The reactor jacket temperature was set to 18° C. and the mixture was stirred under nitrogen until HPLC indicated complete conversion to the intermediate methyl imidate (LC-MS: 100A % MH$^+$ 285). 1.03 eq (136 g) t-butyl carbazate was then added in portions over 15 min. Temperature dropped to 9.2° C. and acetic acid (0.1 eq., 5.7 mL) was added slowly via syringe through septum. The temperature of the reaction mixture slowly raised from 11.2° C. to 17.2° C., resulting in a clear, coffee-brown solution. The reactor acket temperature was raised to 18° C. and the stirring rate was increased to 165 RPM. After 1 h, a very thick yellow suspension was formed (temperature of the reaction mixture at ~21° C.). Additional dry MeOH (550 mL) was then added. After ~24 h, LC-MS indicated complete conversion to the BOC-Amidrazone (MH$^+$ 385) with no methyl imidate detectable by LC-MS. The suspension was cooled to 8-10° C. and 0.06 eq. (60 mL) 1M aq. NaOH was added, followed by sat. aq. NaCl (150 mL) and DI water (200 mL). The resulting mixture was stirred for several hours, before adjusting the pH to 8-9 with 10% aq. sodium carbonate. The resulting mixture was then diluted with water (250 mL) and filtered over a 2 L medium poros. glass frit, washed with DI water (3×300 mL), and suction dried on the filter for ~45 min. The wetcake was washed with n-heptane (4×200 mL) and suction-dried on the filter for 1 h, then dried to constant weight in the vacuum drying oven at 40° C. The product was obtained as a light yellow, powdery material 358.86 g (93%). Mp (DSC) 181° C. HPLC (RP) [240 nm]: 99.8 A %. MS: MH+ 385 (100%).

$^1$H-NMR (D$_6$-DMSO): δ ppm 1.47 (s, 9H), 4.56 (s, 2H), 6.34 (s, 2H), 7.12 (t, J=7.48 Hz, 1H), 7.15-7.21 (m, 1H), Charged 50 mmol (19.22 g) of the BOC-Amidrazone and 2.2 eq. DABCO (12.34 g) into a 500 ml pear shape flask with a magnetic stir bar. Isopropyl acetate (300 mL) was then added and the mixture was stirred under nitrogen for 2 min at room temp, resulting in a white, thin suspension. To the suspension trifluoroethyl trifluoroacetate (2.5 eq., 25 g) was added, and the suspension was stirred at room temp. under nitrogen until HPLC & LC-MS showed complete conversion of the starting material. The resulting suspension was washed sequentially with saturated aqueous sodium bicarbonate, saturated aqueous sodium chloride and distilled water. The organic phase was filtered over a short silica gel/celite plug and concentrated to a small volume (~50-70 mL) at the rotavap. (waterbath temp.: 45-50° C.). The warm suspension was immediately diluted with n-heptane (150 mL), stirred for 2 hours while slowly cooling to 20°, and then stirred for another 2 hours to 5°, and filtered. The wet cake was washed with n-heptane (2×50 mL) and dried in the vacuum drying oven to constant weight. Form A was obtained as snowy white powder 16.7 g (92%). Mp (DSC) 196° C. HPLC (RP) [240 nm]: 99.8 A %. MS: MH+ 363 (100%).

$^1$H-NMR (D$_6$-DMSO): δ ppm 4.60 (s, 2H) 7.05-7.11 (m, 1H) 7.14-7.20 (m, 1H) 7.22-7.29 (m, 1H) 7.43 (br t, J=7.63 Hz, 1H) 7.84-7.87 (m, 1H) 8.23-8.27 (m, 1H) 9.44 (d, J=1.83 Hz, 1H) 15.43 (br s, 1H).

$^{13}$C-NMR (D$_6$-DMSO): δ ppm 160.90, 158.95, 154.13, 152.73, 152.43, 151.76, 138.89, 135.50, 130.91, 130.87, 128.34, 128.27, 126.39, 124.11, 124.02, 122.47, 120.33, 119.12, 118.18, 116.68, 116.04, 115.01, 114.84, 31.64, 31.61.

$^{19}$F-NMR (D$_6$-DMSO): δ ppm −116.96,−63.93.

Form A can also be made by slurring (e.g., mixing the compound with a solvent and stirring continuously) the compound of Formula (I) using a mixture of isopropyl acetate (IPAC) and n-heptane, where the n-heptane makes up more than 50% by volume of the composition for 24 hours to 1 week at room temperature. Form A is also formed when 8-(2-fluorobenzyl)-6-(3-(trifluoromethyl)-1H-1,2,4-triazol-5-yl)imidazo[1,2-a]pyrazine is suspended or recrystallized in the 100% n-heptane or cyclohexane.

Form B 8-(2-fluorobenzyl)-6-(3-(trifluoromethyl)-1H-1,2,4-triazol-5-yl)imidazo[1,2-a]pyrazine Form B was synthesized by slurring 8-(2-fluorobenzyl)-6-(3-(trifluoromethyl)-1H-1,2,4-triazol-5-yl)imidazo[1,2-a]pyrazine Form A in isopropyl acetate (IPAC) for 24 hours to 1 week at room temperature. Alternative solvents that can be used in this method include (a) isopropyl alcohol (IPA); (b) IPA/IPAC mixtures; (c) mixtures of IPAC and hexane with IPAC making up 50% or more by volume of the composition; and (d) tetrahydrofuran.

Hydrate 1

8-(2-fluorobenzyl)-6-(3-(trifluoromethyl)-1H-1,2,4-triazol-5-yl)imidazo[1,2-a]pyrazine Hydrate 1 was isolated by slurring anhydrous 8-(2-fluorobenzyl)-6-(3-(trifluoromethyl)-1H-1,2,4-triazol-5-yl)imidazo[1,2-a]pyrazine (either Form A or Form B) in 100% water for 24 hours to 1 week at room temperature.

Hydrate 2

8-(2-fluorobenzyl)-6-(3-(trifluoromethyl)-1H-1,2,4-triazol-5-yl)imidazo[1,2-a]pyrazine Hydrate 2 was crystallized by slurring anhydrous 8-(2-fluorobenzyl)-6-(3-(trifluoromethyl)-1H-1,2,4-triazol-5-yl)imidazo[1,2-a]pyrazine (either Form A or Form B) in aqueous mixtures containing cellulose-based polymers such as methylcellulose and/or surfactants such as Tween 80 and sodium lauryl sulfate for 24 hours to 1 week at room temperature. Hydrate 2 can also be crystallized out of aqueous solutions containing 10% of organic solvents such as isopropyl alcohol.

Hydrate 3

8-(2-fluorobenzyl)-6-(3-(trifluoromethyl)-1H-1,2,4-triazol-5-yl)imidazo[1,2-a]pyrazine Hydrate 3 was prepared by suspending anhydrous 8-(2-fluorobenzyl)-6-(3-(trifluoromethyl)-1H-1,2,4-triazol-5-yl)imidazo[1,2-a]pyrazine (either Form A or Form B) in a mixture of IPA containing up to 50% of moisture or water. The mixture was slurred over a 24-hour period, filtered and the residual solids dried under vacuum at room temperature.

Ethanol Solvate

Ethanol solvate was isolated by slurring 8-(2-fluorobenzyl)-6-(3-(trifluoromethyl)-1H-1,2,4-triazol-5-yl)imidazo[1,2-a]pyrazine (either Form A or Form B) in 100% ethanol for 24 hours to 1 week at room temperature.

Methanol Solvate

Methanol solvate was isolated by slurring 8-(2-fluorobenzyl)-6-(3-(trifluoromethyl)-1H-1,2,4-triazol-5-yl)imidazo[1,2-a]pyrazine (either Form A or Form B) in 100% methanol for 24 hours to 1 week at room temperature.

Methyl Ethyl Ketone Solvate

Methyl ethyl ketone solvate was isolated by slurring 8-(2-fluorobenzyl)-6-(3-(trifluoromethyl)-1H-1,2,4-triazol-5-yl)imidazo[1,2-a]pyrazine (either Form A or Form B) in 100% methyl ethyl ketone for 24 hours to 1 week at room temperature.

Dichloromethane Solvate Dichloromethane (DCM) solvate was isolated by slurring 8-(2-fluorobenzyl)-6-(3-(trifluoromethyl)-1H-1,2,4-triazol-5-yl)imidazo[1,2-a]pyrazine (either Form A or Form B) in 100% DCM for 24 hours to 1 week at room temperature.

Acetonitrile Solvate

Acetonitrile (ACN) solvate was isolated by slurring 8-(2-fluorobenzyl)-6-(3-(trifluoromethyl)-1H-1,2,4-triazol-5-yl) imidazo[1,2-a]pyrazine (either Form A or Form B) in 100% ACN for 24 hours to 1 week at room temperature.

Ethyl Acetate Solvate

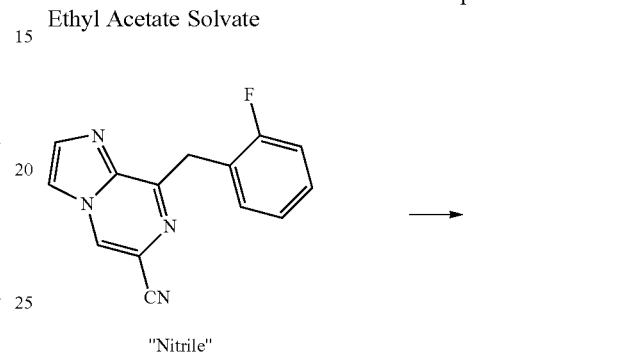

To a solution of the Nitrile compound (4.0 g, 16 mmol) in methanol (40 mL) was added anhydrous hydrazine (3.1 mL, 100 mmol). After stirring at ambient temperature overnight, complete disappearance of starting material was observed. The reaction was concentrated in vacuo, residual hydrazine was removed with methanol and toluene chasing, and the resultant foam was dried under vacuum overnight. The brown foam was taken up in DCM (75 mL) and 2,2,2-trifluoroacetic anhydride (3.8 ml, 27 mmol) was added dropwise to prevent a strong exothermic reaction. The reaction was stirred at ambient temperature until complete consumption of the amidrazone intermediate. The solvent was removed in vacuo and dried to a yellow residue. The residue was taken up in AcOH (10 mL) and EtOH (100 mL) and heated at 90° C. for 1 hour. The reaction mixture was cooled to ambient temperature and concentrated to half the reaction volume. The resultant thick suspension was filtered, and the filtrate was concentrated to brown oil. The crude material was purified using silica gel chromatography (10-100% EtOAc/hexanes gradient) to isolate the ethyl acetate solvate (4.0 g, 69% yield) as a tan solid.

$^1$H NMR (500 MHz, DMSO-d) δ (ppm) 15.46 (s, 1H), 9.45 (s, 1H), 8.26 (s, 1H), 7.87 (s, 1H), 7.43 (t, 1H), 7.22-7.32 (m, 1H), 7.14-7.22 (m, 1H), 7.09 (t, 1H), 4.60 (s, 2H).

LCMS [M+H]=363.1

Alternatively, the ethyl acetate solvate was isolated by slurring 8-(2-fluorobenzyl)-6-(3-(trifluoromethyl)-1H-1,2,4-triazol-5-yl)imidazo[1,2-a]pyrazine (either Form A or Form B) in 100% ethyl acetate for 24 hours to 1 week at room temperature.

X-Ray Powder Diffraction

For FIGS. 1A, 5A, 8A, 11A, 14A, 17, 19, 21, 22, 24, and 26, the XRPD patterns were acquired at room temperature in reflection mode using a Bruker D8 Discover system equipped with a sealed tube source and a Hi-Star area detector (Bruker AXS, Madison, Wis.). The X-Ray generator was operated at a voltage of 40 kV and a current of 40 mA. The powder sample was placed in a low-background holder. The data was subsequently integrated over the range of 5.000°-45.000° 2θ with a step size of 0.020° and merged into one continuous pattern. The X-ray powder diffraction pattern is made using CuKα1 radiation (Cu wavelength of 1.54060 nm).

For FIG. 1B, 5B, 8B, 11B, 14B, the XRPD patterns are acquired at room temperature in reflection mode using a Panalytical Empyrean system equipped with a sealed tube source and a PIXcel$^{1D}$ detector. The X-Ray generator is operated at a voltage of 45 kV and a current of 40 mA. The powder sample is placed in a zero-background holder. The data is subsequently integrated over the range of 4.0°-40.0° 2θ with a step size of 0.0260 and merged into one continuous pattern. The X-ray powder diffraction pattern is made using CuKα1 radiation (Cu wavelength of 1.54060 nm).

Figure 26:
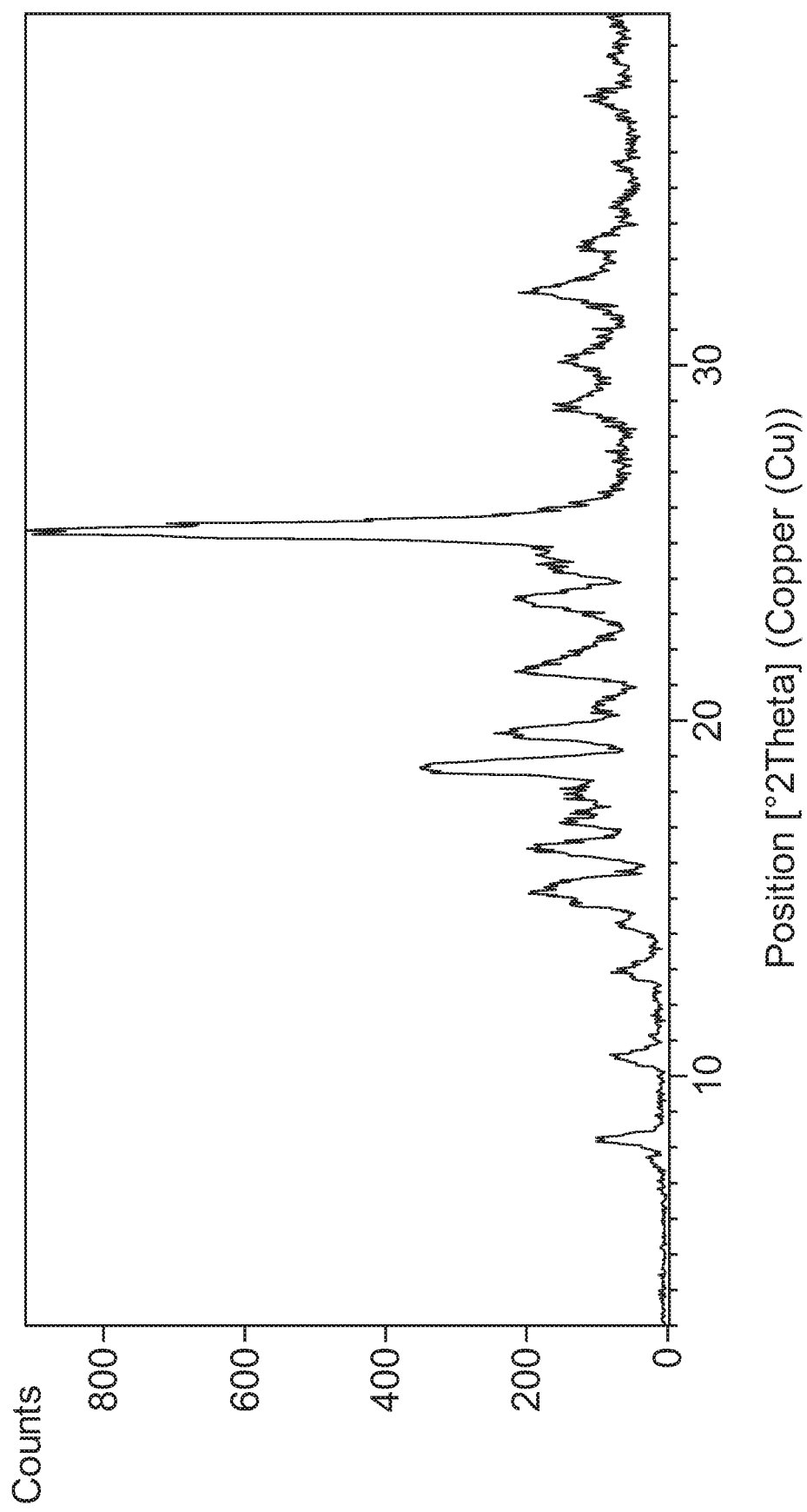
FIG. 26 is a XRPD pattern of 8-(2-fluorobenzyl)-6-(3-(trifluoromethyl)-1H-1,2,4-triazol-5-yl)imidazo[1,2-a]pyrazine ethyl acetate solvate, acquired at room temperature in reflection mode using a Bruker D8 Discover system.

The X-ray powder diffraction pattern (XRPD) of 8-(2-fluorobenzyl)-6-(3-(trifluoromethyl)-1H-1,2,4-triazol-5-yl)imidazo[1,2-a]pyrazine Form A is shown in FIG. 1A. The X-ray powder diffraction pattern (XRPD) of 8-(2-fluorobenzyl)-6-(3-(trifluoromethyl)-1H-1,2,4-triazol-5-yl)imidazo[1,2-a]pyrazine Form A is shown in FIG. 1B. The XRPD pattern of 8-(2-fluorobenzyl)-6-(3-(trifluoromethyl)-1H-1,2,4-triazol-5-yl)imidazo[1,2-a]pyrazine Form B is shown in FIG. 5A. The XRPD pattern of 8-(2-fluorobenzyl)-6-(3-(trifluoromethyl)-1H-1,2,4-triazol-5-yl)imidazo[1,2-a]pyrazine Form B is shown in FIG. 5B. The XRPD pattern of 8-(2-fluorobenzyl)-6-(3-(trifluoromethyl)-1H-1,2,4-triazol-5-yl)imidazo[1,2-a]pyrazine Hydrate 1 is shown in FIG. 8A. The XRPD pattern of 8-(2-fluorobenzyl)-6-(3-(trifluoromethyl)-1H-1,2,4-triazol-5-yl)imidazo[1,2-a]pyrazine Hydrate 1 is shown in FIG. 8B. The XRPD pattern of 8-(2-fluorobenzyl)-6-(3-(trifluoromethyl)-1H-1,2,4-triazol-5-yl)imidazo[1,2-a]pyrazine Hydrate 2 is shown in FIG. 11A. The XRPD pattern of 8-(2-fluorobenzyl)-6-(3-(trifluoromethyl)-1H-1,2,4-triazol-5-yl)imidazo[1,2-a]pyrazine Hydrate 2 is shown in FIG. 11B. The XRPD pattern of 8-(2-fluorobenzyl)-6-(3-(trifluoromethyl)-1H-1,2,4-triazol-5-yl)imidazo[1,2-a]pyrazine Hydrate 3 is shown in FIG. 14A. The XRPD pattern of 8-(2-fluorobenzyl)-6-(3-(trifluoromethyl)-1H-1,2,4-triazol-5-yl)imidazo[1,2-a]pyrazine Hydrate 3 is shown in FIG. 14B. The XRPD pattern of 8-(2-fluorobenzyl)-6-(3-(trifluoromethyl)-1H-1,2,4-triazol-5-yl)imidazo[1,2-a]pyrazine Ethanol Solvate is shown in FIG. 17. The XRPD pattern of 8-(2-fluorobenzyl)-6-(3-(trifluoromethyl)-1H-1,2,4-triazol-5-yl)imidazo[1,2-a]pyrazine Methanol Solvate is shown in FIG. 19. The XRPD pattern of 8-(2-fluorobenzyl)-6-(3-(trifluoromethyl)-1H-1,2,4-triazol-5-yl)imidazo[1,2-a]pyrazine Methyl Ethyl Solvate is shown in FIG. 21. The XRPD pattern of 8-(2-fluorobenzyl)-6-(3-(trifluoromethyl)-1H-1,2,4-triazol-5-yl)imidazo[1,2-a]pyrazine Dichloromethane Solvate is shown in FIG. 22. The XRPD pattern of 8-(2-fluorobenzyl)-6-(3-(trifluoromethyl)-1H-1,2,4-triazol-5-yl)imidazo[1,2-a]pyrazine Acetonitrile Solvate is shown in FIG. 24. The XRPD pattern of 8-(2-fluorobenzyl)-6-(3-(trifluoromethyl)-1H-1,2,4-triazol-5-yl)imidazo[1,2-a]pyrazine ethyl acetate solvate is shown in FIG. 26.

TABLE 1A

XRPD peak list for 8-(2-fluorobenzyl)-6-(3-(trifluoromethyl)-1H-1,2,4-triazol-5-yl)imidazo[1,2-a]pyrazine Form A, acquired at room temperature in reflection mode using a Bruker D8 Discover system described above.

| Pos. [°2Th.] | Rel. Int. [%] |
|---|---|
| 4.9 | 30.23 |
| 7.0 | 47.45 |
| 8.3 | 70.53 |
| 10.6 | 19.37 |
| 11.1 | 46.04 |
| 14.3 | 32.81 |
| 15.0 | 100.00 |
| 15.9 | 31.97 |
| 16.7 | 44.41 |
| 17.6 | 52.26 |
| 18.2 | 32.66 |
| 19.1 | 80.49 |
| 19.7 | 28.22 |
| 20.2 | 46.45 |
| 21.6 | 25.63 |
| 23.2 | 49.29 |
| 24.9 | 62.00 |
| 25.8 | 62.32 |
| 27.1 | 13.02 |
| 28.2 | 11.48 |
| 28.8 | 14.15 |
| 29.9 | 23.42 |
| 30.8 | 18.52 |
| 32.1 | 19.45 |
| 33.1 | 13.93 |

TABLE 1B

XRPD peak list for 8-(2-fluorobenzyl)-6-(3-(trifluoromethyl)-1H-1,2,4-triazol-5-yl)imidazo[1,2-a]pyrazine Form A, acquired at room temperature in reflection mode using a Panalytical Empyrean system described above.

| Pos. [°2Th.] | Rel. Int. [%] |
|---|---|
| 5.0 | 9.0 |
| 7.0 | 38.5 |
| 7.2 | 28.2 |
| 8.3 | 75.6 |
| 8.5 | 60.0 |
| 10.4 | 5.9 |
| 10.8 | 11.9 |
| 11.3 | 32.4 |
| 12.4 | 3.3 |
| 14.2 | 12.1 |
| 14.4 | 18.7 |
| 14.6 | 18.2 |
| 15.0 | 71.3 |
| 15.2 | 100.0 |
| 16.2 | 15.9 |
| 17.0 | 19.3 |
| 17.8 | 35.5 |

TABLE 1B-continued

XRPD peak list for 8-(2-fluorobenzyl)-6-(3-(trifluoromethyl)-1H-1,2,4-triazol-5-yl)imidazo[1,2-a]pyrazine Form A, acquired at room temperature in reflection mode using a Panalytical Empyrean system described above.

| Pos. [°2Th.] | Rel. Int. [%] |
|---|---|
| 18.5 | 13.7 |
| 19.3 | 55.0 |
| 19.9 | 18.9 |
| 20.3 | 10.1 |
| 21.6 | 19.4 |
| 22.0 | 20.3 |
| 22.2 | 20.7 |
| 22.6 | 11.1 |
| 22.9 | 12.4 |
| 23.4 | 17.9 |
| 24.2 | 5.8 |
| 25.1 | 14.8 |
| 25.7 | 10.5 |
| 25.9 | 18.3 |
| 26.4 | 6.2 |
| 27.4 | 5.4 |
| 28.4 | 2.9 |
| 29.0 | 4.0 |
| 29.6 | 8.5 |
| 30.1 | 10.2 |
| 30.2 | 10.9 |
| 31.0 | 6.6 |
| 31.8 | 5.1 |
| 32.2 | 7.3 |
| 33.3 | 3.1 |
| 33.7 | 3.8 |
| 36.2 | 1.6 |
| 36.7 | 2.0 |

TABLE 2A

XRPD peak list for 8-(2-fluorobenzyl)-6-(3-(trifluoromethyl)-1H-1,2,4-triazol-5-yl)imidazo[1,2-a]pyrazine Form B, acquired at room temperature in reflection mode using a Bruker D8 Discover system described above.

| Pos. [°2Th.] | Rel. Int. [%] |
|---|---|
| 8.9 | 16.29 |
| 12.2 | 17.12 |
| 13.6 | 62.32 |
| 14.5 | 19.67 |
| 15.7 | 24.94 |
| 17.2 | 89.17 |
| 17.7 | 60.76 |
| 18.3 | 69.22 |
| 21.0 | 100 |
| 22.7 | 48.88 |
| 23.9 | 54.19 |
| 24.2 | 61.07 |
| 25.0 | 30.21 |
| 25.6 | 16.4 |
| 26.7 | 20.59 |
| 27.6 | 49.89 |
| 29.6 | 25.3 |

TABLE 2B

XRPD peak list for 8-(2-fluorobenzyl)-6-(3-(trifluoromethyl)-1H-1,2,4-triazol-5-yl)imidazo[1,2-a]pyrazine Form B, acquired at room temperature in reflection mode using a Panalytical Empyrean system described above.

| Pos. [°2Th.] | Rel. Int. [%] |
|---|---|
| 8.5 | 7.9 |
| 9.1 | 30.7 |
| 10.9 | 11.7 |

TABLE 2B-continued

XRPD peak list for 8-(2-fluorobenzyl)-6-(3-(trifluoromethyl)-1H-1,2,4-triazol-5-yl)imidazo[1,2-a]pyrazine Form B, acquired at room temperature in reflection mode using a Panalytical Empyrean system described above.

| Pos. [°2Th.] | Rel. Int. [%] |
|---|---|
| 12.4 | 25.2 |
| 13.8 | 67.2 |
| 14.6 | 16.1 |
| 14.8 | 24.9 |
| 15.7 | 19.5 |
| 16.0 | 33.7 |
| 17.4 | 100.0 |
| 18.0 | 53.2 |
| 18.2 | 12.9 |
| 18.5 | 58.9 |
| 20.4 | 11.5 |
| 21.2 | 83.4 |
| 22.1 | 12.9 |
| 22.6 | 4.2 |
| 22.9 | 36.7 |
| 23.5 | 7.6 |
| 24.1 | 45.4 |
| 24.5 | 48.3 |
| 25.2 | 26.4 |
| 25.7 | 12.4 |
| 25.9 | 18.6 |
| 26.8 | 12.0 |
| 27.1 | 23.6 |
| 27.8 | 42.6 |
| 28.8 | 4.9 |
| 29.4 | 4.6 |
| 29.7 | 9.3 |
| 30.0 | 13.1 |
| 31.1 | 4.6 |
| 31.6 | 4.1 |
| 32.3 | 6.2 |
| 33.5 | 4.4 |
| 34.0 | 4.6 |
| 35.2 | 1.4 |
| 35.7 | 4.7 |
| 36.8 | 2.0 |
| 38.0 | 4.8 |

TABLE 3A

XRPD peak list for 8-(2-fluorobenzyl)-6-(3-(trifluoromethyl)-1H-1,2,4-triazol-5-yl)imidazo[1,2-a]pyrazine Hydrate 1, acquired at room temperature in reflection mode using a Bruker D8 Discover system described above.

| Pos. [°2Th.] | Rel. Int. [%] |
|---|---|
| 9.1 | 7.5 |
| 11.5 | 100.0 |
| 13.5 | 11.7 |
| 15.2 | 63.5 |
| 17.0 | 88.4 |
| 17.7 | 46.7 |
| 18.3 | 86.7 |
| 19.1 | 36.4 |
| 20.1 | 8.2 |
| 22.1 | 18.3 |
| 23.1 | 30.9 |
| 23.3 | 51.0 |
| 24.2 | 31.7 |
| 24.9 | 74.3 |
| 25.4 | 14.8 |
| 26.7 | 15.8 |
| 27.5 | 8.7 |
| 29.4 | 51.6 |
| 29.9 | 21.9 |
| 30.6 | 10.9 |
| 33.5 | 2.0 |

TABLE 3B

XRPD peak list for 8-(2-fluorobenzyl)-6-(3-(trifluoromethyl)-1H-1,2,4-triazol-5-yl)imidazo[1,2-a]pyrazine Hydrate 1, acquired at room temperature in reflection mode using a Panalytical Empyrean system described above.

| Pos. [°2Th.] | Rel. Int. [%] |
|---|---|
| 8.8 | 7.2 |
| 9.4 | 13.7 |
| 11.7 | 53.8 |
| 12.2 | 4.5 |
| 13.7 | 17.6 |
| 14.0 | 12.9 |
| 15.5 | 56.1 |
| 16.7 | 5.7 |
| 17.2 | 100.0 |
| 17.9 | 73.4 |
| 18.5 | 49.8 |
| 19.4 | 15.8 |
| 20.3 | 6.6 |
| 21.4 | 2.0 |
| 22.3 | 24.4 |
| 23.3 | 42.2 |
| 23.6 | 15.5 |
| 24.4 | 32.5 |
| 25.1 | 86.0 |
| 25.6 | 10.1 |
| 27.0 | 16.4 |
| 27.7 | 9.0 |
| 28.6 | 2.0 |
| 29.6 | 55.4 |
| 30.1 | 17.9 |
| 30.9 | 9.7 |
| 32.2 | 4.1 |
| 33.6 | 3.4 |
| 34.0 | 3.2 |
| 35.0 | 2.1 |
| 37.6 | 1.7 |
| 38.9 | 0.9 |

TABLE 4A

XRPD peak list for 8-(2-fluorobenzyl)-6-(3-(trifluoromethyl)-1H-1,2,4-triazol-5-yl)imidazo[1,2-a]pyrazine Hydrate 2, acquired at room temperature in reflection mode using a Bruker D8 Discover system described above.

| Pos. [°2Th.] | Rel. Int. [%] |
|---|---|
| 9.0 | 8.7 |
| 10.4 | 58.2 |
| 14.9 | 19.6 |
| 15.5 | 100.0 |
| 17.8 | 19.8 |
| 18.4 | 66.2 |
| 18.7 | 74.1 |
| 20.7 | 25.7 |
| 21.2 | 26.4 |
| 21.9 | 37.3 |
| 22.7 | 28.4 |
| 24.6 | 64.6 |
| 25.9 | 43.9 |
| 26.3 | 30.0 |
| 27.4 | 77.5 |
| 28.0 | 15.7 |
| 29.5 | 63.9 |
| 31.0 | 41.3 |
| 31.7 | 28.9 |
| 32.6 | 11.7 |
| 34.5 | 4.9 |

TABLE 4B

XRPD peak list for 8-(2-fluorobenzyl)-6-(3-(trifluoromethyl)-1H-1,2,4-triazol-5-yl)imidazo[1,2-a]pyrazine Hydrate 2, acquired at room temperature in reflection mode using a Panalytical Empyrean system described above.

| Pos. [°2Th.] | Rel. Int. [%] |
|---|---|
| 7.3 | 60.6 |
| 9.3 | 10.0 |
| 10.6 | 74.5 |
| 13.2 | 2.1 |
| 15.2 | 28.8 |
| 15.8 | 76.1 |
| 15.9 | 100.0 |
| 17.1 | 7.3 |
| 18.1 | 25.2 |
| 18.7 | 26.0 |
| 19.0 | 25.6 |
| 21.0 | 13.4 |
| 21.5 | 10.3 |
| 22.2 | 11.2 |
| 23.0 | 17.1 |
| 23.8 | 3.6 |
| 24.8 | 20.5 |
| 25.1 | 26.0 |
| 26.2 | 13.8 |
| 26.6 | 28.6 |
| 27.6 | 64.8 |
| 29.8 | 19.3 |
| 31.2 | 10.8 |
| 32.0 | 5.7 |
| 32.8 | 5.0 |
| 34.6 | 2.9 |
| 35.1 | 3.7 |
| 36.9 | 1.6 |

TABLE 5A

XRPD peak list for 8-(2-fluorobenzyl)-6-(3-(trifluoromethyl)-1H-1,2,4-triazol-5-yl)imidazo[1,2-a]pyrazine Hydrate 3, acquired at room temperature in reflection mode using a Bruker D8 Discover system described above.

| Pos. [°2Th.] | Rel. Int. [%] |
|---|---|
| 8.5 | 4.2 |
| 10.3 | 35.8 |
| 12.1 | 27.6 |
| 13.5 | 28.4 |
| 14.5 | 9.2 |
| 15.9 | 35.2 |
| 16.9 | 58.4 |
| 17.6 | 22.0 |
| 18.5 | 18.0 |
| 20.3 | 11.2 |
| 21.0 | 12.4 |
| 22.0 | 23.8 |
| 22.9 | 29.8 |
| 24.4 | 100.0 |
| 25.0 | 21.4 |
| 26.6 | 11.0 |
| 28.9 | 25.5 |
| 30.8 | 5.7 |
| 33.0 | 6.4 |
| 36.0 | 3.3 |

TABLE 5B

XRPD peak list for 8-(2-fluorobenzyl)-6-(3-(trifluoromethyl)-1H-1,2,4-triazol-5-yl)imidazo[1,2-a]pyrazine Hydrate 3, acquired at room temperature in reflection mode using a Panalytical Empyrean system described above.

| Pos. [°2Th.] | Rel. Int. [%] |
|---|---|
| 8.3 | 2.4 |
| 8.7 | 2.9 |
| 10.5 | 73.3 |
| 12.0 | 11.2 |
| 12.8 | 16.9 |
| 13.9 | 30.8 |
| 14.5 | 3.2 |
| 15.0 | 18.7 |
| 16.5 | 33.1 |
| 17.2 | 34.1 |
| 17.6 | 100.0 |
| 18.3 | 17.2 |
| 19.1 | 18.9 |
| 20.3 | 23.9 |
| 21.1 | 3.9 |
| 21.6 | 3.5 |
| 22.2 | 8.0 |
| 22.6 | 14.9 |
| 23.7 | 27.5 |
| 24.1 | 8.0 |
| 24.7 | 9.7 |
| 25.0 | 10.0 |
| 25.6 | 26.7 |
| 26.2 | 20.1 |
| 27.7 | 3.1 |
| 28.5 | 3.1 |
| 30.1 | 41.2 |
| 31.9 | 4.5 |
| 34.1 | 3.4 |
| 35.0 | 1.6 |
| 35.6 | 1.4 |
| 37.1 | 2.4 |
| 38.8 | 2.5 |

TABLE 6

XRPD peak list for 8-(2-fluorobenzyl)-6-(3-(trifluoromethyl)-1H-1,2,4-triazol-5-yl)imidazo[1,2-a]pyrazine Ethanol Solvate, acquired at room temperature in reflection mode using a Bruker D8 Discover system described above.

| Pos. [°2Th.] | Rel. Int. [%] |
|---|---|
| 8.6 | 2.8 |
| 10.4 | 72.0 |
| 11.8 | 11.5 |
| 12.7 | 15.1 |
| 13.8 | 29.2 |
| 14.9 | 14.6 |
| 16.4 | 31.1 |
| 17.1 | 36.5 |
| 17.5 | 100.0 |
| 18.2 | 14.8 |
| 19.0 | 19.2 |
| 20.2 | 29.0 |
| 22.5 | 15.9 |
| 23.5 | 28.4 |
| 24.5 | 11.9 |
| 25.5 | 33.1 |
| 26.1 | 22.4 |
| 27.4 | 4.4 |
| 30.0 | 64.4 |
| 31.8 | 6.6 |
| 33.9 | 3.9 |
| 36.9 | 3.8 |
| 38.7 | 4.5 |

TABLE 7

XRPD peak list for 8-(2-fluorobenzyl)-6-(3-(trifluoromethyl)-1H-1,2,4-triazol-5-yl)imidazo[1,2-a]pyrazine Methanol Solvate, acquired at room temperature in reflection mode using a Bruker D8 Discover system described above.

| Pos. [°2Th.] | Rel. Int. [%] |
|---|---|
| 7.7 | 30.6 |
| 10.3 | 13.0 |
| 11.0 | 31.0 |
| 11.6 | 11.9 |
| 14.2 | 52.8 |
| 15.2 | 12.6 |
| 16.2 | 42.6 |
| 17.1 | 94.8 |
| 17.8 | 36.6 |
| 18.4 | 12.1 |
| 19.3 | 21.6 |
| 20.0 | 27.4 |
| 21.2 | 26.0 |
| 23.0 | 40.2 |
| 24.2 | 100.0 |
| 26.1 | 18.2 |
| 27.3 | 12.0 |
| 29.0 | 85.9 |
| 29.6 | 37.4 |

TABLE 8

XRPD peak list for 8-(2-fluorobenzyl)-6-(3-(trifluoromethyl)-1H-1,2,4-triazol-5-yl)imidazo[1,2-a]pyrazine Methyl Ethyl Ketone Solvate, acquired at room temperature in reflection mode using a Bruker D8 Discover system described above.

| Pos. [°2Th.] | Rel. Int. [%] |
|---|---|
| 8.5 | 4.9 |
| 9.0 | 14.6 |
| 10.8 | 8.0 |
| 12.3 | 25.4 |
| 13.7 | 49.1 |
| 14.7 | 22.8 |
| 15.8 | 33.2 |
| 17.3 | 100.0 |
| 17.8 | 49.1 |
| 18.4 | 54.0 |
| 20.3 | 12.9 |
| 21.1 | 89.7 |
| 22.0 | 17.8 |
| 22.8 | 39.6 |
| 23.3 | 10.6 |
| 24.0 | 61.5 |
| 24.3 | 62.8 |
| 25.1 | 39.4 |
| 25.8 | 25.7 |
| 26.9 | 34.4 |
| 27.7 | 63.5 |
| 29.7 | 25.5 |
| 31.0 | 7.7 |
| 31.5 | 4.4 |
| 32.3 | 10.2 |
| 35.6 | 9.5 |
| 36.6 | 4.1 |
| 37.9 | 9.3 |

TABLE 9

XRPD peak list for 8-(2-fluorobenzyl)-6-(3-(trifluoromethyl)-1H-1,2,4-triazol-5-yl)imidazo[1,2-a]pyrazine Dichloromethane Solvate, acquired at room temperature in reflection mode using a Bruker D8 Discover system described above.

| Pos. [°2Th.] | Rel. Int. [%] |
|---|---|
| 14.4 | 23.2 |
| 15.7 | 37.6 |
| 19.7 | 33.0 |
| 20.9 | 33.0 |
| 21.8 | 19.3 |
| 22.7 | 15.2 |
| 24.0 | 100.0 |

TABLE 10

XRPD peak list for 8-(2-fluorobenzyl)-6-(3-(trifluoromethyl)-1H-1,2,4-triazol-5-yl)imidazo[1,2-a]pyrazine Acetonitrile Solvate, acquired at room temperature in reflection mode using a Bruker D8 Discover system described above.

| Pos. [°2Th.] | Rel. Int. [%] |
|---|---|
| 10.6 | 29.2 |
| 14.4 | 100.0 |
| 17.3 | 49.8 |
| 18.7 | 37.0 |
| 21.7 | 26.7 |
| 23.2 | 21.1 |
| 25.3 | 40.2 |
| 25.9 | 22.6 |
| 26.7 | 11.8 |
| 28.0 | 8.1 |
| 32.7 | 4.0 |

TABLE 11

XRPD peak list for 8-(2-fluorobenzyl)-6-(3-(trifluoromethyl)-1H-1,2,4-triazol-5-yl)imidazo[1,2-a]pyrazine Ethyl Acetate Solvate, acquired at room temperature in reflection mode using a Bruker D8 Discover system described above.

| Pos. [°2Th.] | Rel. Int. [%] |
|---|---|
| 8.2 | 11.3 |
| 10.5 | 7.9 |
| 12.9 | 6.1 |
| 15.2 | 19.2 |
| 16.4 | 19.7 |
| 18.7 | 38.6 |
| 19.7 | 23.7 |
| 21.4 | 20.1 |
| 23.4 | 19.5 |
| 25.3 | 100.0 |
| 28.9 | 7.7 |
| 32.1 | 14.5 |
| 37.5 | 4.4 |

Differential Scanning Calorimetry (DSC)

Differential Scanning Calorimetry (DSC) was used to determine the melting point of crystalline materials and to discriminate between different polymorphs. The analysis was carried out on a Q200 V24.3 Build 115 instruments. Sample sizes of 0.5 to 2.0 mg were weighed into tared aluminum t-zero pans, hermetically sealed, and pin-holed. Samples were equilibrated at 25° C. then heated at 5.0° C. per minute up to 250° C. The data was analyzed with the Universal Analysis 2000 software.

The differential scanning calorimetry (DSC) analysis of 8-(2-fluorobenzyl)-6-(3-(trifluoromethyl)-1H-1,2,4-triazol-5-yl)imidazo[1,2-a]pyrazine Form A shows that Form A has a melting point of 195-196° C. (FIG. 2).

The DSC analysis of 8-(2-fluorobenzyl)-6-(3-(trifluoromethyl)-1H-1,2,4-triazol-5-yl)imidazo[1,2-a]pyrazine Form B shows that Form B has an initial melting point at 177° C., which is followed by an immediate crystallization to anhydrous Form A, which melts at 196.4° C. (FIG. 6).

The DSC analysis of 8-(2-fluorobenzyl)-6-(3-(trifluoromethyl)-1H-1,2,4-triazol-5-yl)imidazo[1,2-a]pyrazine Hydrate 1 is depicted in FIG. 9. Two initial endotherms below 100° C. are evident, signifying the loss of water. No recrystallization is observed, but the melting observed at 195° C. is consistent with the melting point of Form A, thus indicating that the loss of the moisture from Hydrate 1 results in the formation of anhydrous Form A.

The DSC analysis of 8-(2-fluorobenzyl)-6-(3-(trifluoromethyl)-1H-1,2,4-triazol-5-yl)imidazo[1,2-a]pyrazine Hydrate 2 is depicted in FIG. 12. An endotherm at ~88° C. is evident, signifying the loss of water. No recrystallization is observed, but the melting observed at ~195° C. is consistent with the melt of Form A, thus indicating that the loss of the moisture from Hydrate 2 results in the formation of anhydrous Form A.

The DSC analysis of 8-(2-fluorobenzyl)-6-(3-(trifluoromethyl)-1H-1,2,4-triazol-5-yl)imidazo[1,2-a]pyrazine Hydrate 3 is depicted in FIG. 15. An endotherm at ~64° C. is evident, signifying the loss of water. No recrystallization is observed, but the melting observed at 195° C. is consistent with the melt of Form A, thus indicating that the loss of the moisture from Hydrate 3 results in the formation of anhydrous Form A.

Thermogravimetric Analysis (TGA)

Thermogravimetric Analysis (TGA) results for residual solids were obtained using the TA Instruments model Q5000 TGA V3.8 Build 256 Sample sizes of 2 to 10 mg were added to tared platinum sample pans and heated at 5° C./min from room temperature up to 250° C. The data was analyzed with the Universal Analysis 2000 software.

The thermal gravimetric analysis (TGA) of 8-(2-fluorobenzyl)-6-(3-(trifluoromethyl)-1H-1,2,4-triazol-5-yl)imidazo[1,2-a]pyrazine Form A indicates no weight loss until the melt, signifying that Form A is anhydrous (FIG. 3).

The TGA analysis of 8-(2-fluorobenzyl)-6-(3-(trifluoromethyl)-1H-1,2,4-triazol-5-yl)imidazo[1,2-a]pyrazine Form B indicates no weight loss until the melt, signifying that Form B is anhydrous (FIG. 7).

The TGA analysis of 8-(2-fluorobenzyl)-6-(3-(trifluoromethyl)-1H-1,2,4-triazol-5-yl)imidazo[1,2-a]pyrazine Hydrate 1 shows a 4.67% weight loss prior to 100° C., consistent with the loss of 1M Eq of water (FIG. 10). Hydrate 1 is likely a monohydrate.

The TGA analysis of 8-(2-fluorobenzyl)-6-(3-(trifluoromethyl)-1H-1,2,4-triazol-5-yl)imidazo[1,2-a]pyrazine Hydrate 2 shows a 4.75% weight loss prior to 100° C., consistent with the loss of 1M Eq of water (FIG. 13). Hydrate 2 is likely a monohydrate.

The TGA analysis of 8-(2-fluorobenzyl)-6-(3-(trifluoromethyl)-1H-1,2,4-triazol-5-yl)imidazo[1,2-a]pyrazine Hydrate 3 shows a two-step weight loss of 3.32% weight loss prior to 100° C. (FIG. 16). The initial weight loss starts from the onset of heating indicating the possibility of residual moisture. The total weight loss observed is less than the required about needed for a monohydrate, thus it is likely that Hydrate 3 is a hemi-hydrate with the presence of extra residual moisture.

The TGA analysis of 8-(2-fluorobenzyl)-6-(3-(trifluoromethyl)-1H-1,2,4-triazol-5-yl)imidazo[1,2-a]pyrazine Ethanol Solvate shows a weight loss of 4.80% weight loss prior to 100° C. (FIG. 18).

The TGA analysis of 8-(2-fluorobenzyl)-6-(3-(trifluoromethyl)-1H-1,2,4-triazol-5-yl)imidazo[1,2-a]pyrazine Methanol Solvate shows a weight loss of 6.76% weight loss prior to 100° C. (FIG. 20).

The TGA analysis of 8-(2-fluorobenzyl)-6-(3-(trifluoromethyl)-1H-1,2,4-triazol-5-yl)imidazo[1,2-a]pyrazine Dichloromethane Solvate shows a weight loss of 5.39% weight loss after 100° C. (FIG. 23).

The TGA analysis of 8-(2-fluorobenzyl)-6-(3-(trifluoromethyl)-1H-1,2,4-triazol-5-yl)imidazo[1,2-a]pyrazine Acetonitrile Solvate shows an initial weight loss of 0.98% followed by a 2% weight loss prior to 100° C. (FIG. 25).

Figure 27:
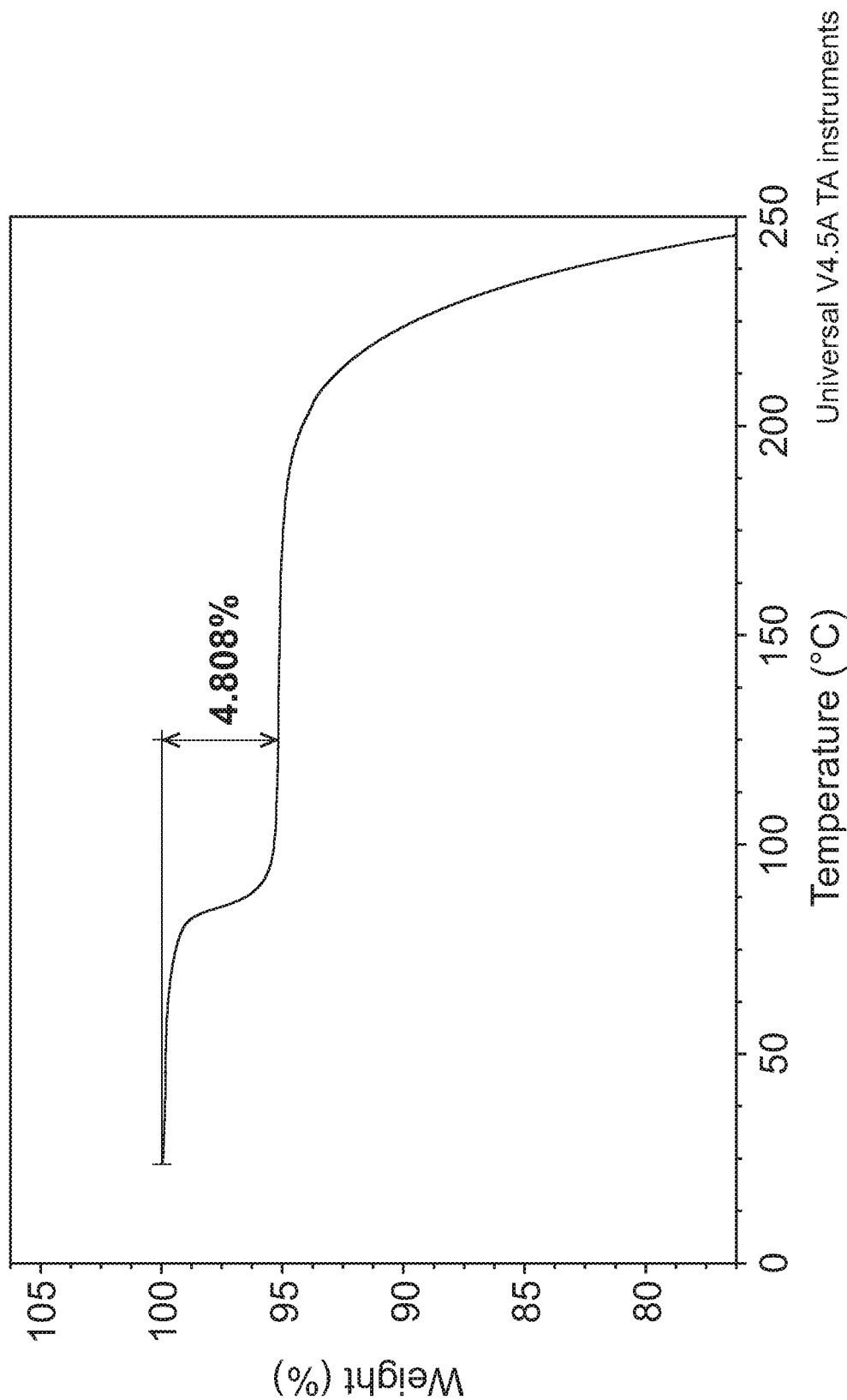
FIG. 27 is a TGA analysis of 8-(2-fluorobenzyl)-6-(3-(trifluoromethyl)-1H-1,2,4-triazol-5-yl)imidazo[1,2-a]pyrazine ethyl acetate solvate.

The TGA analysis of 8-(2-fluorobenzyl)-6-(3-(trifluoromethyl)-1H-1,2,4-triazol-5-yl)imidazo[1,2-a]pyrazine Ethyl Acetate Solvate shows a weight loss of 4.81% weight loss after 100° C. (FIG. 27).

Dynamic Vapor Sorption (DVS)

The Adsorption/Desorption determination was performed using a Q5000 V3.3 TGA-SA instrument. The sample was dispensed on a tarred platinum pan and a ramp run from 10% relative humidity (RH) to 90% RH and then back down to 10% RH with 10% RH increments. The ramp was isothermal at 25° C. Water was used as the solvent for all DVS analysis. The data was analyzed with the Universal Analysis 2000 software.

The dynamic vapor sorption (DVS) analysis of 8-(2-fluorobenzyl)-6-(3-(trifluoromethyl)-1H-1,2,4-triazol-5-yl)imidazo[1,2-a]pyrazine shows that Form A is anhydrous, picking up less than 0.4% moisture up to 95% RH (FIG. 4).

The invention claimed is:

1. A crystalline Form A of 8-(2-fluorobenzyl)-6-(3-(trifluoromethyl)-1H-1,2,4-triazol-5-yl)imidazo[1,2-a]pyrazine of the formula:

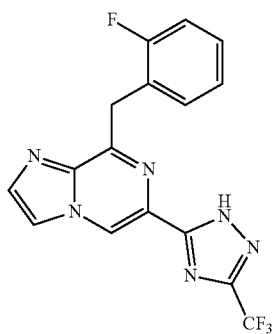 [SMILES: Fc1ccccc1Cc1nc(-c2nc(C(F)(F)F)n[nH]2)cn2ccnc12]

wherein the crystalline form is characterized by a powder X-ray diffraction pattern comprising at least three diffraction peaks at diffraction angles (°2θ) selected from the group consisting of 7.0°±0.2°2θ, 8.3°±0.2°2θ, 11.1°±0.2°2θ, 14.3°±0.2°2θ, and 15.0°±0.2°2θ.

2. The crystalline form of claim 1, wherein the crystalline form is further characterized by a powder X-ray diffraction pattern comprising at least four diffraction peaks at diffraction angles (°2θ) selected from the group consisting of 7.0°±0.2°2θ, 8.3°±0.2°2θ, 11.1°±0.2°2θ, 14.3°±0.2°2θ, and 15.0°±0.2°2θ.

3. The crystalline form of claim 2, wherein the crystalline form is further characterized by a powder X-ray diffraction pattern comprising diffraction peaks at diffraction angles (°2θ) of 7.0°±0.2°2θ, 8.3°±0.2°2θ, 11.1°±0.2° 2θ, 14.3°±0.2°2θ, and 15.0°±0.2°2θ.

4. The crystalline form of claim 3, wherein the crystalline form is further characterized by a powder X-ray diffraction pattern comprising diffraction peaks at diffraction angles (°2θ) of 7.0°±0.2°2θ, 8.3°±0.2°2θ, 11.1°±0.2°2θ, 14.3°±0.2°2θ, 15.0°±0.2°2θ, 15.9°±0.2°2θ, 16.7°±0.2°2θ, 17.6°±0.2°2θ, 19.1°±0.2°2θ, 20.2°±0.2°2θ, 21.6°±0.2°2θ, 24.9°±0.2°2θ, and 25.8°±0.2°2θ.

5. The crystalline form of claim 1, wherein the diffraction peaks have a relative intensity of at least 10%.

6. The crystalline form of claim 5, wherein the diffraction peaks have a relative intensity of at least 15%.

7. The crystalline form of claim 6, wherein the diffraction peaks have a relative intensity of at least 20%.

8. The crystalline form of claim 7, wherein the diffraction peaks have a relative intensity of at least 25%.

9. The crystalline form of claim 1, wherein the crystalline form is further characterized by a differential scanning calorimetry pattern as shown in FIG. 2.

10. The crystalline form of claim 1, wherein the crystalline form is further characterized by a thermal gravimetric analysis pattern as shown in FIG. 3.

11. The crystalline form of claim 1, wherein the crystalline form is further characterized by a dynamic vapor sorption analysis pattern as shown in FIG. 4.

12. A pharmaceutical composition comprising the crystalline form of claim 1 and a pharmaceutically acceptable carrier or diluent.

13. A method for treating a central nervous system disorder in a patient in need thereof, wherein the method comprises the step of administering to the patient a therapeutically effective amount of the crystalline form of claim 1.

* * * * *